US012606615B2

(12) United States Patent
Miyagi et al.

(10) Patent No.: US 12,606,615 B2
(45) Date of Patent: Apr. 21, 2026

(54) ANTI-FGF23 ANTIBODY OR ANTIBODY FRAGMENT THEREOF

(71) Applicant: Kyowa Kirin Co., Ltd., Tokyo (JP)

(72) Inventors: Hikaru Miyagi, Tokyo (JP); Taiji Oashi, Tokyo (JP); Kenta Nakajima, Tokyo (JP); Sari Ogasawara, Tokyo (JP)

(73) Assignee: KYOWA KIRIN CO., LTD., Tokyo (JP)

( * ) Notice: Subject to any disclaimer, the term of this patent is extended or adjusted under 35 U.S.C. 154(b) by 0 days.

(21) Appl. No.: 18/964,217

(22) Filed: Nov. 29, 2024

(65) Prior Publication Data

US 2025/0163140 A1     May 22, 2025

Related U.S. Application Data

(63) Continuation of application No. PCT/JP2023/029098, filed on Aug. 9, 2023.

(30) Foreign Application Priority Data

| | | |
|---|---|---|
| Aug. 10, 2022 | (JP) | 2022-128011 |
| Oct. 12, 2022 | (JP) | 2022-164256 |

(51) Int. Cl.
C07K 16/22       (2006.01)
A61K 39/00       (2006.01)

(52) U.S. Cl.
CPC ........ C07K 16/22 (2013.01); A61K 2039/505 (2013.01); C07K 2317/76 (2013.01); C07K 2317/92 (2013.01); C07K 2317/94 (2013.01)

(58) Field of Classification Search
None
See application file for complete search history.

(56) References Cited

U.S. PATENT DOCUMENTS

| | | | | |
|---|---|---|---|---|
| 10,202,446 | B2 * | 2/2019 | Yamazaki | ............... A61P 35/00 |
| 2005/0171339 | A1 | 8/2005 | Sugo et al. | |
| 2006/0287508 | A1 | 12/2006 | Sugo et al. | |
| 2008/0138860 | A1 | 6/2008 | Torikai et al. | |
| 2009/0148461 | A1 | 6/2009 | Yamazaki et al. | |
| 2010/0298542 | A1 | 11/2010 | Igawa et al. | |
| 2011/0182913 | A1 | 7/2011 | Yamazaki et al. | |
| 2016/0159895 | A1 | 6/2016 | Yamazaki et al. | |
| 2017/0342154 | A1 | 11/2017 | Igawa et al. | |
| 2018/0118813 | A1 | 5/2018 | Torikai et al. | |
| 2019/0106485 | A1 | 4/2019 | Yamazaki et al. | |
| 2022/0185876 | A1 | 6/2022 | Jayaraman et al. | |
| 2022/0251225 | A1 | 8/2022 | Igawa et al. | |

FOREIGN PATENT DOCUMENTS

| | | |
|---|---|---|
| JP | 2022-527790 | 6/2022 |
| WO | 03/057881 | 7/2003 |
| WO | 2006/085518 | 8/2006 |
| WO | 2008/099969 | 8/2008 |
| WO | 2009/041613 | 4/2009 |
| WO | WO-2020205523 A1 * | 10/2020 ......... A61K 39/3955 |
| WO | WO-2024034638 A1 * | 2/2024 ............. C07K 16/22 |

OTHER PUBLICATIONS

International Search Report issued Oct. 10, 2023 in International (PCT) Application No. PCT/JP2023/029098.
Ornitz, Daivd M. et al., "The Fibroblast Growth Factor signaling pathway", Wires Dev Biol, 2015, vol. 4, pp. 215-266.
Itoh, Nobuyuki et al., "Fibroblast growth factors: from molecular evolution to roles in development, metabolism and disease", The Journal of Biochemistry, 2011, vol. 149, No. 2, pp. 121-130.
Yamashita, Tetsuo et al., "Identification of a Novel Fibroblast Growth Factor, FGF-23, Preferentially Expressed in the Ventrolateral Thalamic Nucleus of the Brain", Biochemical and Biophysical Research Communications, 2000, vol. 277, pp. 494-498.
Hori, Michiko et al., "Minireview: Fibroblast Growth Factor 23 in Phosphate Homeostasis and Bone Metabolism", Endocrinology, Jan. 2011, vol. 152, No. 1, pp. 4-10.
Sabbagh, Yves et al., "PHEXdb, a Locus-Specific Database for Mutations Causing X-Linked Hypophosphatemia", Human Mutation, 2000, vol. 16, pp. 1-6.
Yuan, Baozhi et al., "Aberrant Phex function in osteoblasts and osteocytes alone underlies murine X-linked hypophosphatemia", The Journal of Clinical Investigation, Feb. 2008, vol. 118, No. 2, pp. 722-734.
Beck, L. et al., "Pex/PEX tissue distribution and evidence for a deletion in the 3' region of the PEX gene in X-linked hypophosphatemic mice", The Journal of Clinical Investigation, Mar. 1997, vol. 99, No. 6, pp. 1200-1209.
Beck-Nielsen, Signe Sparre et al., "FGF23 and its role in X-linked hypophosphatemia-related morbidity", Orphanet Journal of Rare Diseases, 2019, vol. 14, No. 58, 25 pages.
Imel, Erik A. et al., "Burosumab versus continuation of conventional therapy in children with X-linked hypophosphatemia: a randomised, active-controlled, open-label, phase 3 trial", Lancet, 2019, Jun. 2020, vol. 393, No. 10189, pp. 2416-2427.
Carpenter, Thomas O. et al., "A Clinician's Guide to X-Linked Hypophosphatemia", J Bone Miner Res, Jul. 2011, vol. 26, No. 7, pp. 1381-1388.

* cited by examiner

*Primary Examiner* — Marianne P Allen
(74) *Attorney, Agent, or Firm* — Wenderoth, Lind & Ponack, L.L.P.

(57) ABSTRACT

The present invention relates to an antibody or an antibody fragment thereof which binds to FGF23. The antibody comprises a heavy chain variable region (hereinafter, described as VH) comprising the amino acid sequence represented by SEQ ID NO: 1 and a light chain variable region (hereinafter, described as VL) comprising the amino acid sequence represented by SEQ ID NO: 2. At least the amino acid residue at position 100 or the amino acid residue at position 105 of the amino acid sequence represented by SEQ ID NO: 1 in the VH is substituted with another amino acid residue.

6 Claims, No Drawings

Specification includes a Sequence Listing.

SEQUENCE LISTING

```
Sequence total quantity: 59
SEQ ID NO: 1              moltype = AA  length = 117
FEATURE                  Location/Qualifiers
REGION                   1..117
                         note = description of the artificial sequence: the amino
                          acid sequenceof A antibody VH
source                   1..117
                         mol_type = protein
                         organism = synthetic construct
SEQUENCE: 1
QVQLVQSGAE VKKPGASVKV SCKASGYTFT NHYMHWVRQA PGQGLEWMGI INPISGSTSN  60
AQKFQGRVTM TRDTSTSTVY MELSSLRSED TAVYYCARDI VDAFDFWGQG TMVTVSS      117

SEQ ID NO: 2              moltype = AA  length = 106
FEATURE                  Location/Qualifiers
```

```
REGION                    1..106
                          note = description of the artificial sequence: the amino
                           acid sequenceof A antibody VL
source                    1..106
                          mol_type = protein
                          organism = synthetic construct
SEQUENCE: 2
AIQLTQSPSS LSASVGDRVT ITCRASQGIS SALVWYQQKP GKAPKLLIYD ASSLESGVPS   60
RFSGSGSGTD FTLTISSLQP EDFATYYCQQ FNDYFTFGPG TKVDIK                  106

SEQ ID NO: 3              moltype = AA   length = 117
FEATURE                   Location/Qualifiers
REGION                    1..117
                          note = description of the artificial sequence: the amino
                           acid sequenceof I100A antibody VH
source                    1..117
                          mol_type = protein
                          organism = synthetic construct
SEQUENCE: 3
QVQLVQSGAE VKKPGASVKV SCKASGYTFT NHYMHWVRQA PGQGLEWMGI INPISGSTSN   60
AQKFQGRVTM TRDTSTSTVY MELSSLRSED TAVYYCARDA VDAFDFWGQG TMVTVSS      117

SEQ ID NO: 4              moltype = AA   length = 117
FEATURE                   Location/Qualifiers
REGION                    1..117
                          note = description of the artificial sequence: the amino
                           acid sequenceof I100L antibody VH
source                    1..117
                          mol_type = protein
                          organism = synthetic construct
SEQUENCE: 4
QVQLVQSGAE VKKPGASVKV SCKASGYTFT NHYMHWVRQA PGQGLEWMGI INPISGSTSN   60
AQKFQGRVTM TRDTSTSTVY MELSSLRSED TAVYYCARDL VDAFDFWGQG TMVTVSS      117

SEQ ID NO: 5              moltype = AA   length = 117
FEATURE                   Location/Qualifiers
REGION                    1..117
                          note = description of the artificial sequence: the amino
                           acid sequenceof I100V antibody VH
source                    1..117
                          mol_type = protein
                          organism = synthetic construct
SEQUENCE: 5
QVQLVQSGAE VKKPGASVKV SCKASGYTFT NHYMHWVRQA PGQGLEWMGI INPISGSTSN   60
AQKFQGRVTM TRDTSTSTVY MELSSLRSED TAVYYCARDV VDAFDFWGQG TMVTVSS      117

SEQ ID NO: 6              moltype = AA   length = 117
FEATURE                   Location/Qualifiers
REGION                    1..117
                          note = description of the artificial sequence: the amino
                           acid sequenceof I100Y antibody VH
source                    1..117
                          mol_type = protein
                          organism = synthetic construct
SEQUENCE: 6
QVQLVQSGAE VKKPGASVKV SCKASGYTFT NHYMHWVRQA PGQGLEWMGI INPISGSTSN   60
AQKFQGRVTM TRDTSTSTVY MELSSLRSED TAVYYCARDY VDAFDFWGQG TMVTVSS      117

SEQ ID NO: 7              moltype = AA   length = 117
FEATURE                   Location/Qualifiers
REGION                    1..117
                          note = description of the artificial sequence: the amino
                           acid sequenceof I100W antibody VH
source                    1..117
                          mol_type = protein
                          organism = synthetic construct
SEQUENCE: 7
QVQLVQSGAE VKKPGASVKV SCKASGYTFT NHYMHWVRQA PGQGLEWMGI INPISGSTSN   60
AQKFQGRVTM TRDTSTSTVY MELSSLRSED TAVYYCARDW VDAFDFWGQG TMVTVSS      117

SEQ ID NO: 8              moltype = AA   length = 117
FEATURE                   Location/Qualifiers
REGION                    1..117
                          note = description of the artificial sequence: the amino
                           acid sequenceof I100T antibody VH
source                    1..117
                          mol_type = protein
                          organism = synthetic construct
SEQUENCE: 8
```

```
QVQLVQSGAE VKKPGASVKV SCKASGYTFT NHYMHWVRQA PGQGLEWMGI INPISGSTSN  60
AQKFQGRVTM TRDTSTSTVY MELSSLRSED TAVYYCARDT VDAFDFWGQG TMVTVSS      117

SEQ ID NO: 9              moltype = AA  length = 117
FEATURE                   Location/Qualifiers
REGION                    1..117
                          note = description of the artificial sequence: the amino
                           acid sequenceof I100S antibody VH
source                    1..117
                          mol_type = protein
                          organism = synthetic construct
SEQUENCE: 9
QVQLVQSGAE VKKPGASVKV SCKASGYTFT NHYMHWVRQA PGQGLEWMGI INPISGSTSN  60
AQKFQGRVTM TRDTSTSTVY MELSSLRSED TAVYYCARDS VDAFDFWGQG TMVTVSS      117

SEQ ID NO: 10             moltype = AA  length = 117
FEATURE                   Location/Qualifiers
REGION                    1..117
                          note = description of the artificial sequence: the amino
                           acid sequenceof I100R antibody VH
source                    1..117
                          mol_type = protein
                          organism = synthetic construct
SEQUENCE: 10
QVQLVQSGAE VKKPGASVKV SCKASGYTFT NHYMHWVRQA PGQGLEWMGI INPISGSTSN  60
AQKFQGRVTM TRDTSTSTVY MELSSLRSED TAVYYCARDR VDAFDFWGQG TMVTVSS      117

SEQ ID NO: 11             moltype = AA  length = 117
FEATURE                   Location/Qualifiers
REGION                    1..117
                          note = description of the artificial sequence: the amino
                           acid sequenceof I100Q antibody VH
source                    1..117
                          mol_type = protein
                          organism = synthetic construct
SEQUENCE: 11
QVQLVQSGAE VKKPGASVKV SCKASGYTFT NHYMHWVRQA PGQGLEWMGI INPISGSTSN  60
AQKFQGRVTM TRDTSTSTVY MELSSLRSED TAVYYCARDQ VDAFDFWGQG TMVTVSS      117

SEQ ID NO: 12             moltype = AA  length = 117
FEATURE                   Location/Qualifiers
REGION                    1..117
                          note = description of the artificial sequence: the amino
                           acid sequenceof I100N antibody VH
source                    1..117
                          mol_type = protein
                          organism = synthetic construct
SEQUENCE: 12
QVQLVQSGAE VKKPGASVKV SCKASGYTFT NHYMHWVRQA PGQGLEWMGI INPISGSTSN  60
AQKFQGRVTM TRDTSTSTVY MELSSLRSED TAVYYCARDN VDAFDFWGQG TMVTVSS      117

SEQ ID NO: 13             moltype = AA  length = 117
FEATURE                   Location/Qualifiers
REGION                    1..117
                          note = description of the artificial sequence: the amino
                           acid sequenceof I100M antibody VH
source                    1..117
                          mol_type = protein
                          organism = synthetic construct
SEQUENCE: 13
QVQLVQSGAE VKKPGASVKV SCKASGYTFT NHYMHWVRQA PGQGLEWMGI INPISGSTSN  60
AQKFQGRVTM TRDTSTSTVY MELSSLRSED TAVYYCARDM VDAFDFWGQG TMVTVSS      117

SEQ ID NO: 14             moltype = AA  length = 117
FEATURE                   Location/Qualifiers
REGION                    1..117
                          note = description of the artificial sequence: the amino
                           acid sequenceof I100K antibody VH
source                    1..117
                          mol_type = protein
                          organism = synthetic construct
SEQUENCE: 14
QVQLVQSGAE VKKPGASVKV SCKASGYTFT NHYMHWVRQA PGQGLEWMGI INPISGSTSN  60
AQKFQGRVTM TRDTSTSTVY MELSSLRSED TAVYYCARDK VDAFDFWGQG TMVTVSS      117

SEQ ID NO: 15             moltype = AA  length = 117
FEATURE                   Location/Qualifiers
REGION                    1..117
                          note = description of the artificial sequence: the amino
```

```
                            acid sequenceof I100H antibody VH
source                      1..117
                            mol_type = protein
                            organism = synthetic construct
SEQUENCE: 15
QVQLVQSGAE VKKPGASVKV SCKASGYTFT NHYMHWVRQA PGQGLEWMGI INPISGSTSN  60
AQKFQGRVTM TRDTSTSTVY MELSSLRSED TAVYYCARDH VDAFDFWGQG TMVTVSS     117

SEQ ID NO: 16               moltype = AA  length = 117
FEATURE                     Location/Qualifiers
source                      1..117
                            mol_type = protein
                            organism = synthetic construct
REGION                      1..117
                            note = description of the artificial sequence: the amino
                             acid sequence of I100G antibody VH
SEQUENCE: 16
QVQLVQSGAE VKKPGASVKV SCKASGYTFT NHYMHWVRQA PGQGLEWMGI INPISGSTSN  60
AQKFQGRVTM TRDTSTSTVY MELSSLRSED TAVYYCARDG VDAFDFWGQG TMVTVSS     117

SEQ ID NO: 17               moltype = AA  length = 117
FEATURE                     Location/Qualifiers
REGION                      1..117
                            note = description of the artificial sequence: the amino
                             acid sequenceof I100F antibody VH
source                      1..117
                            mol_type = protein
                            organism = synthetic construct
SEQUENCE: 17
QVQLVQSGAE VKKPGASVKV SCKASGYTFT NHYMHWVRQA PGQGLEWMGI INPISGSTSN  60
AQKFQGRVTM TRDTSTSTVY MELSSLRSED TAVYYCARDF VDAFDFWGQG TMVTVSS     117

SEQ ID NO: 18               moltype = AA  length = 117
FEATURE                     Location/Qualifiers
REGION                      1..117
                            note = description of the artificial sequence: the amino
                             acid sequenceof I100E antibody VH
source                      1..117
                            mol_type = protein
                            organism = synthetic construct
SEQUENCE: 18
QVQLVQSGAE VKKPGASVKV SCKASGYTFT NHYMHWVRQA PGQGLEWMGI INPISGSTSN  60
AQKFQGRVTM TRDTSTSTVY MELSSLRSED TAVYYCARDE VDAFDFWGQG TMVTVSS     117

SEQ ID NO: 19               moltype = AA  length = 117
FEATURE                     Location/Qualifiers
REGION                      1..117
                            note = description of the artificial sequence: the amino
                             acid sequenceof I100D antibody VH
source                      1..117
                            mol_type = protein
                            organism = synthetic construct
SEQUENCE: 19
QVQLVQSGAE VKKPGASVKV SCKASGYTFT NHYMHWVRQA PGQGLEWMGI INPISGSTSN  60
AQKFQGRVTM TRDTSTSTVY MELSSLRSED TAVYYCARDD VDAFDFWGQG TMVTVSS     117

SEQ ID NO: 20               moltype = AA  length = 117
FEATURE                     Location/Qualifiers
REGION                      1..117
                            note = description of the artificial sequence: the amino
                             acid sequenceof D105A antibody VH
source                      1..117
                            mol_type = protein
                            organism = synthetic construct
SEQUENCE: 20
QVQLVQSGAE VKKPGASVKV SCKASGYTFT NHYMHWVRQA PGQGLEWMGI INPISGSTSN  60
AQKFQGRVTM TRDTSTSTVY MELSSLRSED TAVYYCARDI VDAFAFWGQG TMVTVSS     117

SEQ ID NO: 21               moltype = AA  length = 117
FEATURE                     Location/Qualifiers
REGION                      1..117
                            note = description of the artificial sequence: the amino
                             acid sequenceof D105E antibody VH
source                      1..117
                            mol_type = protein
                            organism = synthetic construct
SEQUENCE: 21
QVQLVQSGAE VKKPGASVKV SCKASGYTFT NHYMHWVRQA PGQGLEWMGI INPISGSTSN  60
AQKFQGRVTM TRDTSTSTVY MELSSLRSED TAVYYCARDI VDAFEFWGQG TMVTVSS     117
```

-continued

```
SEQ ID NO: 22              moltype = AA   length = 117
FEATURE                    Location/Qualifiers
REGION                     1..117
                           note = description of the artificial sequence: the amino
                            acid sequenceof D105F antibody VH
source                     1..117
                           mol_type = protein
                           organism = synthetic construct
SEQUENCE: 22
QVQLVQSGAE VKKPGASVKV SCKASGYTFT NHYMHWVRQA PGQGLEWMGI INPISGSTSN  60
AQKFQGRVTM TRDTSTSTVY MELSSLRSED TAVYYCARDI VDAFFFWGQG TMVTVSS      117

SEQ ID NO: 23              moltype = AA   length = 117
FEATURE                    Location/Qualifiers
REGION                     1..117
                           note = description of the artificial sequence: the amino
                            acid sequenceof D105G antibody VH
source                     1..117
                           mol_type = protein
                           organism = synthetic construct
SEQUENCE: 23
QVQLVQSGAE VKKPGASVKV SCKASGYTFT NHYMHWVRQA PGQGLEWMGI INPISGSTSN  60
AQKFQGRVTM TRDTSTSTVY MELSSLRSED TAVYYCARDI VDAFGFWGQG TMVTVSS      117

SEQ ID NO: 24              moltype = AA   length = 117
FEATURE                    Location/Qualifiers
REGION                     1..117
                           note = description of the artificial sequence: the amino
                            acid sequenceof D105H antibody VH
source                     1..117
                           mol_type = protein
                           organism = synthetic construct
SEQUENCE: 24
QVQLVQSGAE VKKPGASVKV SCKASGYTFT NHYMHWVRQA PGQGLEWMGI INPISGSTSN  60
AQKFQGRVTM TRDTSTSTVY MELSSLRSED TAVYYCARDI VDAFHFWGQG TMVTVSS      117

SEQ ID NO: 25              moltype = AA   length = 117
FEATURE                    Location/Qualifiers
REGION                     1..117
                           note = description of the artificial sequence: the amino
                            acid sequenceof D105I antibody VH
source                     1..117
                           mol_type = protein
                           organism = synthetic construct
SEQUENCE: 25
QVQLVQSGAE VKKPGASVKV SCKASGYTFT NHYMHWVRQA PGQGLEWMGI INPISGSTSN  60
AQKFQGRVTM TRDTSTSTVY MELSSLRSED TAVYYCARDI VDAFIFWGQG TMVTVSS      117

SEQ ID NO: 26              moltype = AA   length = 117
FEATURE                    Location/Qualifiers
REGION                     1..117
                           note = description of the artificial sequence: the amino
                            acid sequenceof D105K antibody VH
source                     1..117
                           mol_type = protein
                           organism = synthetic construct
SEQUENCE: 26
QVQLVQSGAE VKKPGASVKV SCKASGYTFT NHYMHWVRQA PGQGLEWMGI INPISGSTSN  60
AQKFQGRVTM TRDTSTSTVY MELSSLRSED TAVYYCARDI VDAFKFWGQG TMVTVSS      117

SEQ ID NO: 27              moltype = AA   length = 117
FEATURE                    Location/Qualifiers
REGION                     1..117
                           note = description of the artificial sequence: the amino
                            acid sequenceof D105L antibody VH
source                     1..117
                           mol_type = protein
                           organism = synthetic construct
SEQUENCE: 27
QVQLVQSGAE VKKPGASVKV SCKASGYTFT NHYMHWVRQA PGQGLEWMGI INPISGSTSN  60
AQKFQGRVTM TRDTSTSTVY MELSSLRSED TAVYYCARDI VDAFLFWGQG TMVTVSS      117

SEQ ID NO: 28              moltype = AA   length = 117
FEATURE                    Location/Qualifiers
REGION                     1..117
                           note = description of the artificial sequence: the amino
                            acid sequenceof D105M antibody VH
source                     1..117
```

```
                        mol_type = protein
                        organism = synthetic construct
SEQUENCE: 28
QVQLVQSGAE VKKPGASVKV SCKASGYTFT NHYMHWVRQA PGQGLEWMGI INPISGSTSN    60
AQKFQGRVTM TRDTSTSTVY MELSSLRSED TAVYYCARDI VDAFMFWGQG TMVTVSS       117

SEQ ID NO: 29           moltype = AA   length = 117
FEATURE                 Location/Qualifiers
REGION                  1..117
                        note = description of the artificial sequence: the amino
                         acid sequenceof D105P antibody VH
source                  1..117
                        mol_type = protein
                        organism = synthetic construct
SEQUENCE: 29
QVQLVQSGAE VKKPGASVKV SCKASGYTFT NHYMHWVRQA PGQGLEWMGI INPISGSTSN    60
AQKFQGRVTM TRDTSTSTVY MELSSLRSED TAVYYCARDI VDAFPFWGQG TMVTVSS       117

SEQ ID NO: 30           moltype = AA   length = 117
FEATURE                 Location/Qualifiers
REGION                  1..117
                        note = description of the artificial sequence: the amino
                         acid sequenceof D105Q antibody VH
source                  1..117
                        mol_type = protein
                        organism = synthetic construct
SEQUENCE: 30
QVQLVQSGAE VKKPGASVKV SCKASGYTFT NHYMHWVRQA PGQGLEWMGI INPISGSTSN    60
AQKFQGRVTM TRDTSTSTVY MELSSLRSED TAVYYCARDI VDAFQFWGQG TMVTVSS       117

SEQ ID NO: 31           moltype = AA   length = 117
FEATURE                 Location/Qualifiers
REGION                  1..117
                        note = description of the artificial sequence: the amino
                         acid sequenceof D105R antibody VH
source                  1..117
                        mol_type = protein
                        organism = synthetic construct
SEQUENCE: 31
QVQLVQSGAE VKKPGASVKV SCKASGYTFT NHYMHWVRQA PGQGLEWMGI INPISGSTSN    60
AQKFQGRVTM TRDTSTSTVY MELSSLRSED TAVYYCARDI VDAFRFWGQG TMVTVSS       117

SEQ ID NO: 32           moltype = AA   length = 117
FEATURE                 Location/Qualifiers
REGION                  1..117
                        note = description of the artificial sequence: the amino
                         acid sequenceof D105V antibody VH
source                  1..117
                        mol_type = protein
                        organism = synthetic construct
SEQUENCE: 32
QVQLVQSGAE VKKPGASVKV SCKASGYTFT NHYMHWVRQA PGQGLEWMGI INPISGSTSN    60
AQKFQGRVTM TRDTSTSTVY MELSSLRSED TAVYYCARDI VDAFVFWGQG TMVTVSS       117

SEQ ID NO: 33           moltype = AA   length = 117
FEATURE                 Location/Qualifiers
REGION                  1..117
                        note = description of the artificial sequence: the amino
                         acid sequenceof D105W antibody VH
source                  1..117
                        mol_type = protein
                        organism = synthetic construct
SEQUENCE: 33
QVQLVQSGAE VKKPGASVKV SCKASGYTFT NHYMHWVRQA PGQGLEWMGI INPISGSTSN    60
AQKFQGRVTM TRDTSTSTVY MELSSLRSED TAVYYCARDI VDAFWFWGQG TMVTVSS       117

SEQ ID NO: 34           moltype = AA   length = 117
FEATURE                 Location/Qualifiers
REGION                  1..117
                        note = description of the artificial sequence: the amino
                         acid sequenceof D105Y antibody VH
source                  1..117
                        mol_type = protein
                        organism = synthetic construct
SEQUENCE: 34
QVQLVQSGAE VKKPGASVKV SCKASGYTFT NHYMHWVRQA PGQGLEWMGI INPISGSTSN    60
AQKFQGRVTM TRDTSTSTVY MELSSLRSED TAVYYCARDI VDAFYFWGQG TMVTVSS       117

SEQ ID NO: 35           moltype = AA   length = 117
```

```
FEATURE               Location/Qualifiers
REGION                1..117
                      note = description of the artificial sequence: the amino
                       acid sequenceof D105T antibody VH
source                1..117
                      mol_type = protein
                      organism = synthetic construct
SEQUENCE: 35
QVQLVQSGAE VKKPGASVKV SCKASGYTFT NHYMHWVRQA PGQGLEWMGI INPISGSTSN   60
AQKFQGRVTM TRDTSTSTVY MELSSLRSED TAVYYCARDI VDAFTFWGQG TMVTVSS      117

SEQ ID NO: 36         moltype = AA  length = 117
FEATURE               Location/Qualifiers
REGION                1..117
                      note = description of the artificial sequence: the amino
                       acid sequenceof D105N antibody VH
source                1..117
                      mol_type = protein
                      organism = synthetic construct
SEQUENCE: 36
QVQLVQSGAE VKKPGASVKV SCKASGYTFT NHYMHWVRQA PGQGLEWMGI INPISGSTSN   60
AQKFQGRVTM TRDTSTSTVY MELSSLRSED TAVYYCARDI VDAFNFWGQG TMVTVSS      117

SEQ ID NO: 37         moltype = AA  length = 117
FEATURE               Location/Qualifiers
REGION                1..117
                      note = description of the artificial sequence: the amino
                       acid sequenceof D105Santibody VH
source                1..117
                      mol_type = protein
                      organism = synthetic construct
SEQUENCE: 37
QVQLVQSGAE VKKPGASVKV SCKASGYTFT NHYMHWVRQA PGQGLEWMGI INPISGSTSN   60
AQKFQGRVTM TRDTSTSTVY MELSSLRSED TAVYYCARDI VDAFSFWGQG TMVTVSS      117

SEQ ID NO: 38         moltype = AA  length = 117
FEATURE               Location/Qualifiers
REGION                1..117
                      note = description of the artificial sequence: the amino
                       acid sequenceof H2B11_A
source                1..117
                      mol_type = protein
                      organism = synthetic construct
SEQUENCE: 38
QVQLVQSGAE VKKPGASVKV SCKASGYTFT NHYMHWVRQA PGQGLEWMGI VNPFWGRWSN   60
AQKFQGRVTM TRDTSTSTVY MELSSLRSED TAVYYCARDA VDAFDFWGQG TMVTVSS      117

SEQ ID NO: 39         moltype = AA  length = 117
FEATURE               Location/Qualifiers
REGION                1..117
                      note = description of the artificial sequence: the amino
                       acid sequenceof J2H2B9_A
source                1..117
                      mol_type = protein
                      organism = synthetic construct
SEQUENCE: 39
QVQLVQSGAE VKKPGASVKV SCKASGYTFT NHYMHWVRQA PGQGLEWMGL INPWHGTFSN   60
AQKFQGRVTM TRDTSTSTVY MELSSLRSED TAVYYCARDA VDAFDFWGQG TMVTVSS      117

SEQ ID NO: 40         moltype = AA  length = 117
FEATURE               Location/Qualifiers
REGION                1..117
                      note = description of the artificial sequence: the amino
                       acid sequenceof J2H2E9_A
source                1..117
                      mol_type = protein
                      organism = synthetic construct
SEQUENCE: 40
QVQLVQSGAE VKKPGASVKV SCKASGYTFT NHYMHWVRQA PGQGLEWMGV INPFCGFVSN   60
AQKFQGRVTM TRDTSTSTVY MELSSLRSED TAVYYCARDA VDAFDFWGQG TMVTVSS      117

SEQ ID NO: 41         moltype = AA  length = 117
FEATURE               Location/Qualifiers
REGION                1..117
                      note = description of the artificial sequence: the amino
                       acid sequenceof 2H2E1_A
source                1..117
                      mol_type = protein
                      organism = synthetic construct
```

```
SEQUENCE: 41
QVQLVQSGAE VKKPGASVKV SCKASGYTFT NHYMHWVRQA PGQGLEWMGI LNPWTGYRSN     60
AQKFQGRVTM TRDTSTSTVY MELSSLRSED TAVYYCARDA VDAFDFWGQG TMVTVSS       117

SEQ ID NO: 42          moltype = AA   length = 117
FEATURE                Location/Qualifiers
REGION                 1..117
                       note = description of the artificial sequence: the amino
                        acid sequenceof 2H2E5_A
source                 1..117
                       mol_type = protein
                       organism = synthetic construct
SEQUENCE: 42
QVQLVQSGAE VKKPGASVKV SCKASGYTFT NHYMHWVRQA PGQGLEWMGI INPWVGRASN     60
AQKFQGRVTM TRDTSTSTVY MELSSLRSED TAVYYCARDA VDAFDFWGQG TMVTVSS       117

SEQ ID NO: 43          moltype = AA   length = 117
FEATURE                Location/Qualifiers
REGION                 1..117
                       note = description of the artificial sequence: the amino
                        acid sequenceof 2H2E8_Y
source                 1..117
                       mol_type = protein
                       organism = synthetic construct
SEQUENCE: 43
QVQLVQSGAE VKKPGASVKV SCKASGYTFT NHYMHWVRQA PGQGLEWMGI VNPYRGKWSN     60
AQKFQGRVTM TRDTSTSTVY MELSSLRSED TAVYYCARDY VDAFDFWGQG TMVTVSS       117

SEQ ID NO: 44          moltype = AA   length = 106
FEATURE                Location/Qualifiers
REGION                 1..106
                       note = description of the artificial sequence: the amino
                        acid sequenceof L3G12
source                 1..106
                       mol_type = protein
                       organism = synthetic construct
SEQUENCE: 44
AIQLTQSPSS LSASVGDRVT ITCRASQGIS SALVWYQQKP GKAPKLLIYD ASSLESGVPS     60
RFSGSGSGTD FTLTISSLQP EDFATYYCQQ MYDDFNFGPG TKVDIK                  106

SEQ ID NO: 45          moltype = AA   length = 106
FEATURE                Location/Qualifiers
REGION                 1..106
                       note = description of the artificial sequence: the amino
                        acid sequenceof L1H8
source                 1..106
                       mol_type = protein
                       organism = synthetic construct
SEQUENCE: 45
AIQLTQSPSS LSASVGDRVT ITCRASQDVS TALLWYQQKP GKAPKLLIYD ASSLESGVPS     60
RFSGSGSGTD FTLTISSLQP EDFATYYCQQ FNDYFTFGPG TKVDIK                  106

SEQ ID NO: 46          moltype = AA   length = 106
FEATURE                Location/Qualifiers
REGION                 1..106
                       note = description of the artificial sequence: the amino
                        acid sequenceof 2L3H7
source                 1..106
                       mol_type = protein
                       organism = synthetic construct
SEQUENCE: 46
AIQLTQSPSS LSASVGDRVT ITCRASQGIS SALVWYQQKP GKAPKLLIYD ASSLESGVPS     60
RFSGSGSGTD FTLTISSLQP EDFATYYCQQ LYDDFDFGPG TKVDIK                  106

SEQ ID NO: 47          moltype = AA   length = 117
FEATURE                Location/Qualifiers
REGION                 1..117
                       note = description of the artificial sequence: the amino
                        acid sequenceof J2H2B9_Y
source                 1..117
                       mol_type = protein
                       organism = synthetic construct
SEQUENCE: 47
QVQLVQSGAE VKKPGASVKV SCKASGYTFT NHYMHWVRQA PGQGLEWMGL INPWHGTFSN     60
AQKFQGRVTM TRDTSTSTVY MELSSLRSED TAVYYCARDY VDAFDFWGQG TMVTVSS       117

SEQ ID NO: 48          moltype = AA   length = 330
FEATURE                Location/Qualifiers
REGION                 1..330
```

```
                          note = description of the artificial sequence: the amino
                            acid sequenceof YTE CH
source                    1..330
                          mol_type = protein
                          organism = synthetic construct
SEQUENCE: 48
ASTKGPSVFP LAPSSKSTSG GTAALGCLVK DYFPEPVTVS WNSGALTSGV HTFPAVLQSS   60
GLYSLSSVVT VPSSSLGTQT YICNVNHKPS NTKVDKKVEP KSCDKTHTCP PCPAPELLGG   120
PSVFLFPPKP KDTLYITREP EVTCVVVDVS HEDPEVKFNW YVDGVEVHNA KTKPREEQYN   180
STYRVVSVLT VLHQDWLNGK EYKCKVSNKA LPAPIEKTIS KAKGQPREPQ VYTLPPSRDE   240
LTKNQVSLTC LVKGFYPSDI AVEWESNGQP ENNYKTTPPV LDSDGSFFLY SKLTVDKSRW   300
QQGNVFSCSV MHEALHNHYT QKSLSLSPGK                                    330

SEQ ID NO: 49            moltype = AA  length = 326
FEATURE                  Location/Qualifiers
REGION                   1..326
                         note = description of the artificial sequence: the amino
                           acid sequenceof G2_YTE CH
source                   1..326
                         mol_type = protein
                         organism = synthetic construct
SEQUENCE: 49
ASTKGPSVFP LAPCSRSTSE STAALGCLVK DYFPEPVTVS WNSGALTSGV HTFPAVLQSS   60
GLYSLSSVVT VPSSNFGTQT YTCNVDHKPS NTKVDKTVER KCCVECPPCP APPVAGPSVF   120
LFPPKPKDTL YITREPEVTC VVVDVSHEDP EVQFNWYVDG VEVHNAKTKP REEQFNSTFR   180
VVSVLTVVHQ DWLNGKEYKC KVSNKGLPAP IEKTISKTKG QPREPQVYTL PPSREEMTKN   240
QVSLTCLVKG FYPSDIAVEW ESNGQPENNY KTTPPMLDSD GSFFLYSKLT VDKSRWQQGN   300
VFSCSVMHEA LHNHYTQKSL SLSPGK                                        326

SEQ ID NO: 50            moltype = AA  length = 326
FEATURE                  Location/Qualifiers
REGION                   1..326
                         note = description of the artificial sequence: the amino
                           acid sequenceof G2_LS CH
source                   1..326
                         mol_type = protein
                         organism = synthetic construct
SEQUENCE: 50
ASTKGPSVFP LAPCSRSTSE STAALGCLVK DYFPEPVTVS WNSGALTSGV HTFPAVLQSS   60
GLYSLSSVVT VPSSNFGTQT YTCNVDHKPS NTKVDKTVER KCCVECPPCP APPVAGPSVF   120
LFPPKPKDTL MISRTPEVTC VVVDVSHEDP EVQFNWYVDG VEVHNAKTKP REEQFNSTFR   180
VVSVLTVVHQ DWLNGKEYKC KVSNKGLPAP IEKTISKTKG QPREPQVYTL PPSREEMTKN   240
QVSLTCLVKG FYPSDIAVEW ESNGQPENNY KTTPPMLDSD GSFFLYSKLT VDKSRWQQGN   300
VFSCSVLHEA LHSHYTQKSL SLSPGK                                        326

SEQ ID NO: 51            moltype = AA  length = 327
FEATURE                  Location/Qualifiers
REGION                   1..327
                         note = description of the artificial sequence: the amino
                           acid sequenceof G4PE_R409K_P CH
source                   1..327
                         mol_type = protein
                         organism = synthetic construct
SEQUENCE: 51
ASTKGPSVFP LAPCSRSTSE STAALGCLVK DYFPEPVTVS WNSGALTSGV HTFPAVLQSS   60
GLYSLSSVVT VPSSSLGTKT YTCNVDHKPS NTKVDKRVES KYGPPCPPCP APEFEGGPSV   120
FLFPPKPKDT LMISRTPEVT CVVVDVSQED PEVQFNWYVD GVEVHNAKTK PREEQFNSTY   180
RVVSVLTPLH QDWLNGKEYK CKVSNKGLPS SIEKTISKAK GQPREPQVYT LPPSQEEMTK   240
NQVSLTCLVK GFYPSDIAVE WESNGQPENN YKTTPPVLDS DGSFFLYSKL TVDKSRWQEG   300
NVFSCSVMHE ALHNHYTQKS LSLSLGK                                       327

SEQ ID NO: 52            moltype = AA  length = 327
FEATURE                  Location/Qualifiers
REGION                   1..327
                         note = description of the artificial sequence: the amino
                           acid sequenceof G4PE_R409K_LS CH
source                   1..327
                         mol_type = protein
                         organism = synthetic construct
SEQUENCE: 52
ASTKGPSVFP LAPCSRSTSE STAALGCLVK DYFPEPVTVS WNSGALTSGV HTFPAVLQSS   60
GLYSLSSVVT VPSSSLGTKT YTCNVDHKPS NTKVDKRVES KYGPPCPPCP APEFEGGPSV   120
FLFPPKPKDT LMISRTPEVT CVVVDVSQED PEVQFNWYVD GVEVHNAKTK PREEQFNSTY   180
RVVSVLTVLH QDWLNGKEYK CKVSNKGLPS SIEKTISKAK GQPREPQVYT LPPSQEEMTK   240
NQVSLTCLVK GFYPSDIAVE WESNGQPENN YKTTPPVLDS DGSFFLYSKL TVDKSRWQEG   300
NVFSCSVLHE ALHSHYTQKS LSLSLGK                                       327

SEQ ID NO: 53            moltype = AA  length = 330
FEATURE                  Location/Qualifiers
```

-continued

```
REGION                  1..330
                        note = description of the artificial sequence: the amino
                         acid sequenceof G1 constant region
source                  1..330
                        mol_type = protein
                        organism = synthetic construct
SEQUENCE: 53
ASTKGPSVFP LAPSSKSTSG GTAALGCLVK DYFPEPVTVS WNSGALTSGV HTFPAVLQSS  60
GLYSLSSVVT VPSSSLGTQT YICNVNHKPS NTKVDKKVEP KSCDKTHTCP PCPAPELLGG  120
PSVFLFPPKP KDTLMISRTP EVTCVVVDVS HEDPEVKFNW YVDGVEVHNA KTKPREEQYN  180
STYRVVSVLT VLHQDWLNGK EYKCKVSNKA LPAPIEKTIS KAKGQPREPQ VYTLPPSRDE  240
LTKNQVSLTC LVKGFYPSDI AVEWESNGQP ENNYKTTPPV LDSDGSFFLY SKLTVDKSRW  300
QQGNVFSCSV MHEALHNHYT QKSLSLSPGK                                    330

SEQ ID NO: 54           moltype = AA  length = 303
FEATURE                 Location/Qualifiers
REGION                  1..303
                        note = description of the artificial sequence: the amino
                         acid sequenceof Homo sapiens FcRn extracellular domain
                         His-tag form
source                  1..303
                        mol_type = protein
                        organism = synthetic construct
SEQUENCE: 54
MGVPRPQPWA LGLLLFLLPG SLGAESHLSL LYHLTAVSSP APGTPAFWVS GWLGPQQYLS  60
YNSLRGEAEP CGAWVWENQV SWYWEKETTD LRIKEKLFLE AFKALGGKGP YTLQGLLGCE  120
LGPDNTSVPT AKFALNGEEF MNFDLKQGTW GGDWPEALAI SQRWQQQDKA ANKELTFLLF  180
SCPHRLREHL ERGRGNLEWK EPPSMRLKAR PSSPGFSVLT CSAFSFYPPE LQLRFLRNGL  240
AAGTGQGDFG PNSDGSFHAS SSLTVKSGDE HHYCCIVQHA GLAQPLRVEL ESPAKSSHHH  300
HHH                                                                303

SEQ ID NO: 55           moltype = AA  length = 119
FEATURE                 Location/Qualifiers
source                  1..119
                        mol_type = protein
                        organism = Homo sapiens
SEQUENCE: 55
MSRSVALAVL ALLSLSGLEA IQRTPKIQVY SRHPAENGKS NFLNCYVSGF HPSDIEVDLL  60
KNGERIEKVE HSDLSFSKDW SFYLLYYTEF TPTEKDEYAC RVNHVTLSQP KIVKWDRDM   119

SEQ ID NO: 56           moltype = AA  length = 303
FEATURE                 Location/Qualifiers
REGION                  1..303
                        note = description of the artificial sequence: the amino
                         acid sequenceof Primates FcRn extracellular domain His-tag
                         form
source                  1..303
                        mol_type = protein
                        organism = synthetic construct
SEQUENCE: 56
MRVPRPQPWA LGLLLFLLPG SLGAESHLSL LYHLTAVSSP APGTPAFWVS GWLGPQQYLS  60
YDSLRGQAEP CGAWVWENQV SWYWEKETTD LRIKEKLFLE AFKALGGKGP YTLQGLLGCE  120
LSPDNTSVPT AKFALNGEEF MNFDLKQGTW GGDWPEALAI SQRWQQQDKA ANKELTFLLF  180
SCPHRLREHL ERGRGNLEWK EPPSMRLKAR PGNPGFSVLT CSAFSFYPPE LQLRFLRNGM  240
AAGTGQGDFG PNSDGSFHAS SSLTVKSGDE HHYCCIVQHA GLAQPLRVEL ETPAKSSHHH  300
HHH                                                                303

SEQ ID NO: 57           moltype = AA  length = 119
FEATURE                 Location/Qualifiers
source                  1..119
                        mol_type = protein
                        organism = Macaca fascicularis
SEQUENCE: 57
MSPSVALAVL ALLSPSGLEA IQRTPKIQVY SRHPPENGKP NFLNCYVSGF HPSDIEVDLL  60
KNGEKMGKVE HSDLSFSKDW SFYLLYYTEF TPNEKDEYAC RVNHVTLSGP RTVKWDRDM   119

SEQ ID NO: 58           moltype = AA  length = 106
FEATURE                 Location/Qualifiers
source                  1..106
                        mol_type = protein
                        organism = synthetic construct
REGION                  1..106
                        note = description of the artificial sequence: the amino
                         acid sequence of A-9 antibody VL
SEQUENCE: 58
AIQLTQSPSS LSASVGDRVT ITCRASQGIS SALVWYQQKP GKAPKLLIYD ASSLESGVPS  60
RFSGSGSGTD FTLTISSLQP EDFATYYCQQ FWDDFDFGPG TKVDIK                 106

SEQ ID NO: 59           moltype = AA  length = 106
```

-continued

```
FEATURE          Location/Qualifiers
source           1..106
                 mol_type = protein
                 organism = synthetic construct
REGION           1..106
                 note = description of the artificial sequence: the amino
                  acid sequence of A-10 antibody VL
SEQUENCE: 59
AIQLTQSPSS LSASVGDRVT ITCRASQGIS SALVWYQQKP GKAPKLLIYD ASSLESGVPS  60
RFSGSGSGTD FTLTISSLQP EDFATYYCQQ FYDDFDFGPG TKVDIK                106
```

ANTI-FGF23 ANTIBODY OR ANTIBODY FRAGMENT THEREOF

SEQUENCE LISTING

A sequence listing in electronic (XML file) format is filed with this application and incorporated herein by reference. The name of the XML file is "Sequence_Listing_Revised-0948A.xml"; the file was created on Feb. 7, 2025; the size of the file is 85,275 bytes.

TECHNICAL FIELD

The present invention relates to an anti-FGF23 antibody or an antibody fragment thereof.

BACKGROUND ART

Fibroblast growth factors (hereinafter, referred to as "FGF") form a family of structurally similar polypeptides, and have been reported to have various effects, including not only fibroblast proliferation activity but also proliferation of mesoderm and neuroectoderm, angiogenesis, and limb bud formation during development. In adults, the fibroblast growth factors also function as a homeostatic factor for tissue maintenance, repair, regeneration, metabolism, and the like (Non Patent Literature 1).

In mammals, 22 types of proteins are known to belong to the FGF family. In humans, 22 types of FGFs, FGF1 to FGF23, excluding FGF15, have been identified. The human FGF family is composed of about 150 to 300 amino acids, and about 120 amino acids in the core sequence are identical at a rate of about 30% to 60%. The FGF family is classified into a family expressed as a secretory protein and acting on a receptor tyrosine kinase, and a family expressed as an intracellular protein and acting on a potential-dependent sodium channel or other molecules (Non Patent Literature 2).

FGF23 is a secretory protein identified from mice by using a database search and a PCR method utilizing homology with FGF15 and subsequently identified by a homology search. There has been known that human FGF23 is composed of a polypeptide having 251 amino acid residues, with 24 residues at the N-terminal functioning as a secretory signal and being cleaved in the maturation process of a protein (Non Patent Literature 3).

Hypophosphatemic diseases caused by excessive production of FGF23 are known, and are broadly classified into diseases with identified causative genes and acquired diseases (Non Patent Literature 4). Among FGF23-related hypophosphatemic diseases with identified causative genes, the most frequent one is X-linked hypophosphatemic rickets (hereinafter, referred to as XLH) caused by phosphate-regulating endopeptidase homolog, X-linked (PHEX) mutations, and many PHEX gene mutations have been reported to date (Non Patent Literature 5).

There has been known that PHEX is a single-pass membrane protein, and is expressed in large amounts in cartilage, bone blasts, and dentin blasts (Non Patent Literatures 6 and 7), and XLH is said to develop in 20000 people at a frequency of one person (Non Patent Literature 8). An example of the acquired disease is tumor-induced osteomalacia (TIO).

In related art, active vitamin D3 preparations and oral phosphorus preparations have been used as symptomatic treatments for these FGF23-related hypophosphatemic diseases. However, long-term administration may cause complications such as hypercalcemia and urinaria, nephrocalcinosis, persistent hyperparathyroidism (Non Patent Literatures 9 and 10).

Burosumab, an FGF23 neutralizing antibody, is known as a therapeutic agent for the above-described diseases considered to be caused by excessive production of FGF23.

There also has been known an antibody described in Patent Literature 1 as a human FGF23 neutralizing antibody.

CITATION LIST

Patent Literature

Patent Literature 1: WO2008/099969

Non-Patent Literature

Non Patent Literature 1: Wiley Interdiscip Rev Dev Biol. 2015 May-June; 4(3): 215-66
Non Patent Literature 2: J Biochem. 2011 February; 149(2): 121-30
Non Patent Literature 3: Biochem Biophys Res Commun. 2000 Oct. 22; 277(2): 494-8
Non Patent Literature 4: Endocrinology. 2011 January; 152(1): 4-10
Non Patent Literature 5: Hum Mutat. 2000; 16(1): 1-6.
Non Patent Literature 6: J Clin Invest. 2008 Feb. 1; 118(2): 722-734
Non Patent Literature 7: J Clin Invest. 1997 Mar. 15; 99(6): 1200-1209.
Non Patent Literature 8: Orphanet J Rare Dis. 2019; 14:58
Non Patent Literature 9: Lancet. 2019 Jun. 15; 393(10189): 2416-2427
Non Patent Literature 10: J Bone Miner Res. 2011 July; 26(7): 1381-8

SUMMARY OF INVENTION

Technical Problem

As a result of intensive studies on physical properties of the anti-human FGF23 antibody described in WO2008/099969, the present inventors have found that the antibody decreases in stability and is degraded at a low pH, and that the degradation is caused by cleavage between D at position 99 and I at position 100 in the amino acid sequence of a heavy chain variable region of the antibody. Generally, there has been known that antibodies are prone to aggregation when concentrating an antibody formulation, and when an absolute value of the charge of proteins in a protein solution is increased, the possibility of the aggregation of the proteins can be reduced (Arch Pharm Res Vol 35, No 11, 1871-1886, 2012). Therefore, when concentrating an antibody formulation, one method for suppressing antibody aggregation is to lower the pH of the formulation. Accordingly, when it is necessary to lower the pH of an antibody formulation, an antibody that can be tested over a wide pH range is more desirable.

Therefore, an object of the present invention is to provide a novel anti-FGF23 antibody in which antibody degradation at a lower pH is suppressed as compared with the anti-human FGF23 antibody described in WO2008/099969.

Solution to Problem

As a result of intensive studies on the above problems, the present inventors have found that the above problems can be solved by an anti-FGF23 antibody in which the amino acid residue at position 100 or the amino acid residue at position 105 in a VH of the anti-FGF23 antibody described in WO2008/099969 is substituted, and have completed the present invention.

1. An antibody or an antibody fragment thereof which binds to FGF23, in which the antibody comprises a heavy chain variable region (hereinafter, described as VH) comprising the amino acid sequence represented by SEQ ID NO: 1 and a light chain variable region (hereinafter, described as VL) comprising the amino acid sequence represented by SEQ ID NO: 2, and in which at least the amino acid residue at position 100 or the amino acid residue at position 105 of the amino acid sequence represented by SEQ ID NO: 1 in the VH is substituted with another amino acid residue.

2. The antibody or the antibody fragment thereof according to the above 1, in which the amino acid residue at position 100 of the amino acid sequence represented by SEQ ID NO: 1 in the VH is substituted with one amino acid residue selected from alanine residue, asparagine residue, glycine residue, tyrosine residue, arginine residue, aspartic acid residue, histidine residue, tryptophan residue, and methionine residue.

3. The antibody or the antibody fragment thereof according to the above 1 or 2, in which the amino acid residue at position 100 of the amino acid sequence represented by SEQ ID NO: 1 in the VH is substituted with alanine residue or tyrosine residue.

4. The antibody or the antibody fragment thereof according to any one of the above 1 to 3, in which the amino acid residue at position 105 of the amino acid sequence represented by SEQ ID NO: 1 in the VH is substituted with one amino acid residue selected from alanine residue, phenylalanine residue, glycine residue, histidine residue, isoleucine residue, lysine residue, leucine residue, methionine residue, proline residue, glutamine residue, arginine residue, valine residue, tryptophan residue, tyrosine residue, threonine residue, asparagine residue, and serine residue.

5. The antibody or the antibody fragment thereof according to any one of the above 1 to 4, in which the antibody further comprises one substitution selected from the following (a1) to (a4):

(a1) at least one substitution selected from substitution of the amino acid residue at position 50 with leucine residue, substitution of the amino acid residue at position 54 with tryptophan residue, substitution of the amino acid residue at position 55 with histidine residue, substitution of the amino acid residue at position 57 with threonine residue, and substitution of the amino acid residue at position 58 with phenylalanine residue in the amino acid sequence represented by SEQ ID NO: 1 in the VH, (a2) at least one substitution selected from substitution of the amino acid residue at position 91 with methionine residue or leucine residue, substitution of the amino acid residue at position 92 with tyrosine residue, substitution of the amino acid residue at position 94 with aspartic acid residue, and substitution of the amino acid residue at position 96 with asparagine residue or aspartic acid residue in the amino acid sequence represented by SEQ ID NO: 2 in the VL, (a3) at least one substitution selected from substitution of the amino acid residue at position 28 with aspartic acid residue, substitution of the amino acid residue at position 29 with valine residue, substitution of the amino acid residue at position 31 with threonine residue, and substitution of the amino acid residue at position 34 with leucine residue in the amino acid sequence represented by SEQ ID NO: 2 in the VL, and (a4) at least one substitution selected from substitution of the amino acid residue at position 92 with tyrosine residue or tryptophan residue, substitution of the amino acid residue at position 94 with aspartic acid residue, and substitution of the amino acid residue at position 96 with aspartic acid residue in the amino acid sequence represented by SEQ ID NO: 2 in the VL.

6. The antibody or the antibody fragment thereof according to any one of the above 1 to 5, in which the antibody is one selected from the following (c1) to (c10):

(c1) an antibody comprising a VH comprising the amino acid sequence represented by SEQ ID NO: 39 and a VL comprising the amino acid sequence represented by SEQ ID NO: 2, (c2) an antibody comprising a VH comprising the amino acid sequence represented by SEQ ID NO: 47 and a VL comprising the amino acid sequence represented by SEQ ID NO: 2, (c3) an antibody comprising a VH comprising the amino acid sequence represented by SEQ ID NO: 3 and a VL comprising the amino acid sequence represented by SEQ ID NO: 44, (c4) an antibody comprising a VH comprising the amino acid sequence represented by SEQ ID NO: 6 and a VL comprising the amino acid sequence represented by SEQ ID NO: 44, (c5) an antibody comprising a VH comprising the amino acid sequence represented 25 by SEQ ID NO: 3 and a VL comprising the amino acid sequence represented by SEQ ID NO: 45, (c6) an antibody comprising a VH comprising the amino acid sequence represented by SEQ ID NO: 6 and a VL comprising the amino acid sequence represented by SEQ ID NO: 45, (c7) an antibody comprising a VH comprising the amino acid sequence represented by SEQ ID NO: 3 and a VL comprising the amino acid sequence represented by SEQ ID NO: 46, (c8) an antibody comprising a VH comprising the amino acid sequence represented by SEQ ID NO: 6 and a VL comprising the amino acid sequence represented by SEQ ID NO: 46, (c9) an antibody comprising a VH comprising the amino acid sequence represented by SEQ ID NO: 3 and a VL comprising the amino acid sequence represented by SEQ ID NO: 58, and (c10) an antibody comprising a VH comprising the amino acid sequence represented by SEQ ID NO: 6 and a VL comprising the amino acid sequence represented by SEQ ID NO: 59.

7. The antibody or the antibody fragment thereof according to any one of the above 1 to 6, in which a subclass of the antibody is IgG1, IgG2, IgG3 or IgG4.

8. The antibody or the antibody fragment thereof according to any one of the above 1 to 7, in which an Fc region of the antibody is one selected from the following (d1) to (d5):

(d1) an Fc region comprising substitution of the amino acid residue at position 252 with tyrosine residue, substitution of the amino acid residue at position 254 with threonine residue, and substitution of the amino acid residue at position 256 with glutamic acid residue according to the EU index,

(d2) an Fc region comprising substitution of the amino acid residue at position 428 with leucine residue, and substitution of the amino acid residue at position 434 with serine residue according to the EU index, (d3) an Fc region comprising substitution of the amino acid residue at position 308 with proline residue according to the EU index, (d4) an Fc region comprising substitution of the amino acid residue at position 250 with glutamine residue, and substitution of the amino acid residue at position 428 with leucine residue according to the EU index, and (d5) an Fc region comprising substitution of the amino acid residue at position 434 with alanine residue according to the EU index.

9. The antibody or the antibody fragment thereof according to any one of the above 1 to 8, in which a heavy chain constant region of the antibody comprises the amino acid sequence represented by SEQ ID NO: 48, 49, 50, 51 or 52.

10. The antibody or the antibody fragment thereof according to any one of the above 1 to 9, in which the antibody fragment is one selected from Fab, Fab', (Fab')₂, scFv, diabody, dsFv, and a peptide comprising CDR.

11. A nucleic acid comprising a nucleotide sequence that encodes the antibody or the antibody fragment thereof according to any one of the above 1 to 10.

12. A vector comprising the nucleic acid according to the above 11.

13. A transformant cell comprising the vector according to the above 12.

14. A method for producing the antibody or the antibody fragment thereof according to any one of the above 1 to 10, including:

culturing the transformant cell according to the above 13 in a medium, and collecting the antibody or the antibody fragment thereof from a culture.

15. A composition containing:

the antibody or the antibody fragment thereof according to any one of the above 1 to 10.

16. A therapeutic agent for a disease associated with human FGF23, containing: the antibody or the antibody fragment thereof according to any one of the above 1 to 10.

17. A therapeutic method for a disease associated with human FGF23, including: the antibody or the antibody fragment thereof according to any one of the above 1 to 10.

Advantageous Effects of Invention

The anti-FGF23 antibody of the present invention can be suppressed from degrading and exhibits excellent stability at a low pH as compared with the anti-FGF23 antibody described in WO2008/099969. According to the present invention, an anti-FGF23 antibody or an antibody fragment thereof, a nucleic acid comprising a nucleotide sequence that encodes the antibody or the antibody fragment thereof, a vector comprising the nucleic acid, a transformant cell comprising the vector, a method for producing the antibody or the antibody fragment thereof, and a composition containing the antibody or the antibody fragment thereof can be provided.

DESCRIPTION OF EMBODIMENTS

The present invention relates to an antibody or an antibody fragment thereof which binds to fibroblast growth factor 23 (hereinafter, referred to as FGF23) described in WO2008/099969 (referred to as an antibody comprising a heavy chain variable region (hereinafter, described as VH) comprising the amino acid sequence represented by SEQ ID NO: 1 and a light chain variable region (hereinafter, described as VL) comprising the amino acid sequence represented by SEQ ID NO: 2), in which at least the amino acid residue at position 100 or the amino acid residue at position 105 of the amino acid sequence represented by SEQ ID NO: 1 in the VH is substituted with another amino acid residue (hereinafter, referred to as the antibody of the present invention).

"FGF23" is a type of fibroblast growth factor and a hormone derived from bone cells. Human FGF is a protein consisting of 251 amino acids comprising a secretory signal of 24 amino acids at the N-terminal, and the secretory signal is cleaved during the maturation process of the protein. Examples of the function of the FGF23 include suppression of reabsorption of phosphorus and activation of vitamin D in the kidney, mainly via an FGF receptor 1 (hereinafter, also referred to as FGFR1)/α-Klotho complex on renal proximal tubule cells in the kidney.

In the present invention, examples of the human FGF23 include a polypeptide comprising an amino acid sequence of NCBI Accession Number: NP_065689, a polypeptide consisting of an amino acid sequence in which one or more amino acids are deleted, substituted, or added in the amino acid sequence of NCBI Accession Number: NP_065689 and having a function of the human FGF23, and a polypeptide consisting of an amino acid sequence having a homology of 60% or more, preferably 80% or more, further preferably 90% or more, and most preferably 95% or more with the amino acid sequence of NCBI Accession Number: NP_065689 and having a function of the human FGF23.

The polypeptide comprising an amino acid sequence in which one or more amino acids are deleted, substituted, or added in the amino acid sequence represented by NCBI Accession Number: NP_065689 can be obtained by introducing a site-specific mutagenesis into a DNA encoding a polypeptide comprising the amino acid sequence represented by NCBI Accession Number: NP_065689, for example, using a site-specific mutagenesis method [Molecular Cloning, A Laboratory Manual, Second Edition, Cold Spring Harbor Laboratory Press (1989), Current Protocols in Molecular Biology, John Wiley & Sons (1987-1997), Nucleic acids Research, 10, 6487 (1982), Proc. Natl. Acad. Sci. USA, 79, 6409 (1982), Gene, 34, 315 (1985), Nucleic Acids Research, 13, 4431 (1985), Proc. Natl. Acad. Sci. USA, 82, 488 (1985)].

The number of amino acids to be deleted, substituted, or added is not particularly limited, and is preferably 1 to several tens of amino acids, for example 1 to 20 amino acids, and more preferably 1 to several amino acids, for example 1 to 5 amino acids.

Examples of a gene encoding the human FGF23 include the nucleotide sequence of NCBI Accession Number: NM_020638. The gene encoding the human FGF23 of the present invention also includes a gene comprising a DNA consisting of a nucleotide sequence in which one or more bases are deleted, substituted, or added in the nucleotide sequence of NM_020638 and encoding a polypeptide having the function of the human FGF23, a gene comprising a DNA consisting of a nucleotide sequence having at least 60% or more homology, preferably a nucleotide sequence having 80% or more homology, further preferably a nucleotide sequence having 90% or more homology, and most preferably a nucleotide sequence having 95% or more homology with the nucleotide sequence of NM_020638, and encoding a polypeptide having the function of human FGF23, or a gene consisting of a DNA that hybridizes under stringent conditions with a DNA comprising the nucleotide sequence of NM_020638 and encoding a polypeptide having the function of the human FGF23.

The DNA that hybridizes under stringent conditions refers to a hybridizable DNA obtained by a colony hybridization method, a plaque hybridization method, a Southern blot hybridization method, a DNA microarray method, or the like using a DNA comprising the nucleotide sequence of NM_020638 as a probe.

Specific examples thereof include a DNA that can be identified by performing hybridization [Molecular Cloning, A Laboratory Manual, Second Edition, Cold Spring Harbor Laboratory Press (1989), Current Protocols in Molecular Biology, John Wiley & Sons (1987-1997), DNA Cloning 1: Core Techniques, A Practical Approach, Second Edition, Oxford University (1995)] at 65° C. in the presence of 0.7 mol/L to 1.0 mol/L sodium chloride using a filter or a slide glass on which a DNA derived from a hybridized colony or plaque, or a PCR product or an oligo DNA having the sequence is immobilized, and then washing the filter or the slide glass under a condition of 65° C. using a 0.1× to 2×SSC solution (a composition of the 1×SSC solution consists of 150 mmol/L sodium chloride and 15 mmol/L sodium citrate).

Examples of the hybridizable DNA include a DNA having at least 60% or more homology, preferably a DNA having 80% or more homology, and further preferably a DNA having 95% or more homology with the nucleotide sequence of NM_020638.

Genetic polymorphisms are often observed in the nucleotide sequences of genes encoding eukaryotic proteins. The gene encoding the human FGF23 of the present invention also includes genes used in the present invention that have small-scale mutations in nucleotide sequences thereof due to such polymorphisms.

Unless otherwise specified, a numerical value of homology in the present invention may be a numerical value calculated using a homology search program known to those skilled in the art. Examples of the numerical value of homology for the nucleotide sequence include numerical values calculated using default parameters in BLAST [J. Mol. Biol., 215, 403 (1990)], and examples of the numerical value of homology for the amino acid sequence include numerical values calculated using default parameters in BLAST2 [Nucleic Acids Res., 25, 3389 (1997), Genome Res., 7, 649 (1997)].

As the default parameters, G (Cost to open gap) is 5 for nucleotide sequences and 11 for amino acid sequences, −E (Cost to extend gap) is 2 for nucleotide sequences and 1 for amino acid sequences, −q (Penalty for nucleotide mismatch) is −3, −r (reward for nucleotide match) is 1, −e (expect value) is 10, −W (wordsize) is 11 residues for nucleotide sequences and 3 residues for amino acid sequences, −y[Dropoff (X) for blast extensions in bits] is 20 for blastn and 7 for programs other than blastn, −X (X dropoff value for gapped alignment in bits) is 15, and −Z (final X dropoff value for gapped alignment in bits) is 50 for blastn and 25 for programs other than blastn.

The polypeptide comprising a partial sequence of the amino acid sequence of NCBI Accession Number: NP_065689 can be produced by a method known to those skilled in the art. Specifically, the polypeptide can be prepared by deleting a part of the DNA encoding the amino acid sequence of NP_065689 and culturing a transformant introduced with an expression vector comprising the DNA. By a method same as that described above, a polypeptide comprising an amino acid sequence in which one or more amino acids are deleted, substituted, or added in the amino acid sequence of NCBI Accession Number: NP_065689 can be obtained. Further, a polypeptide consisting of the amino acid sequence of NCBI Accession Number: NP_065689, or a polypeptide comprising an amino acid sequence in which one or more amino acids are deleted, substituted, or added in the amino acid sequence of NCBI Accession Number: NP_065689 can also be produced by chemical synthesis methods such as a fluorenylmethyloxycarbonyl (Fmoc) method and a t-butyloxycarbonyl (tBoc) method.

In the present invention, deletion, substitution, addition, and the like of amino acids are also referred to as amino acid modification.

The antibody of the present invention includes any of a polyclonal antibody, a monoclonal antibody, and an oligoclonal antibody. The polyclonal antibody refers to a population of antibody molecules secreted by antibody-producing cells of different clones. The monoclonal antibody is an antibody secreted by a single clone of an antibody-producing cell, which recognizes only one epitope (also called an antigen determinant) and has a uniform amino acid sequence (primary sequence) that constitutes the monoclonal antibody. The oligoclonal antibody refers to a population of antibody molecules that is a mixture of a plurality of different monoclonal antibodies.

The monoclonal antibody in the present invention may include an antibody produced by a hybridoma and a recombinant antibody produced by a transformant transformed with an expression vector comprising an antibody gene.

Examples of the epitope include a single amino acid sequence, a conformation composed of an amino acid sequence, an amino acid sequence modified by post-translational modification, and a conformation composed of the amino acid sequence, each of which the monoclonal antibody recognizes and binds to.

Examples of the amino acid sequence modified by post-translational modification include an amino acid sequence to which an O-linked glycan in which a glycan binds to Tyr and Ser each having an OH substituent, an N-linked glycan in which a glycan binds to Gln and Asn each having an $NH_2$ substituent, and a sulfate group in which a sulfuric acid molecule binds to Tyr and Ser having an OH substituent, or the like binds.

The binding of the antibody of the present invention to human FGF23 can be confirmed by measuring a binding ability of the antibody of the present invention to human FGF23 using ELISA, or a surface plasmon resonance method. Confirmation can also be performed in combination with a well-known immunological detection method [Monoclonal Antibodies-Principles and Practice, Third Edition, Academic Press (1996), Antibodies-A Laboratory Manual, Cold Spring Harbor Laboratory (1988), Monoclonal Antibody Laboratory Manual, Kodansha Scientific (1987)], and the like.

The amino acid residue or epitope of the human FGF23 to which the antibody of the present invention binds can be determined by performing an antibody binding experiment using a defect in which a part of a domain of the human FGF23 is deleted, a mutant substituted with a domain derived from another protein, a partial peptide fragment of the human FGF23, or the like.

The amino acid residue or epitope of the human FGF23 to which the antibody of the present invention binds can also be determined by adding the antibody of the present invention to a peptide fragment of the human FGF23 digested with a protease and performing epitope mapping using known mass spectrometry.

An antibody molecule is also referred to as an immunoglobulin (hereinafter, referred to as Ig), and the human antibody is classified into IgA1, IgA2, IgD, IgE, IgG1, IgG2, IgG3, IgG4, and IgM isotypes according to a difference in molecular structure. IgG1, IgG2, IgG3, and IgG4 having relatively high amino acid sequence homology are also collectively referred to as IgG.

The antibody molecule is composed of polypeptides called a heavy chain (hereinafter, referred to as H chain) and a light chain (hereinafter, referred to as L chain). The H chain is composed of a VH and an H chain constant region (also abbreviated as CH) from the N-terminal side, and the L chain is composed of a VL and an L chain constant region (also abbreviated as CL) from the N-terminal side. As for a CH, α, δ, ε, γ, and μ chains are known for each subclass. The CH is further composed of a CHI domain, a hinge region, a CH2 domain, and a CH3 domain from the N-terminal side. The domain refers to a functional structural unit constituting each polypeptide of the antibody molecule. The CH2 domain and the CH3 domain are collectively referred to as an Fc region or a simply Fc. A $Ch_\lambda$ chain and a $C_\kappa$ chain are known as the CL.

The CH1 domain, the hinge region, the CH2 domain, the CH3 domain, and the Fc region in the present invention can be specified by the number of the amino acid residue from the N-terminal by the EU index [Kabat et al., Sequences of Proteins of Immunological Interest, US Dept. Health and Human Services (1991)] (hereafter, simply referred to as the EU index). Specifically, the CHI can be identified as the amino acid sequence at positions 118 to 215 according to the EU index, the hinge can be identified as the amino acid sequence at position 216 to 230 according to the EU index, the CH2 can be identified as the amino acid sequence at position 231 to 340 according to the EU index, and the CH3 can be identified as the amino acid sequence at position 341 to 447 according to the EU index.

The antibody of the present invention also includes a recombinant antibody such as a recombinant mouse antibody, a recombinant rat antibody, a recombinant rabbit antibody, a human chimeric antibody (hereinafter, also simply referred to as a chimeric antibody), a humanized antibody (also referred to as a humanized complementarity-determining region CDR-grafted antibody), and a human antibody, which are produced in a genetic engineering manner. The antibody of the present invention also includes a recombinant antibody produced by recombining an H chain (or VH) and an L chain (or VL) derived from two different types of antibodies. The two different types of antibodies may be any of a hybridoma-derived monoclonal antibody, a chimeric antibody, a humanized antibody, and a human antibody. Further, the antibody of the present invention also includes a recombinant antibody in which an appropriate amino acid residue is substituted when preparing the above-described recombinant antibody.

The chimeric antibody indicates an antibody consisting of a VH and a VL of an antibody from an animal other than human (non-human animal) and a CH and a CL of a human antibody. Any non-human animals can be used as long as hybridomas can be prepared, such as mice, rats, hamsters, and rabbits.

The hybridoma refers to a cell that produces a monoclonal antibody having desired antigen specificity, which is obtained by fusing a B cell obtained by immunizing a non-human animal with an antigen and a myeloma cell derived from a mouse or the like. Accordingly, the variable region of the antibody produced by the hybridoma consists of the amino acid sequence of a non-human animal antibody.

The chimeric antibody can be produced by obtaining cDNAs each encoding a VH and a VL of the monoclonal antibody from monoclonal antibody-producing hybridomas derived from non-human animal cells, inserting the cDNAs into an animal cell expression vector comprising DNAs each encoding a CH and a CL of a human antibody, respectively, to construct a human chimeric antibody expression vector, and introducing the chimeric antibody expression vector into an animal cell to express the chimeric antibody.

The humanized antibody refers to an antibody obtained by grafting amino acid sequences of CDRs of a VH and a VL of a non-human animal antibody onto corresponding CDRs of a VH and a VL of a human antibody. A region other than CDRs of a VH and a VL is referred to as a framework region (hereinafter, referred to as FR).

The humanized antibody can be produced by constructing a cDNA encoding an amino acid sequence of a VH consisting of an amino acid sequence of CDR of a VH of a non-human animal antibody and an amino acid sequence of an FR of a VH of any human antibody, and a cDNA encoding an amino acid sequence of a VL consisting of an amino acid sequence of CDR of a VL of a non-human animal antibody and an amino acid sequence of an FR of a VL of any human antibody, inserting the cDNAs into an animal cell expression vector comprising DNAs each encoding a CH and a CL of a human antibody, respectively, to construct a humanized antibody expression vector, and introducing the humanized antibody expression vector into an animal cell to express the humanized antibody.

The human antibody originally refers to an antibody naturally occurring in the human body, and also includes an antibody obtained from a human antibody phage library prepared by recent advances in genetic engineering, cellular engineering, and developmental engineering technologies, and human antibody-producing transgenic animals.

The human antibody can be obtained by immunizing a mouse carrying a human immunoglobulin gene (Tomizuka K. et. al., Proc Natl Acad Sci USA. 97, 722-7, 2000) with a desired antigen. In addition, by using a phase display library obtained by amplifying an antibody gene from human-derived B cells, a human antibody having a desired binding activity is selected, and thus the human antibody can be obtained without immunization (Winter G. et. al., Annu Rev Immunol. 12:433-55. 1994). Further, by immortalizing human B cells using EB viruses, cells that produce a human antibody having a desired binding activity can be produced and a human antibody can be obtained (Rosen A. et. al., Nature 267, 52-54. 1977).

For the antibody present in the human body, for example, lymphocytes that produce the antibody can be obtained by immortalizing lymphocytes isolated from human peripheral blood with EB viruses or the like and then cloning them, and the antibody can be purified from a culture of the lymphocytes.

The human antibody phage library is a phage library from which an antibody fragment such as Fab or scFv is expressed on a surface by inserting an antibody gene prepared from a human B cell into a phage gene. From the library, a phage expressing an antibody fragment having a desired antigen binding activity can be collected by using the binding activity to a substrate immobilized with an antigen as an indicator. The antibody fragment can also be further converted into a human antibody molecule consisting of two complete H chains and two complete L chains by a genetic engineering method.

The human antibody-producing transgenic animal refers to an animal obtained by incorporating a human antibody gene into a chromosome of a host animal. Specifically, the human antibody-producing transgenic animal can be produced by introducing a human antibody gene into a mouse ES cell, and grafting the ES cell into an early embryo of another mouse to produce an individual. As a method for producing a human antibody from the human antibody-producing transgenic animal, a human antibody-producing hybridoma is obtained by a hybridoma producing method performed in a mammal other than a normal human, and cultured to produce and accumulate a human antibody in a culture.

The amino acid sequences of the VH and the VL of the antibody of the present invention may be any of amino acid sequences of a VH and a VL of a human antibody, a non-human animal antibody, or a humanized antibody.

The amino acid sequence of the CL in the antibody of the present invention may be either an amino acid sequence of a human antibody or an amino acid sequence of a non-human animal antibody, and $C_\kappa$ or $C_\lambda$ of the amino acid sequences of the human antibody is preferred.

The CH of the antibody of the present invention may be any immunoglobulin, and is preferably the subclasses γ1 (IgG1), γ2 (IgG2), γ3 (IgG3) and γ4 (IgG4) belonging to the IgG class.

The antibody of the present invention also includes an Fc fusion protein obtained by binding Fc and an antibody fragment to each other, an Fc fusion protein obtained by binding Fc and a naturally occurring ligand or a receptor to each other (also referred to as immunoadhesin), an Fc fusion protein obtained by fusing a plurality of Fc regions, and the like.

The antibody or the antibody fragment thereof of the present invention also includes an antibody comprising any post-translationally modified amino acid residue, or an antibody fragment thereof. Examples of the post-translational modification include deletion of a lysine residue of an H chain at the C-terminal (lysine clipping) and substitution of a glutamine residue of the polypeptide with pyroglutamine (pyroGlu) at the N-terminal [Beck et al, Analytical Chemistry, 85, 715-736 (2013)].

In the present invention, the antibody fragment is an antibody fragment which binds to human FGF23 and is suppressed from degrading at a low pH as compared with an antibody comprising a VH comprising the amino acid sequence represented by SEQ ID NO: 1 and a VL comprising the amino acid sequence represented by SEQ ID NO: 2. Examples of the antibody fragment in the present invention includes Fab, Fab', F(ab')₂, a single chain antibody (scFv), a dimerized V region (diabody), a disulfide-stabilized V region (dsFv), and a peptide comprising a plurality of CDRs. Fab is an antibody fragment obtained by treating an IgG antibody with a proteolytic enzyme papain (obtained by cleaving at an amino acid residue at position 224 in an H chain) and having a molecular weight of about 50000 and an antigen binding activity, in which about half of the H chain on an N-terminal side and an entire L chain bind to each other by a disulfide bond (S—S bond).

The F(ab')₂ is an antibody fragment obtained by treating an IgG antibody with a proteolytic enzyme pepsin (obtained by cleaving at an amino acid residue at position 234 in an H chain) and having a molecular weight of about 100000 and an antigen binding activity, which is slightly larger than that of Fab bound through an S—S bond in a hinge region. The Fab' is an antibody fragment obtained by cleaving the S—S bond in the hinge region of the F(ab')₂ and having a molecular weight of about 50000 and an antigen binding activity.

The scFv is a VH-P-VL or VL-P-VH polypeptide obtained by linking one VH and one VL by a suitable peptide linker (P) such as a linker peptide in which any number of linkers (G4S) consisting of 4 Gly and 1 Ser residues are connected, and is an antibody fragment having an antigen binding activity.

The Diabody is an antibody fragment obtained by forming a dimer with scFvs having the same or different antigen binding specificity, and is an antibody fragment having an divalent antigen binding activity to the same antigen or a specific antigen binding activity to different antigens.

The dsFv refers to a polypeptide in which one amino acid residue each in a VH and a VL is substituted with a cysteine residue, which are linked via an S—S bond between the cysteine residues.

The peptide comprising CDR includes at least one region of a CDR of a VH or a VL. In the peptide comprising a plurality of CDRs, the CDRs can be linked directly or via a suitable peptide linker. The peptide comprising CDR can be produced by constructing DNAs each encoding CDRs of a VH and a VL of the modified antibody of the present invention, inserting the DNAs into a prokaryotic expression vector or an eukaryotic expression vector, and introducing the expression vector into prokaryotes or eukaryotes to express the peptide comprising CDR. The peptide comprising CDR can also be produced by a chemical synthesis method such as an Fmoc method or a tBoc method.

Examples of an aspect of the antibody of the present invention include the following antibodies (i) and (ii) or antibody fragments thereof:

(i) an antibody or an antibody fragment thereof which binds to FGF23, in which the antibody comprises a VH comprising the amino acid sequence represented by SEQ ID NO: 1 and a VL comprising the amino acid sequence represented by SEQ ID NO: 2, and in which at least the amino acid residue at position 100 of the amino acid sequence represented by SEQ ID NO: 1 in the VH is substituted with one amino acid residue selected from alanine residue, asparagine residue, glycine residue, tyrosine residue, arginine residue, aspartic acid residue, histidine residue, tryptophan residue, and methionine residue, and (ii) an antibody or an antibody fragment thereof which binds to FGF23, in which the antibody comprises a VH comprising the amino acid sequence represented by SEQ ID NO: 1 and a VL comprising the amino acid sequence represented by SEQ ID NO: 2, and in which at least the amino acid residue at position 105 of the amino acid sequence represented by SEQ ID NO: 1 in the VH is substituted with one amino acid residue selected from alanine residue, phenylalanine residue, glycine residue, histidine residue, isoleucine residue, lysine residue, leucine residue, methionine residue, proline residue, glutamine residue, arginine residue, valine residue, tryptophan residue, tyrosine residue, threonine residue, asparagine residue, and serine residue.

In the antibody, the stability is high and the antibody degradation can be suppressed at a low pH as compared with the antibody comprising a VH comprising the amino acid sequence represented by SEQ ID NO: 1 and a VL comprising the amino acid sequence represented by SEQ ID NO: 2.

The antibody is preferably an antibody which binds to FGF23, in which the antibody comprises a VH comprising the amino acid sequence represented by SEQ ID NO: 1 and a VL comprising the amino acid sequence represented by SEQ ID NO: 2, and in which at least the amino acid residue at position 100 of the amino acid sequence represented by SEQ ID NO: 1 in the VH is substituted with alanine residue or tyrosine residue.

In the present invention, the low pH refers to a weakly acidic or acidic pH of less than 6, and examples thereof include, but are not particularly limited to, pH 5, pH 4.5, and pH 4.

The antibody of the present invention can be suppressed from degrading and exhibits excellent stability at a low pH as compared with the antibody comprising a VH comprising the amino acid sequence represented by SEQ ID NO: 1 and a VL comprising the amino acid sequence represented by SEQ ID NO: 2. In the present invention, the antibody degradation can be measured by size exclusion chromatography (hereinafter, referred to as SEC) or SDS polyacrylamide gel electrophoresis (hereinafter, referred to as SDS-PAGE), or the like.

The fact that, in the antibody of the present invention, the antibody degradation can be suppressed at a low pH as compared with the antibody comprising a VH comprising the amino acid sequence represented by SEQ ID NO: 1 and a VL comprising the amino acid sequence represented by SEQ ID NO: 2 can be confirmed, for example, by a method including the following steps (I) to (III), but the present invention is not limited to the method.

(I) An antibody solution is prepared by replacing a solvent of an antibody solution containing the antibody of the present invention or the antibody comprising a VH comprising the amino acid sequence represented by SEQ ID NO: 1 and a VL comprising the amino acid sequence represented by SEQ ID NO: 2 with an appropriate solvent having a pH of 4, 4.5, or 5 using a column such as NAP (trademark) 25 (GE Healthcare Life Science).

(II) The antibody solution prepared in the above (I) is allowed to stand at 40 degrees for one month or two weeks, or at 25 degrees for three months, and then peaks (%) corresponding to a degradation product of the antibody is detected by SEC.

In addition, the antibody solution prepared in the above (I) is allowed to stand at 40 degrees for one month or two weeks, or 25 degrees for three months, and then SDS-PAGE is performed under reduction conditions to detect a band at about 40 kDa (for example, 35 kDa to 45 kDa) corresponding to a degradation product of the antibody.

(III) When the peak (%) corresponding to a degradation product of the antibody that is detected by SEC in the above (II) is reduced in the antibody of the present invention as compared with the antibody comprising a VH comprising the amino acid sequence represented by SEQ ID NO: 1 and a VL comprising the amino acid sequence represented by SEQ ID NO: 2, or when a density of the band at about 40 kDa in SDS-PAGE is lower in the antibody of the present invention as compared with the antibody comprising a VH comprising the amino acid sequence represented by SEQ ID NO: 1 and a VL comprising the amino acid sequence represented by SEQ ID NO: 2, it can be confirmed that, in the antibody of the present invention, the antibody degradation can be suppressed at a low pH as compared with the antibody comprising a VH comprising the amino acid sequence represented by SEQ ID NO: 1 and a VL comprising the amino acid sequence represented by SEQ ID NO: 2.

Instead of the SDS-PAGE described in the above (II), a Bioanalyzer Electrophoresis System (Agilent Technologies, Inc.) and an Agilent Protein 230 Kit (Agilent Technologies, Inc.) may be used. At this time, when a peak area ratio (%) of the band (for example, 40 kDa to 60 kDa) corresponding to a degradation product of the antibody that is detected in a size smaller by about 10 kDa to 20 kDa than that of a peak of the total length of the H chain is lower in the antibody of the present invention as compared with the antibody comprising a VH comprising the amino acid sequence represented by SEQ ID NO: 1 and a VL comprising the amino acid sequence represented by SEQ ID NO: 2, it can be confirmed that, in the antibody of the present invention, the antibody degradation can be suppressed at a low pH as compared with the antibody comprising a VH comprising the amino acid sequence represented by SEQ ID NO: 1 and a VL comprising the amino acid sequence represented by SEQ ID NO: 2.

That is, as an aspect in which the antibody of the present invention exhibits stability at a low pH, examples thereof include the following.

As compared with the antibody comprising a VH comprising the amino acid sequence represented by SEQ ID NO: 1 and a VL comprising the amino acid sequence represented by SEQ ID NO: 2, the density of the band corresponding to a molecular weight of about 40 kDa by SDS-PAGE is lower after standing at a low pH such as pH 4, 4.5 or 5 at 40 degrees for one month or two weeks, or at 25 degrees for three months. The density of the band can be visually evaluated.

As compared with the antibody comprising a VH comprising the amino acid sequence represented by SEQ ID NO: 1 and a VL comprising the amino acid sequence represented by SEQ ID NO: 2, the peak (%) corresponding to a degradation product of the antibody that is detected by SEC is reduced after standing at a low pH such as pH 4, 4.5 or 5 at 40 degrees for one month or two weeks, or at 25 degrees for three months. As compared with the antibody comprising a VH containing the amino acid sequence represented by SEQ ID NO: 1 and a VL comprising the amino acid sequence represented by SEQ ID NO: 2, the peak (%) is preferably reduced by 5% or more, 10% or more, 20% or more, 30% or more, 40% or more, 50% or more, 60% or more, 70% or more, 80% or more, or 90% or more.

As compared with the antibody comprising a VH comprising the amino acid sequence represented by SEQ ID NO: 1 and a VL comprising the amino acid sequence represented by SEQ ID NO: 2, the peak area ratio (%) of the band (for example, 40 kDa to 60 kDa) corresponding to the degradation product of the antibody that is detected in a size smaller by about 10 kDa to 20 kDa than that of the peak of the total length of the H chain is reduced in electropherograms using a Bioanalyzer Electrophoresis System (Agilent Technologies, Inc.) and an Agilent Protein 230 Kit (Agilent Technologies, Inc.) after standing at a low pH such as pH 4, 4.5 or 5 at 40 degrees for one month or two weeks, or at 25 degrees for three months. As compared with the antibody comprising a VH comprising the amino acid sequence represented by SEQ ID NO: 1 and a VL comprising the amino acid sequence represented by SEQ ID NO: 2, the peak area ratio (%) is preferably reduced by 5% or more, 10% or more, 20% or more, 30% or more, 40% or more, 50% or more, 60% or more, 70% or more, 80% or more, or 90% or more.

Examples of one aspect of the antibody of the present invention include the above-described antibody further comprising one substitution selected from the following (a1) to (a4):

(a1) at least one substitution selected from substitution of the amino acid residue at position 50 with leucine residue, substitution of the amino acid residue at position 54 with tryptophan residue, substitution of the amino acid residue at position 55 with histidine residue, substitution of the amino acid residue at position 57 with threonine residue, and substitution of the amino acid residue at position 58 with phenylalanine residue in the amino acid sequence represented by SEQ ID NO: 1 in the VH, (a2) at least one substitution selected from substitution of the amino acid residue at position 91 with methionine residue or leucine residue, substitution of the amino acid residue at position 92 with tyrosine residue, substitution of the amino acid residue at position 94 with aspartic acid residue, and substitution of the amino acid residue at position 96 with asparagine residue or aspartic acid residue in the amino acid sequence represented by SEQ ID NO: 2 in the VL, (a3) at least one substitution selected from substitution of the amino acid residue at position 28 with aspartic acid residue, substitution of the amino acid residue at position 29 with valine residue, substitution of the amino acid residue at position 31 with threonine residue, and substitution of the amino acid residue at position 34 with leucine residue in the amino acid sequence represented by SEQ ID NO: 2 in the VL, and (a4) at least one substitution selected from substitution of the amino acid residue at position 92 with tyrosine residue or tryptophan residue, substitution of the amino acid residue at position 94 with aspartic acid residue, and substitution of the amino acid residue at position 96 with aspartic acid residue in the amino acid sequence represented by SEQ ID NO: 2 in the VL.

The antibody of the present invention preferably has all amino acid residue substitutions described in respective (a1) to (a4) above.

The antibody of the present invention may have an improved binding activity to FGF23 and an FGF23 neutralizing activity by one amino acid residue substitution selected from the (a1) to (a4) above. The FGF23 neutralizing activity refers to an activity of inhibiting a signal generated by binding of FGF23 to a receptor. An example of an FGF23 receptor is a complex between FGFR1 and αKlotho.

The FGF23 neutralizing activity of the antibody of the present invention can be confirmed by a reporter assay (also called promoter assay) described in Nature 2006 Dec. 7; 444 (7120), or the like. The FGF23 neutralizing activity of the antibody of the present invention can also be confirmed by a reporter assay using αKlotho stably expressing HEK293 cells transformed with a luciferase expression vector having a promoter derived from a mouse Egr1 gene.

Specific examples of the antibody of the present invention include any one antibody selected from the following (b1) to (b5).

(b1) An antibody comprising a VH comprising the amino acid sequence represented by SEQ ID NO: 1 and a VL comprising the amino acid sequence represented by SEQ ID NO: 2, in which the amino acid residue at position 50 is substituted with leucine residue, the amino acid residue at position 54 is substituted with tryptophan residue, the amino acid residue at position 55 is substituted with histidine residue, the amino acid residue at position 57 is substituted with threonine residue, the amino acid residue at position 58 is substituted with phenylalanine residue, and the amino acid residue at position 100 is substituted with alanine residue or tyrosine residue in the amino acid sequence represented by SEQ ID NO: 1 in the VH, (b2) An antibody comprising a VH comprising the amino acid sequence represented by SEQ ID NO: 1 and a VL comprising the amino acid sequence represented by SEQ ID NO: 2, in which the amino acid residue at position 100 is substituted with alanine residue or tyrosine residue in the amino acid sequence represented by SEQ ID NO: 1 in the VH, and the amino acid residue at position 91 is substituted with methionine residue, the amino acid residue at position 92 is substituted with tyrosine residue, the amino acid residue at position 94 is substituted with aspartic acid residue, and the amino acid residue at position 96 is substituted with asparagine residue in the amino acid sequence represented by SEQ ID NO: 2 in the VL, (b3) An antibody comprising a VH comprising the amino acid sequence represented by SEQ ID NO: 1 and a VL comprising the amino acid sequence represented by SEQ ID NO: 2, in which the amino acid residue at position 100 is substituted with alanine residue or tyrosine residue in the amino acid sequence represented by SEQ ID NO: 1 in the VH, and the amino acid residue at position 28 is substituted with aspartic acid residue, the amino acid residue at position 29 is substituted with valine residue, the amino acid residue at position 31 is substituted with threonine residue, and the amino acid residue at position 34 is substituted with leucine residue in the amino acid sequence represented by SEQ ID NO: 2 in the VL, (b4) An antibody comprising a VH comprising the amino acid sequence represented by SEQ ID NO: 1 and a VL comprising the amino acid sequence represented by SEQ ID NO: 2, in which the amino acid residue at position 100 is substituted with alanine residue or tyrosine residue in the amino acid sequence represented by SEQ ID NO: 1 in the VH, and the amino acid residue at position 91 is substituted with leucine residue, the amino acid residue at position 92 is substituted with tyrosine residue, the amino acid residue at position 94 is substituted with aspartic acid residue, and the amino acid residue at position 96 is substituted with aspartic acid residue in the amino acid sequence represented by SEQ ID NO: 2 in the VL, and (b5) An antibody comprising a VH comprising the amino acid sequence represented by SEQ ID NO: 1 and a VL comprising the amino acid sequence represented by SEQ ID NO: 2, in which the amino acid residue at position 100 is substituted with alanine residue or tyrosine residue in the amino acid sequence represented by SEQ ID NO: 1 in the VH, and the amino acid residue at position 92 is substituted with tyrosine residue or tryptophan residue, the amino acid residue at position 94 is substituted with aspartic acid residue, and the amino acid residue at position 96 is substituted with aspartic acid residue in the amino acid sequence represented by SEQ ID NO: 2 in the VL.

Specific examples of the antibody of the present invention include antibodies selected from the following (c1) to (c10), (cl), (c8), (c9), or (c10) is preferred, and (c1) or (c9) is more preferred.

(c1) an antibody comprising a VH comprising the amino
acid sequence represented by SEQ ID NO: 39 and a VL
comprising the amino acid sequence represented by
SEQ ID NO: 2, (c2) an antibody comprising a VH comprising the amino
acid sequence represented by SEQ ID NO: 47 and a VL
comprising the amino acid sequence represented by
SEQ ID NO: 2, (c3) an antibody comprising a VH comprising the amino
acid sequence represented by SEQ ID NO: 3 and a VL
comprising the amino acid sequence represented by
SEQ ID NO: 44, (c4) an antibody comprising a VH comprising the amino
acid sequence represented by SEQ ID NO: 6 and a VL
comprising the amino acid sequence represented by
SEQ ID NO: 44, (c5) an antibody comprising a VH comprising the amino
acid sequence represented by SEQ ID NO: 3 and a VL
comprising the amino acid sequence represented by
SEQ ID NO: 45, (c6) an antibody comprising a VH comprising the amino
acid sequence represented by SEQ ID NO: 6 and a VL
comprising the amino acid sequence represented by
SEQ ID NO: 45, (c7) an antibody comprising a VH comprising the amino
acid sequence represented by SEQ ID NO: 3 and a VL
comprising the amino acid sequence represented by
SEQ ID NO: 46, (c8) an antibody comprising a VH comprising the amino
acid sequence represented by SEQ ID NO: 6 and a VL
comprising the amino acid sequence represented by
SEQ ID NO: 46, (c9) an antibody comprising a VH comprising the amino
acid sequence represented by SEQ ID NO: 3 and a VL
comprising the amino acid sequence represented by
SEQ ID NO: 58, and (c10) an antibody comprising a VH comprising the amino
acid sequence represented by SEQ ID NO: 6 and a VL
comprising the amino acid sequence represented by
SEQ ID NO: 59.

In the antibody of the present invention, for the purpose
of controlling the blood half-life, an Fc region in which the
amino acid residue is substituted to control the binding
ability to FcRn can also be used.

Examples of the Fc region in which the amino acid
residue is substituted to improve the binding ability of the
antibody to FcRn include the Fc region of any one of the
following (d1) to (d5). Among them, the Fc region of (d1)
is preferred.

(d1) an Fc region comprising substitution of the amino
acid residue at position 252 with tyrosine residue,
substitution of the amino acid residue at position 254
with threonine residue, and substitution of the amino
acid residue at position 256 with glutamic acid residue
according to the EU index, (d2) an Fc region comprising substitution of the amino
acid residue at position 428 with leucine residue, and
substitution of the amino acid residue at position 434
with serine residue according to the EU index, (d3) an Fc region comprising substitution of the amino
acid residue at position 308 with proline residue
according to the EU index, (d4) an Fc region comprising substitution of the amino
acid residue at position 250 with glutamine residue, and
substitution of the amino acid residue at position 428
with leucine residue according to the EU index, and (d5) an Fc region comprising substitution of the amino
acid residue at position 434 with alanine residue
according to the EU index.

In the present invention, specific examples of the amino
acid sequence of a heavy chain constant region comprising
the Fc region in which the amino acid residue is substituted
to improve the binding ability of the antibody to FcRn
include the amino acid sequences represented by SEQ ID
NOs: 48, 49, 50, 51, and 52. Among them, the amino acid
sequence represented by SEQ ID NO: 48 is preferred.

The monoclonal antibody or the antibody fragment
thereof of the present invention includes a derivative of the
antibody or the antibody fragment thereof, which is obtained
by chemically or genetically binding a radioactive isotope,
a low-molecular drug, a high-molecular drug, a protein, or
an antibody drug to the monoclonal antibody or the antibody
fragment thereof which binds to human FGF23 of the
present invention.

The derivative of the antibody or the antibody fragment
thereof can be produced by binding, by a chemical method
[Introduction to Antibody Engineering, Chijin Shokan
(1994)], a radioactive isotope, a low-molecular drug, a
high-molecular drug, a protein, an antibody drug, or an
nucleic acid drug to an N-terminal side or C-terminal side of
the H chain or L chain of the monoclonal antibody or the
antibody fragment thereof which binds to human FGF23 of
the present invention, an appropriate substituent or a side
chain or sugar chain in the antibody molecule.

In addition, the derivative of the antibody or the antibody
fragment thereof can be produced by a genetic engineering
method in which a DNA encoding the monoclonal antibody
or the antibody fragment thereof which binds to human
FGF23 of the present invention and a DNA encoding a
protein or an antibody drug to be bound are connected and
inserted into an expression vector, and the expression vector
is introduced into a suitable host cell to express to the
derivative.

Examples of the radioactive isotope include $^{111}$In, $^{131}$I,
$^{125}$I, $^{90}$Y, $^{64}$Cu, $^{99}$Tc, $^{77}$Lu, and $^{211}$At. The radioactive
isotope can directly bind to the antibody by a chloramine T
method or the like. A substance for chelating the radioactive
isotope may bind to the antibody. Examples of the chelating
reagent include 1-isothiocyanatebenzyl-3-methyldiethylen-
etriaminepentaacetic acid (MX-DTPA).

Examples of the low-molecular drug include an alkylating
agent, nitrosourea, an antimetabolite, an antibiotic, a plant
alkaloid, a topoisomerase inhibitor, a hormone therapy
agent, a hormone antagonist, an aromatase inhibitor, a
P-glycoprotein inhibitor, a platinum complex derivative, an
anticancer agent such as an M-phase inhibitor or a kinase
inhibitor [Clinical Oncology, Cancer and Chemotherapy
(1996)], a steroidal drug such as hydrocortisone or predni-
sone, a non-steroidal drug such as aspirin or indomethacin,
an immunomodulator such as gold thiomalate or penicil-
lamine, an immunosuppressant such as cyclophosphamide
or azathioprine, and an anti-inflammatory agent such as an
antihistamine such as chlorpheniramine maleate or clemaci-
tin [Inflammation and anti-inflammatory therapy, Ishiyaku
Pub, Inc. (1982)].

Examples of the anticancer agent include amifostine
(ethiol), cisplatin, dacarbazine (DTIC), dactinomycin,
mechlorethamine (nitrogen mustard), streptozocin, cyclo-
phosphamide, ifosfamide, carmustine (BCNU), iomustine
(CCNU), doxorubicin (Adriamycin), epirubicin, gemcit-
abine (Gemzar), daunorubicin, procarbazine, mitomycin,
cytarabine, etoposide, methotrexate, 5-fluorouracil, fluorou-
racil, vinblastine, vincristine, bleomycin, daunomycin, pepromycin, estramustine, paclitaxel (Taxol), docetaxel (Taxotea), aldesleukin, asparaginase, busulfan, carboplatin, oxaliplatin, nedaplatin, cladribine, camptothecin, 10-hydroxy-7-ethyl-camptothecin (SN38), floxuridine, fludarabine, hydroxyurea, idarubicin, mesna, irinotecan (CPT-11), nogitecan, mitoxantrone, topotecan, leuprolide, megestrol, melphalan, mercaptopurine, hydroxycarbamide, plicamycin, mitotane, pegasparagase, pentostatin, pipobroman, tamoxifen, goserelin, leuprorenin, flutamide, teniposide, testolactone, thioguanine, thiotepa, uracil mustard, vinorelbine, chlorambucil, hydrocortisone, prednisolone, methylprednisolone, vindesine, nimustine, semustine, capecitabine, tomdex, azacitidine, UFT, oxaloplatin, gefitinib (Iressa), imatinib (STI571), erlotinib, an FMS-like tyrosine kinase 3 (Flt3) inhibitor, a vascular endothelial growth factor receptor (VEGFR) inhibitor, a fibroblast growth factor receptor (FGFR) inhibitor, an epidermal growth factor receptor (EGFR) inhibitor such as Iressa and Tarceva, radicicol, 17-allylamino-17-demethoxygeldanamycin, rapamycin, amsacrine, all-trans retinoic acid, thalidomide, lenalidomide, anastrozole, fadrozole, letrozole, exemestane, gold thiomalate, D-penicillamine, bucillamine, azathioprine, mizoribine, cyclosporine, rapamycin, hydrocortisone, bexarotene (Targretin), tamoxifen, dexamethasone, progestins, estrogens, anastrozole (Arimidex), leuprolide, aspirin, indomethacin, celecoxib, penicillamine, gold thiomalate, chlorpheniramine maleate, chlorpheniramine, clemacitin, tretinoin, bexarotene, arsenic, bortezomib, allopurinol, calicheamicin, ibritumomab tiuxetan, targretin, ozogamine, clarithromacin, leucovorin, ketoconazole, aminoglutethimide, suramin, and maytansinoid, or a derivative thereof.

Examples of the method of binding a low-molecular drug to an antibody include a method of binding a drug with an amino group of the antibody via glutaraldehyde, and a method of bonding an amino group of a drug and a carboxy group of the antibody via water-soluble carbodiimide.

Examples of the high-molecular drug include polyethylene glycol (hereinafter, referred to as PEG), albumin, dextran, polyoxyethylene, a styrene maleic acid copolymer, polyvinylpyrrolidone, a pyran copolymer, or hydroxypropyl methacrylamide. By linking the high molecular weight compound to the antibody or the antibody fragment thereof, effects such as (1) improvement of stability with respect to various chemical, physical, or biological factors, (2) significant extension of blood half-life, and (3) loss of immunogenicity or suppression of antibody production are expected [Bioconjugate pharmaceuticals, Hirokawa Shoten (1993)].

Examples of the method of linking a PEG and the antibody include a method for reacting with a PEGylation modification reagent [Bioconjugate pharmaceuticals, Hirokawa Shoten (1993)]. Examples of the PEGylation modification reagent include a modifier for an ε-amino group of lysine (JP61-178926A), a modifier for a carboxy group of aspartic acid and glutamic acid (JP56-23587A), or a modifier for a guanidino group of arginine (JP2-117920A).

The immunostimulant may be a natural product known as an immunoadjuvant, and specific examples thereof include drugs that enhance immunity, such as β(1→3) glucan (for example, lentinan or schizophyllan), or α-galactosylceramide (KRN7000).

Examples of the protein include a cytokine or a growth factor that activates immunocompetent cells such as NK cells, macrophages, or neutrophils, or a toxin protein.

Examples of the cytokine or growth factor include interferon (hereinafter referred to as IFN)-α, IFN-β, IFN-γ, interleukin (hereinafter, referred to as IL)-2, IL-12, IL-15, IL-18, IL-21, and IL-23, a granulocyte-colony stimulating factor (G-CSF), a granulocyte/macrophage-colony stimulating factor (GM-CSF), or a macrophage-colony stimulating factor (M-CSF). Examples of the toxin protein include ricin, diphtheria toxin, or ONTAK, and the toxin protein also includes a protein toxin obtained by introducing a mutation into a protein to adjust toxicity.

Examples of the antibody drug include an antibody against an antigen that induces apoptosis upon antibody binding, an antigen that is associated with pathogenesis of tumors, an antigen that regulates an immune function, and an antigen that is associated with angiogenesis at a lesion site.

Examples of the antigen that induces apoptosis upon antibody binding include a cluster of differentiation (hereinafter, referred to as CD) 19, CD20, CD21, CD22, CD23, CD24, CD37, CD53, CD72, CD73, CD74, CDw75, CDw76, CD77, CDw78, CD79a, CD79b, CD80 (B7.1), CD81, CD82, CD83, CDw84, CD85, CD86 (B7.2), human leukocyte antigen (HLA)-Class II, or Epidermal Growth Factor Receptor (EGFR).

Examples of the antigen that is associated with pathogenesis of tumors or the antigen of an antibody that regulates an immune function include CD4, CD40, a CD40 ligand, a B7 family molecule (for example, CD80, CD86, CD274, B7-DC, B7-H2, B7-H3, or B7-H4), a B7 family molecule ligand (for example, CD28, CTLA-4, ICOS, PD-1, or BTLA), OX-40, an OX-40 ligand, CD137, a tumor necrosis factor (TNF) receptor family molecule (for example, DR4, DR5, TNFR1, or TNFR2), a TNF-related apoptosis-inducing ligand receptor (TRAIL) family molecule, a TRAIL family molecule receptor family (for example, TRAIL-RI, TRAIL-R2, TRAIL-R3, or TRAIL-R4), a receptor activator of nuclear factor kappa B ligand (RANK), a RANK ligand, CD25, a folate receptor, cytokines [for example, IL-1α, IL-1β, IL-4, IL-5, IL-6, IL-10, IL-13, transforming growth factor (TGF)β or TNFα] or receptors for these cytokines, or chemokines (for example, SLC, ELC, I-309, TARC, MDC, or CTACK), or receptors for these chemokines.

Examples of the antigen of an antibody that inhibits angiogenicity of a lesion site include a vascular endothelial growth factor (VEGF), an angiopoietin, a fibroblast growth factor (FGF), EGF, a hepatocyte growth f factor (HGF), a platelet-derived growth factor (PDGF), an insulin-like growth factor (IGF), erythropoietin (EPO), TGFβ, IL-8, ephrin, SDF-1, or receptors thereof.

Examples of the nucleic acid drug include a drug medicine such as small interference ribonucleic acid (siRNA) or microRNA that act on living organisms by controlling gene functions. For example, a conjugate with a nucleic acid drug that suppresses a master transcription factor RORγt of Th17 cells can be considered.

When the derivative of the antibody or the antibody fragment thereof of the present invention is used for detection and measurement of human FGF23 and diagnosis of a disease associated with human FGF23, examples of the drug linking to the antibody include a labeling material used in ordinary immunological detection or measurement methods. Examples of the labeling material include an enzyme such as alkaline phosphatase, peroxidase, or luciferase, a luminescent substance such as an acridinium ester or a lophine, or a fluorescent substance such as fluorescein isothiocyanate (FITC) or tetramethylrhodamine isothiocyanate (RITC).

One embodiment of the present invention is a composition containing the antibody or the antibody fragment thereof of the invention. Examples of the form of the composition include a composition containing, as an active ingredient, a monoclonal antibody or an antibody fragment thereof which binds to human FGF23. The composition containing the antibody or the antibody fragment thereof of the present invention can be used for treatment of a disease associated with human FGF23. As one embodiment of the present invention, a therapeutic agent for a disease associated with human FGF23 that contains the antibody of the present invention is provided.

The present invention also relates to a therapeutic method for a disease associated with human FGF23 that includes administering the monoclonal antibody or the antibody fragment thereof which binds to human FGF23.

The disease associated with human FGF23 may be any disease associated with human FGF23 or a human FGF23 receptor. Examples thereof include tumor-induced osteomalacia (TIO), autosomal dominant hypophosphatemic rickets/osteomalacia (ADHR), X-linked hypophosphatemic rickets (XLH), fibrous dysplasia, McCune-Albright syndrome, autosomal recessive hypophosphatemic rickets/osteomalacia (ARHR), osteoporosis, rickets (including hypophosphatemic rickets and vitamin D-resistant rickets), hypercalcemia, hypocalcemia, ectopic calcification, osteosclerosis, Paget's disease, hyperparathyroidism, hypoparathyroidism, pruritus, and diseases associated with renal failure or dialysis during renal failure, such as renal osteodystrophy, dialysis osteopathy, and renal tubular dysfunction.

The present invention also includes a therapeutic agent for symptoms such as hypophosphatemia, bone mineralization failure, bone pain, muscle weakness, skeletal deformation, growth disorder, and 1,25-vitamin D hypovitaminosis, which are observed in diseases such as TIO, ADHR, XLH, fibrous dysplasia, McCune-Albright syndrome, and ARHR. The therapeutic agent contains, as an active ingredient, a monoclonal antibody or an antibody fragment thereof which binds to human FGF23.

The therapeutic agent containing the antibody or the antibody fragment thereof of the present invention may contain only the antibody or the antibody fragment thereof as an active ingredient, and it is preferable that the therapeutic agent is mixed together with one or more pharmacologically acceptable carriers and provided as a pharmaceutical formulation prepared by any method known in the pharmaceutical art.

It is preferred to use a most effective route of administration for treatment. Examples thereof include oral administration, and parenteral administration such as buccal, tracheobronchial, intrarectal, subcutaneous, intramuscular, or intravenous administration. Preferred examples thereof include intravenous administration. Examples of a dosage form include sprays, capsules, tablets, powders, granules, syrups, emulsions, suppositories, injections, ointments, and tapes.

A dosage or the number of doses varies depending on a desired therapeutic effect, an administration method, a treatment period, an age, a body weight, or the like, and is generally 10 μg/kg to 10 mg/kg per day for adults.

Examples of one embodiment of the composition of the present invention include a reagent for detecting or measuring FGF23, which contains a monoclonal antibody or an antibody fragment thereof which binds to human FGF23. The present invention relates to a method for detecting or measuring FGF23 using a monoclonal antibody or an antibody fragment thereof which binds to human FGF23. As a method for detecting or measuring human FGF23 in the present invention, any well-known method can be used. Examples thereof include an immunological detection or measurement method.

The immunological detection or measurement method is a method for detecting or measuring an antibody amount or antigen amount using a labeled antigen or antibody. Examples of the immunological detection or measurement method include a radiolabeled immune antibody method (RIA), enzyme immunoassay (EIA or ELISA), fluorescence immunoassay (FIA), luminescent immunoassay, Western blotting, or a physicochemical method.

Examples of one embodiment of the composition of the present invention include a diagnostic agent for a disease associated with FGF23, which contains a monoclonal antibody or an antibody fragment thereof which binds to human FGF23. The present invention relates to a method for diagnosing a disease associated with FGF23, which contains detecting or measuring FGF23 using a monoclonal antibody or an antibody fragment thereof which binds to human FGF23. The disease associated with human FGF23 can be diagnosed by using the monoclonal antibody or the antibody fragment thereof of the present invention to detect or measure human FGF23 according to the above-described method.

In the present invention, a biological sample to be detected or measured for human FGF23 is not particularly limited as long as it may contain human FGF23, such as a tissue, cells, blood, plasma, serum, a pancreatic fluid, urine, feces, a tissue fluid, or a culture medium. A diagnostic agent containing the monoclonal antibody or the antibody fragment thereof of the present invention may contain a reagent for performing an antigen-antibody reaction and a detection reagent for the reaction, depending on an intended diagnostic method. Examples of the reagent for performing an antigen-antibody reaction include a buffer and a salt. Examples of the detection reagent include a labeled secondary antibody that recognizes the monoclonal antibody or the antibody fragment thereof, or a reagent used in ordinary immunological detection or measurement methods, such as a substrate compatible with labels.

One embodiment of the present invention relates to use of an anti-human FGF23 monoclonal antibody or an antibody fragment thereof for manufacture of a therapeutic or diagnostic agent for a disease associated with FGF23. One embodiment of the present invention relates to a method for treating or diagnosing a disease associated with FGF23.

Hereinafter, the method for producing the antibody, the therapeutic method for a disease, and the diagnosis method for a disease of the present invention will be specifically described.

1. Method for Producing Antibody (1) Preparation of Antigen

Human FGF23 as an antigen can be obtained by introducing an expression vector comprising a cDNA encoding full-length human FGF23 or a partial length thereof into *Escherichia coli*, yeast, insect cells, animal cells, or the like. The human FGF23 can also be obtained by purifying human FGF23 from various human cell lines, human cells, human tissues, and the like that express large amounts of human FGF23. The human cell lines, human cells, human tissues, and the like may be used as antigens as they are. Further, a synthetic peptide having a partial sequence of the human FGF23 can be prepared by a chemical synthesis method such as an Fmoc method or a tBoc method and used as an antigen. A well-known tag such as FLAG or His may be added to the human FGF23 or a synthetic peptide having a partial sequence of the human FGF23 at the C-terminal or N-terminal.

The human FGF23 used in the present invention can be produced by expressing a DNA encoding the human FGF23 in a host cell using a method described in Molecular Cloning, A Laboratory Manual, Second Edition, Cold Spring Harbor Laboratory Press (1989) and Current Protocols In Molecular Biology, John Wiley & Sons (1987-1997), and the like, for example, by the following method.

First, a recombinant vector is prepared by inserting a full-length cDNA comprising a portion encoding the human FGF23 downstream of a promoter of an appropriate expression vector. Instead of the full-length cDNA described above, a DNA fragment of an appropriate length prepared based on the full-length cDNA and comprising a portion encoding a polypeptide may be used. Next, by introducing the obtained recombinant vector into a host cell compatible with the expression vector, a transformant that produces a polypeptide can be obtained.

Any expression vectors can be used as long as it is capable of autonomous replication in a host cell to be used or integration into a chromosome, and contains an appropriate promoter at a position where a DNA encoding a polypeptide can be transcribed. Any host cells can be used as long as it can express a target gene, such as microorganisms belonging to the genus Escherichia such as Escherichia coli, yeast, insect cells, or animal cells.

When using prokaryotes such as Escherichia coli as the host cell, the recombinant vector is preferably a vector that is capable of autonomous replication in prokaryotes and contains a promoter, a ribosome binding sequence, a DNA comprising a portion encoding the human FGF23, and a transcription termination sequence. Although the recombinant vector does not necessarily have a transcription termination sequence, it is preferred to place the transcription termination sequence immediately below a structural gene. Further, the recombinant vector may contain a gene that controls a promoter.

As the recombinant vector, it is preferred to use a plasmid in which a distance between a Shine-Dalgarno sequence (also called SD sequence), which is a ribosome binding sequence, and an initiation codon is adjusted to an appropriate distance (for example, 6 bases to 18 bases).

As a nucleotide sequence of the DNA encoding the human FGF23, bases can be substituted such that the codon is optimal for expression in the host, thereby improving a production rate of the target human FGF23.

Any expression vector can be used as long as it can function in a host cell to be used. Examples thereof include pBTrp2, pBTac1, and pBTac2 (manufactured by Roche Diagnostics), pKK233-2 (manufactured by Pharmacia), pSE280 (manufactured by Invitrogen), pGEMEX-1 (manufactured by Promega), pQE-8 (manufactured by Qiagen), pKYP10 (JP58-110600A), pKYP200 [Agricultural Biological Chemistry, 48, 669 (1984)], pLSA1 [Agric. Biol. Chem., 53, 277 (1989)], pGEL1 [Proc. Natl. Acad. Sci. USA, 82, 4306 (1985)], pBluescript II SK(−) (manufactured by Stratagene Corporation), pTrs30 [prepared from Escherichia coli JM109/pTrS30 (FERM BP-5407)], pTrs32 [prepared from Escherichia coli JM109/pTrS32 (FERM BP-5408)], pGHA2 [prepared from Escherichia coli IGHA2 (FERM BP-400), JP60-221091A], pGKA2 [prepared from Escherichia coli IGKA2 (FERM BP-6798), JP60-221091A], pTerm2 (U.S. Pat. Nos. 4,686,191, 4,939,094, 160,735), pSupex, pUB110, pTP5, pC194, and pEG400 [J. Bacteriol., 172, 2392 (1990)], pGEX (manufactured by Pharmacia), a pET system (manufactured by Novagen), or pME18SFL3.

Any promoter may be used as long as it can function in a host cell to be used. Examples thereof include a promoter derived from Escherichia coli or a phage, such as a trp promoter (Ptrp), a lac promoter, a PL promoter, a PR promoter, or a T7 promoter. Examples thereof include an artificially designed promoter such as a tandem promoter with two Ptrps arranged in series, a tac promoter, a lacT7 promoter, and a let I promoter.

Examples of the host cell include Escherichia coli XL1-Blue, Escherichia coli XL2-Blue, Escherichia coli DH1, Escherichia coli MC1000, Escherichia coli KY3276, Escherichia coli W1485, Escherichia coli JM109, Escherichia coli HB101, Escherichia coli No. 49, Escherichia coli W3110, Escherichia coli NY49, and Escherichia coli DH5α.

Any method for introducing a recombinant vector into a host cell can be used as long as it introduces a DNA into a host cell to be used, such as a method using calcium ions [Proc. Natl. Acad. Sci. USA, 69, 2110 (1972), Gene, 17, 107 (1982), Molecular & General Genetics, 168, 111 (1979)].

When using an animal cell as a host, any expression vector that can function in an animal cell can be used. Examples thereof include pcDNAI, pCDM8 (manufactured by Funakoshi), pAGE107 [JP3-22979A; Cytotechnology, 3, 133 (1990)], pAS3-3 (JP2-227075A), pCDM8 [Nature, 329, 840 (1987)], pcDNAI/Amp (manufactured by Invitrogen), pcDNA3.1 (manufactured by Invitrogen), pREP4 (manufactured by Invitrogen), PAGE103 [J. Biochemistry, 101, 1307 (1987)], and pAGE210, pME18SFL3, pKANTEX93 (WO97/10354), N5 KG1val (U.S. Pat. No. 6,001,358), INPEP4 (manufactured by Biogen-IDEC), and a transposon vector (WO2010/143698).

Any promoter can be used as long as it can function in an animal cell, and examples thereof include a cytomegalovirus (CMV) immediate early (IE) gene promoter, a SV40 early promoter, a retrovirus promoter, a metallothionein promoter, a heat shock promoter, an SRα promoter, or a Moloney murine leukemia virus promoter or enhancer. A human CMV IE gene enhancer may be used together with the promoter.

Examples of the host cell include human leukemia cells Namalwa cells, monkey cells COS cells, Chinese hamster ovary cells CHO cells [Journal of Experimental Medicine, 108, 945 (1958); Proc. Natl. Acad. Sci. USA, 60, 1275 (1968); Genetics, 55, 513 (1968); Chromosoma, 41, 129 (1973); Methods in Cell Science, 18, 115 (1996); Radiation Research, 148, 260 (1997); Proc. Natl. Acad. Sci. USA, 77, 4216 (1980); Proc. Natl. Acad. Sci., 60, 1275 (1968); Cell, 6, 121 (1975); Molecular Cell Genetics, Appendix I, II (pp. 883-900)]; CHO cells (CHO/DG44 cells) from which a dihydrofolate reductase gene (hereinafter, referred to as dhfr) is deleted [Proc. Natl. Acad. Sci. USA, 77, 4216 (1980)], CHO-K1 (ATCC CCL-61), DUKXB11 (ATCC CCL-9096), Pro-5 (ATCC CCL-1781), CHO-S (Life Technologies, Cat #11619), Pro-3, rat myeloma cells YB2/3HL.P2.G11.16Ag.20 (also called YB2/0), mouse myeloma cells NS0, mouse myeloma cells SP2/0-Ag14, and Syrian hamster cells BHK or HBT5637 (JP63-000299A).

Any method for introducing a recombinant vector into a host cell can be used, and examples thereof include an electroporation method [Cytotechnology, 3, 133 (1990)], a calcium phosphate method (JP2-227075A), or a lipofection method [Proc. Natl. Acad. Sci. USA, 84, 7413 (1987)].

The human FGF23 can be produced by culturing, in a medium, a transformant derived from a microorganism, an animal cell, or the like having a recombinant vector incorporated with the DNA encoding the human FGF23 obtained as described above, producing and accumulating the human FGF23 in a culture, and collecting the human FGF23 from the culture. The transformant can be cultured in a medium according to a general method used for culturing hosts.

When expressed in cells derived from eukaryotes, human FGF23 with an added sugar or sugar chain can be obtained.

When culturing a microorganism transformed with a recombinant vector using an inducible promoter, an inducer may be added to the medium as necessary. For example, when culturing a microorganism transformed with a recombinant vector using a lac promoter, isopropyl-β-D-thiogalactopyranoside or the like may be added to the medium, and when culturing a microorganism transformed with a recombinant vector using a trp promoter, indole acrylic acid or the like may be added to the medium.

Examples of the medium for culturing the obtained transformant using an animal cell as a host include a generally used RPMI1640 medium [The Journal of the American Medical Association, 199, 519 (1967)], an Eagle's MEM medium [Science, 122, 501 (1952)], a Dulbecco's modified MEM medium [Virology, 8, 396 (1959)], a 199 medium [Proc. Soc. Exp. Biol. Med., 73, 1 (1950)], an Iscove's Modified Dulbecco's Medium (IMDM) medium, and a medium containing fetal bovine serum (FBS). The culture is generally performed for 1 day to 7 days under conditions of pH 6 to 8, 30° C. to 40° C., and the presence of 5% $CO_2$. During culture, an antibiotic such as kanamycin and penicillin may be added to the medium, if necessary.

As a method for expressing the gene encoding the human FGF23, in addition to direct expression, for example, a method such as secretory production or fusion protein expression [Molecular Cloning, A Laboratory Manual, Second Edition, Cold Spring Harbor Laboratory Press (1989)] can be used.

Examples of the method for producing the human FGF23 include a method for producing human FGF23 within a host cell, a method for secreting human FGF23 outside a host cell, and a method for producing human FGF23 on an outer membrane of a host cell. An appropriate method can be selected by changing a host cell to be used and a structure of human FGF23 to be produced.

When human FGF23 is produced within a host cell or on an outer membrane of a host cell, human FGF23 can be actively secreted outside the host cell by using a method of Paulson et al. [J. Biol. Chem., 264, 17619 (1989)], a method of Rowe et al. [Proc. Natl. Acad. Sci., USA, 86, 8227 (1989), Genes Develop., 4, 1288 (1990)], and a method described in JP05-336963A or WO94/23021. A production amount of human FGF23 can also be increased using a gene amplification system (JP2-227075A) using a dihydrofolate reductase gene, or the like.

The obtained human FGF23 can be isolated and purified, for example, as follows. When human FGF23 is expressed in a dissolved state in cells, the cells are collected by centrifugation after the end of the culture, suspended in an aqueous buffer solution, and then disrupted with an ultrasonic disintegrator, a French press, a Manton-Gaurin homogenizer, a Dyno mill, or the like to obtain a cell-free extract. From a supernatant obtained by centrifuging the cell-free extract, a purified specimen can be obtained by using a general protein isolation and purification method, that is, a method such as a solvent extraction method, a salting-out method with ammonium sulfate or the like, a desalting method, a precipitation method with an organic solvent, diethylaminoethyl (DEAE)-Sepharose, an anion exchange chromatography method using a resin such as DIAION HPA-75 (manufactured by Mitsubishi Chemical Corporation), a cation exchange chromatography method using a resin such as S-Sepharose FF (manufactured by Pharmacia), a hydrophobic chromatography method using a resin such as butyl sepharose and phenyl sepharose, a gel filtration method using molecular sieves, an affinity chromatography method, a chromatofocusing method, and an electrophoresis method such as isoelectric focusing, alone or in combination.

When human FGF23 is expressed in an insoluble form in cells, the cells are collected and disrupted in the same manner as above, and centrifuged to collect an insoluble form of human FGF23 as a precipitate fraction. The collected insoluble form of human FGF23 is solubilized with a protein denaturant. After recovering human FGF23 to a normal three-dimensional structure by diluting or dialyzing the solubilized solution, a purified specimen of a polypeptide can be obtained by an isolation and purification method same as that described above.

When human FGF23 or a derivative such as a glycosylated derivative thereof is secreted extracellularly, the human FGF23 or the derivative such as a glycosylated derivative thereof can be collected in a culture supernatant. A soluble fraction can be obtained by processing the culture using a method such as centrifugation same as that described above, and a purified specimen can be obtained from the soluble fraction by using an isolation and purification method same as that described above.

The human FGF23 used in the present invention can also be produced by a chemical synthesis method such as an Fmoc method or a tBoc method. The human FGF23 can be produced by chemical synthesis using a peptide synthesizer manufactured by Advanced ChemTech Inc., PerkinElmer, Pharmacia, Protein Technology Instruments, Synthecell-Vega, Perceptiv, or Shimadzu.

(2) Animal Immunization and Preparation of Antibody-producing Cells for Fusion

Animals such as mice, rats, or hamsters aged 3 weeks to 20 weeks are immunized with the antigen obtained in (1), and antibody-producing cells in spleens, lymph nodes, and peripheral blood of the animals are collected. A mouse FGF23 knockout mouse can also be used as an immunized animal.

The immunization is performed by administering an antigen into subcutaneous, vein, or abdominal cavity of an animal together with, for example, a suitable adjuvant such as complete Freund's adjuvant or aluminum hydroxide gel and Bordetella pertussis vaccine. When the antigen is a partial peptide, a conjugate with a carrier protein such as a bovine serum albumin (BSA) or a keyhole limpet hemocyanin (KLH) is prepared and used as an immunogen.

After the first administration, the antigen is administered 5 times to 10 times every 1 week to 2 weeks. Blood is collected from a fundus venous plexus 3 days to 7 days after each administration, and an antibody titer of the serum thereof is measured using enzyme immunoassay [Antibodies-A Laboratory Manual, Cold Spring Harbor Laboratory (1988)] or the like. An animal whose serum exhibits a sufficient antibody titer against the antigen used for immunization is used as a supply source of antibody-producing cells for fusion.

Tissues containing antibody-producing cells, such as a spleen, are excised from the immunized animal on Day 3 to Day 7 after the final administration of the antigen, and the antibody-producing cells are collected. When using spleen cells, the spleen is shredded and loosened, followed by centrifuging, and then erythrocytes are further removed to obtain antibody-producing cells for fusion.

(3) Preparation of Myeloma Cells

As myeloma cells, an established cell line obtained from a mouse is used, for example, a 8-azaguanine resistant mouse (BALB/c derived) myeloma cell line P3-X63Ag8-U1 (P3-U1) [Current Topics in Microbiology and Immunology, 18, 1 (1978)], P3-NS1/1-Ag41 (NS-1) [European J. Immunology, 6, 511 (1976)], SP2/0-Ag14 (SP-2) [Nature, 276, 269 (1978)], P3-X63-Ag8653 (653) [J. Immunology, 123, 1548 (1979)], and P3-X63-Ag8 (X63) [Nature, 256, 495 (1975)] are used.

The myeloma cells are subcultured in a normal medium (RPMI 1640 medium supplemented with glutamine, 2-mercaptoethanol, gentamycin, FBS, and 8-azaguanine), and subcultured in the normal medium 3 days and 4 days before cell fusion to ensure a cell number of $2 \times 10^7$ or more on the day of fusion.

(4) Cell Fusion and Preparation of Monoclonal Antibody-Producing Hybridomas

The antibody-producing cells for fusion obtained in (2) and the myeloma cells obtained in (3) are thoroughly washed with a Minimum Essential Medium (MEM) or PBS (1.83 g of disodium phosphate, 0.21 g of potassium linate, 7.65 g of sodium chloride, 1 liter of distilled water, pH 7.2), and mixed such that the number of cells of antibody-producing cells for fusion: myeloma cells=5:1 to 10:1, followed by performing centrifugation and then removing a supernatant. After thoroughly loosening a precipitated cell group, a mixed solution of polyethylene glycol-1000 (PEG-1000), a MEM medium, and dimethyl sulfoxide is added thereto at 37° C. while stirring. Further, 1 mL to 2 mL of the MEM medium is added several times every 1 minute to 2 minutes, and then the MEM medium is added to make a total amount to 50 mL. After centrifugation, the supernatant is removed. After gently loosening the precipitated cell group, the cells are gently suspended in a HAT medium [normal medium containing hypoxanthine, thymidine, and aminopterin] as antibody-producing cells for fusion. The suspension is cultured at 37° C. for 7 days to 14 days in a 5% $CO_2$ incubator.

After culturing, a part of the culture supernatant is removed, and a cell group that reacts to an antigen containing the human FGF23 and does not react to an antigen not containing the human FGF23 is selected using a hybridoma selection method such as a binding assay to be described later. Next, cloning is performed by a limiting dilution method, and hybridomas with stable and strong antibody titers are selected as monoclonal antibody-producing hybridomas.

(5) Preparation of Purified Monoclonal Antibody

The monoclonal antibody-producing hybridomas obtained in (4) are intraperitoneally injected into mice or nude mice aged 8 weeks to 10 weeks and treated with pristane [intraperitoneally administered with 0.5 mL of 2,6,10,14-tetramethylpentadecane (pristane) and kept for 2 weeks]. The hybridomas turn into ascites cancer in 10 days to 21 days. An ascites fluid is collected from the mice, centrifuged to remove solids, followed by salting out with 40% to 50% ammonium sulfate and purifying using a caprylic acid precipitation method, a DEAE-Sepharose column, a Protein A column, or a gel filtration column, and IgG or IgM fractions are collected and used as purified monoclonal antibodies.

After culturing the monoclonal antibody-producing hybridomas obtained in (4) in an RPMI1640 medium supplemented with 10% FBS, the supernatant is removed by centrifugation, and the resultant is suspended in a Hybridoma SFM medium, followed by culturing for 3 days to 7 days. The obtained cell suspension can be centrifuged, the supernatant can be purified by a protein A column or a protein G column, an IgG fraction can be collected to obtain purified monoclonal antibodies. To the Hybridoma SFM medium, 5% Daigo GF21 can also be added.

Determination of the antibody subclass is performed by enzyme immunoassay using a subclass typing kit. Quantification of a protein amount is calculated by a Lowry method or absorbance at 280 nm.

(6) Selection of Monoclonal Antibody

The selection of the monoclonal antibody is performed by measuring the binding ability of the antibody to human FGF23 using ELISA as described below.

After the human FGF23 is dispensed into a plate such as a 96-well plate, a test substance as a first antibody, such as serum, a culture supernatant of hybridoma, or a purified monoclonal antibody, is dispensed and reacted. Next, the plate is thoroughly washed with PBS or the like, and then an anti-immunoglobulin antibody labeled with an enzyme reagent or the like as a second antibody is dispensed and allowed to react. Thereafter, the plate is thoroughly washed with PBS or the like, and then a substrate is added and an absorption coefficient of each well is measured with a plate reader to select a monoclonal antibody that specifically reacts with human FGF23.

2. Preparation of Recombinant Antibody

As an example of producing the recombinant antibody, a method for producing a human chimeric antibody and a humanized antibody is shown below. A recombinant mouse antibody, rat antibody, or rabbit antibody can also be produced by a similar method.

(1) Construction of Recombinant Antibody Expression Vector

A recombinant antibody expression vector is an animal cell expression vector incorporated with DNAs each encoding a CH and a CL of a human antibody, and can be constructed by cloning DNAs each encoding a CH and a CL of a human antibody into an animal cell expression vector, respectively.

As a C region of the human antibody, a CH and a CL of any human antibody can be used. For example, a CH of γ1 subclass and a CL of κ class of a human antibody are used. A cDNA is used as the DNAs each encoding a CH and a CL of a human antibody, and a chromosomal DNA consisting of exon and intron can also be used. Any animal cell expression vector can be used as long as it can incorporate and express a gene encoding the C region of the human antibody. For example, pAGE107 [Cytotechnol., 3, 133 (1990)], pAGE103 [J. Biochem., 101, 1307 (1987)], pHSG274 [Gene, 27, 223 (1984)], pKCR [Proc. Natl. Acad. Sci. USA, 78, 1527 (1981)], pSG1bd2-4 [Cytotechnol., 4, 173 (1990)], or pSEIUK1Sed1-3 [Cytotechnol., 13, 79 (1993)] is used. Examples of a promoter and an enhancer for the animal cell expression vector include an SV40 early promoter [J. Biochem., 101, 1307 (1987)], a moloney murine leukemia virus LTR [Biochem. Biophys. Res. Commun., 149, 960 (1987)], or an immunoglobulin H chain promoter [Cell, 41, 479 (1985)], an enhancer [Cell, 33, 717 (1983)].

As the recombinant antibody expression vector, a recombinant antibody expression vector of a type (tandem type) in which an antibody H chain and L chain are present on the same vector [J. Immunol. Methods, 167, 271 (1994)] is used, from the viewpoint of ease of construction of a recombinant antibody expression vector, ease of introduction into animal cells, and a balance of expression levels of the antibody H chain and L chain in animal cells, and a recombinant antibody expression vector of a type in which the antibody H chain and L chain are present on separate vectors can also be used. As a tandem type recombinant antibody expression vector, pKANTEX93 (WO97/10354), pEE18 [Hybridoma, 17, 559 (1998)], and the like are used.

(2) Acquisition of cDNA Encoding V Region of Antibody Derived from Non-Human Animal and Analysis of Amino Acid Sequence Acquisition of a cDNA encoding a VH and a VL of a non-human antibody and analysis of an amino acid sequence can be performed as follows.

An mRNA is extracted from a non-human antibody-producing hybridoma cell to synthesize a cDNA. The synthesized cDNA is cloned into a vector such as a phage or a plasmid to prepare a cDNA library. From the library, a recombinant phage or a recombinant plasmid comprising the cDNA encoding the VH or the VL is isolated using, as a probe, a DNA encoding a C region portion or a V region portion of a mouse antibody. A total nucleotide sequence of a VH or a VL of the target mouse antibody on the recombinant phage or the recombinant plasmid is determined, and a total amino acid sequence of the VH or the VL is estimated based on the nucleotide sequence.

As a non-human animal for producing non-human antibody-producing hybridoma cells, mice, rats, hamsters, rabbits, and the like are used, and any animal can be used as long as hybridoma cells can be produced.

For preparation of a total RNA from the hybridomas cell, a guanidine thiocyanate method [Methods in Enzymol, 154, 3 (1987)] or a kit such as an RNA easy kit (manufactured by Qiagen) is used.

For preparation of an mRNA from the total RNA, an oligo (dT) immobilized cellulose column method [Molecular Cloning, A Laboratory Manual, Second Edition, Cold Spring Harbor Laboratory Press (1989)] or a kit such as an Oligo-dT30<Super>mRNA Purification (registered trademark) Kit (manufactured by Takara Bio Inc.) is used. The mRNA can also be prepared from the hybridoma cell using a kit such as a Fast Track mRNA Isolation (registered trademark) Kit (manufactured by Invitrogen) or a QuickPrep mRNA Purification (registered trademark) Kit (manufactured by Pharmacia).

For synthesis of the cDNA and preparation of the cDNA library, a well-known method [Molecular Cloning, A Laboratory Manual, Second Edition, Cold Spring Harbor Laboratory Press (1989), Current Protocols in Molecular Biology. Supplement 1, John Wiley & Sons (1987-1997)], Super-Script Plasmid System for cDNA Synthesis and Plasmid Cloning (manufactured by Invitrogen), or a ZAP-cDNA Synthesis (registered trademark) Kit (manufactured by Stratagene) is used.

When preparing the cDNA library, any vector can be used as long as it can incorporate a cDNA synthesized using an mRNA extracted from a hybridoma cell as a template. For example, ZAP Express [Strategies, 5, 58 (1992)], pBluescript II SK(+) [Nucleic Acids Research, 17, 9494 (1989)], λZAPII (manufactured by Stratagene), Aλgt10, λgt11 [DNA Cloning: A Practical Approach, I, 49 (1985)], Lambda BlueMid (manufactured by Clontech), λExCell, pT7T3-18U (manufactured by Pharmacia), pcD2 [Mol. Cell. Biol., 3, 280 (1983)], or pUC18 [Gene, 33, 103 (1985)] is used.

Any *Escherichia coli* that can be used to introduce, express, and maintain the cDNA library constructed using a phage or plasmid vector can be used. For example, XL1-Blue MRF' [Strategies, 5, 81 (1992)], C600 [Genetics, 39, 440 (1954)], Y1088, Y1090 [Science, 222, 778 (1983)], NM522 [J. Mol. Biol., 166, 1 (1983)], K802 [J. Mol. Biol., 16, 118 (1966)], or JM105 [Gene, 38, 275 (1985)] is used.

For selection of a clone of the cDNA encoding a VH or a VL of a non-human antibody from the cDNA library, a colony hybridization method using an isotope- or fluorescently labeled probe, a plaque hybridization method [Molecular Cloning, A Laboratory Manual, Second Edition, Cold Spring Harbor Laboratory Press (1989)], or the like is used.

The cDNA encoding the VH or the VL can also be prepared by preparing primers and performing a Polymerase Chain Reaction method [Molecular Cloning, A Laboratory Manual, Second Edition, Cold Spring Harbor Laboratory Press (1989), Current Protocols in Molecular Biology. Supplement 1, John Wiley & Sons (1987-1997)] using a cDNA synthesized from the mRNA or the cDNA library as a template.

After cleaving the selected cDNA with an appropriate restriction enzyme, or the like, cloning into a plasmid such as pBluescript SK(-) (manufactured by Stratagene) is performed, and a nucleotide sequence of the cDNA is determined by a commonly used nucleotide sequence analysis method. As the nucleotide sequence analysis method, for example, an automatic nucleotide sequence analyzer such as ABI PRISM 3700 (manufactured by PE Biosystems) or an A. L. F. DNA sequencer (manufactured by Pharmacia) is used after performing a reaction such as a dideoxy method [Proc. Natl. Acad. Sci. USA, 74, 5463 (1977)].

By estimating complete amino acid sequences of the VH and the VL from the determined nucleotide sequences, respectively, and comparing with complete amino acid sequences of a VH and a VL of a known antibody [Sequences of Proteins of Immunological Interest, US Dept. Health and Human Services (1991)], it is confirmed whether the obtained cDNA encodes the complete amino acid sequence of each VH and VL of the antibody, which comprises a secretory signal sequence. Regarding the complete amino acid sequence of each VH and VL of the antibody, which includes a secretory signal sequence, by comparing with complete amino acid sequences of a VH and a VL of a known antibody [Sequences of Proteins of Immunological Interest, US Dept. Health and Human Services (1991)], a length and an N-terminal amino acid sequence of the secretory signal sequence can be estimated, and further, the subgroup to which they belong can be identified. Amino acid sequences of CDRs of the VH and the VL can be found by comparing with amino acid sequences of a VH and a VL of a known antibody [Sequences of Proteins of Immunological Interest, US Dept. Health and Human Services (1991)].

Using the obtained complete amino acid sequences of the VH and the VL, a homology search by a BLAST method [J. Mol. Biol., 215, 403 (1990)] using any database such as SWISS-PROT or PIR-Protein is performed, and it can be confirmed whether the complete amino acid sequences of the VH and the VL are novel.

(3) Construction of Human Chimeric Antibody Expression Vector or Modified Human Chimeric Antibody Expression Vector A human chimeric antibody expression vector can be constructed by cloning the cDNA encoding the VH or the VL of the non-human antibody upstream of each gene encoding a CH or a CL of the human antibody on the recombinant antibody expression vector obtained in (1).

In order to link a 3' end side of the cDNA encoding the VH or the VL of the non-human antibody and a 5' end side of the CH or the CL of a human antibody, cDNAs of a VH and a VL are prepared in such a way that a nucleotide sequence of a linking portion encodes an appropriate amino acid and is an appropriate restriction enzyme recognition sequence. The prepared cDNAs of the VH and the VL are cloned, respectively, upstream of each gene encoding the CH or the CL of the human antibody on the recombinant antibody expression vector obtained in (1) such that they are expressed in an appropriate form, and a human chimeric antibody expression vector is constructed.

The cDNA encoding the VH or the VL of the non-human antibody can be amplified by PCR using a synthetic DNA having recognition sequences for appropriate restriction enzymes at both ends, and the cDNA can be cloned into the recombinant antibody expression vector obtained in (1).

(4) Construction of cDNA Encoding V Region of Humanized Antibody

A cDNA encoding a VH or a VL of a humanized antibody can be constructed as follows.

An amino acid sequence of an FR of a VH or a VL of a human antibody is selected for grafting an amino acid sequence of CDR of a VH or a VL of a non-human antibody. The selected amino acid sequence of the FR may be any amino acid sequence derived from a human antibody. For example, an amino acid sequence of an FR of a human antibody registered in a database such as a Protein Data Bank, or a common amino acid sequence of each subgroup of an FR of a human antibody [Sequences of Proteins of Immunological Interest, US Dept. Health and Human Services (1991)] is used. In order to suppress a decrease in binding activity of the antibody, the amino acid sequence of an FR having as high a homology as possible (at least 60% or more) with the amino acid sequence of a VH or a VL of an original antibody is selected.

Next, an amino acid sequence of CDR of the original antibody is grafted to the amino acid sequence of the FR of the VH or the VL of the selected human antibody to design an amino acid sequence of a VH or a VL of a humanized antibody. By converting the designed amino acid sequence into a DNA sequence in consideration of the usage frequency of codons found in the nucleotide sequence of an antibody gene [Sequences of Proteins of Immunological Interest, US Dept. Health and Human Services (1991)], a cDNA sequence encoding an amino acid sequence of a VH or a VL of a humanized antibody is designed.

Based on the designed DNA sequence, several synthetic DNAs having a length of about 100 bases are synthesized, and a PCR reaction is performed using the synthesized DNA. In this case, six synthetic DNAs are preferably designed for each of VH and VL in view of the reaction efficiency in the PCR reaction and the length of DNA that can be synthesized. Furthermore, by introducing recognition sequences of appropriate restriction enzymes into the 5' or 3' ends of the synthetic DNA located at both ends, a cDNA encoding the VH or the VL of the humanized antibody can be easily cloned into the recombinant antibody expression vector obtained in (1).

After the PCR reaction, each amplified product was cloned into a plasmid such as pBluescript SK(−) (manufactured by Stratagene), and a nucleotide sequence is determined by a method same as that described in (2) to obtain a plasmid having a DNA sequence encoding an amino acid sequence of a VH or a VL of a desired humanized antibody.

Based on the designed DNA sequence, a DNA synthesized using each of the full length of the VH and the full length of the VL as one long chain DNA can be used instead of the PCR amplification product. Furthermore, by introducing the recognition sequence for an appropriate restriction enzyme at both ends of the synthetic long chain DNA, a cDNA encoding the VH or the VL of the humanized antibody can be easily cloned into the recombinant antibody expression vector obtained in (1).

(5) Modification of Amino Acid Sequence of V Region of Humanized Antibody

When only CDRs of a VH and a VL of a non-human antibody are grafted onto the FRs of the VH and the VL of the human antibody, the antigen binding activity of the humanized antibody is lower than that of the original non-human antibody [BIO/TECHNOLOGY, 9, 266 (1991)]. In the humanized antibody, by identifying, among the amino acid sequences of the FRs of the VH and the VL of the human antibody, an amino acid residue directly associated with binding to an antigen, an amino acid residue interacting with an amino acid residue of CDR, and an amino acid residue maintaining a three-dimensional structure of an antibody and indirectly associated with binding to an antigen, and substituting those amino acid residues with amino acid residues of the original non-human antibody, the reduced antigen binding activity can be increased.

In order to identify the FR amino acid residues associated with the antigen binding activity, the three-dimensional structure of the antibody can be constructed and analyzed by using X-ray crystal analysis [J. Mol. Biol., 112, 535 (1977)], computer modeling [Protein Engineering, 7, 1501 (1994)], or the like. A humanized antibody having a necessary antigen binding activity can be obtained by preparing several types of modified antibodies for each antibody, repeatedly examining each correlation with the antigen binding activity, and performing trial and error.

The amino acid residues of the FRs of the VH and the VL of the human antibody can be modified by performing the PCR reaction described in (4) using a synthetic DNA for modification. The nucleotide sequence of the amplified product after the PCR reaction is determined by the method described in (2) to confirm that the desired modification is made.

(6) Construction of Humanized Antibody Expression Vector

By cloning the cDNA encoding the VH or the VL of the constructed recombinant antibody upstream of the gene encoding the CH or the CL of the human antibody in the recombinant antibody expression vector obtained in (1), a humanized antibody expression vector can be constructed.

For example, by introducing recognition sequences for appropriate restriction enzymes to the 5' or 3' ends of the synthetic DNA used in constructing the VH and the VL of the humanized antibody obtained in (4) and (5) at both ends, respectively, the synthetic DNA is cloned upstream of the gene encoding the CH or the CL of the human antibody in the recombinant antibody expression vector obtained in (1) such that the synthetic DNA is expressed in an appropriate form.

When producing a recombinant antibody such as the above-described chimeric antibody or humanized antibody, a VL-substituted chimeric antibody expression vector can be constructed by preparing an antibody expression vector in which the H chain (or VH) and L chain (or VL) derived from two different types of antibodies are recombined.

(7) Transient Expression of Recombinant Antibody

Using the recombinant antibody expression vectors obtained in (3) and (6) or an expression vector modified therefrom, transient expression of a recombinant antibody can be performed, and the antigen binding activity of produced various types of chimeric antibody and humanized antibody can be efficiently evaluated.

Any host cell that can express a recombinant antibody can be used as the host cell into which the expression vector is to be introduced, and for example, COS-7 cells [American Type Culture Collection (ATCC) number: CRL1651] are used [Methods in Nucleic Acids Res., CRC press, 283 (1991)].

For introduction of the expression vector into COS-7 cells, a DEAE-dextran method [Methods in Nucleic Acids Res., CRC press (1991)], or a lipofection method [Proc. Natl. Acad. Sci. USA, 84, 7413 (1987)] is used.

After introduction of the expression vector, an expression level and an antigen binding activity of the recombinant antibody in a culture supernatant are measured using enzyme immunoassay [Monoclonal Antibodies-Principles and practice, Third edition, Academic Press (1996), Antibodies-A Laboratory Manual, Cold Spring Harbor Laboratory (1988), Monoclonal Antibody Laboratory Manual, Kodansha Scientific (1987)], and the like.

(8) Acquisition of Transformant Stably Expressing Recombinant Antibody and Preparation of Recombinant Antibody By introducing the recombinant antibody expression vectors or the modified expression vectors thereof obtained in (3) and (6) into appropriate host cells, transformants that stably express the recombinant antibody can be obtained.

An electroporation method [JP2-257891A, Cytotechnology, 3, 133 (1990)] is used to introduce the expression vector into a host cell.

Any host cell that can express the recombinant antibody can be used as the host cell into which the recombinant antibody expression vector is to be introduced. For example, CHO-K1 (ATCC CCL-61), DUKXB11 (ATCC CCL-9096), Pro-5 (ATCC CCL-1781), CHO-S (Life Technologies, Cat #11619), rat myeloma cells YB2/3HL.P2. G11.16Ag. 20 (ATCC No.: CRL1662, or also referred to as YB2/0), mouse myeloma cells NSO, mouse myeloma cells SP2/0-Ag14 (ATCC No.: CRL1581), mouse P3X63-Ag8.653 cells (ATCC No.: CRL1580), and CHO cells (CHO/DG44 cells) from which a dihydrofolate reductase gene (hereinafter, referred to as dhfr) is deleted [Proc. Natl. Acad. Sci. USA, 77, 4216 (1980)] are used.

A host cell in which an activity of a protein such as an enzyme associated with synthesis of intracellular sugar nucleotide GDP-fucose, a protein such as an enzyme associated with sugar chain modification in which 1-position of fucose α-binds to 6-position of N-acetylglucosamine at a reducing end of an N-glycoside-linked complex sugar chain, a protein associated with transport of intracellular sugar nucleotide GDP-fucose to a Golgi body is reduced or deleted, for example, CHO cells from which an α1,6-fucosyltransferase gene is deleted (WO2005/035586, WO02/31140), or Lec13 with acquired lectin resistance [Somatic Cell and Molecular genetics, 12, 55 (1986)] can also be used.

After introduction of the expression vector, a transformant that stably expresses the recombinant antibody is selected by performing culture in an animal cell culture medium containing a drug such as G418 sulfate (hereinafter, referred to as G418) (JP2-257891A).

Examples of the animal cell culture medium include a RPMI 1640 medium (manufactured by Invitrogen), a GIT medium (manufactured by Japan Pharmaceutical Co., Ltd.), an EX-CELL 301 medium (manufactured by JRH Co., Ltd.), an IMDM medium (manufactured by Invitrogen), a Hybridoma-SFM medium (manufactured by Invitrogen), and a medium supplemented with various additives such as FBS. The obtained transformant is cultured in a medium to express and accumulate the recombinant antibody in the culture supernatant. An expression level and an antigen binding activity of the recombinant antibody in the culture supernatant can be measured by ELISA or the like. The expression level of the recombinant antibody produced by the transformant can be increased by using a dhfr amplification system (JP2-257891A), or the like.

The recombinant antibody can be purified from the culture supernatant of the transformant using a protein A column [Monoclonal Antibodies-Principles and practice, Third edition, Academic Press (1996), Antibodies-A Laboratory Manual, Cold Spring Harbor Laboratory (1988)]. Alternatively, methods used for protein purification, such as gel filtration, ion exchange chromatography, and ultrafiltration can be combined.

A molecular weight of the H chain, the L chain, or the entire antibody molecule of the purified recombinant antibody can be measured using polyacrylamide gel electrophoresis [Nature, 227, 680 (1970)], Western blotting [Monoclonal Antibodies-Principles and practice, Third edition, Academic Press (1996), Antibodies-A Laboratory Manual, Cold Spring Harbor Laboratory (1988)], or the like.

3. Activity Evaluation of Purified Monoclonal Antibody or Antibody Fragment Thereof An activity of the purified monoclonal antibody or the antibody fragment thereof of the present invention can be evaluated as follows.

The binding activity of the antibody or the antibody fragment thereof of the present invention to human FGF23 can be measured by ELISA, a surface plasmon resonance method, or the like.

The human FGF23 neutralizing activity of the antibody or the antibody fragment thereof of the present invention can be measured using the above-described reporter assay or the like.

4. Therapeutic Method for Disease Using Anti-human FGF23 Monoclonal Antibody or Antibody Fragment Thereof of Present Invention The monoclonal antibody or the antibody fragment thereof of the present invention can be used for treatment of a disease associated with human FGF23.

The therapeutic agent containing the monoclonal antibody or the antibody fragment thereof of the present invention may contain only the antibody or the antibody fragment thereof as an active ingredient, and the therapeutic agent can be mixed together with one or more pharmacologically acceptable carriers and provided as a pharmaceutical formulation prepared by a method known in the pharmaceutical art.

Examples of the administration route include oral administration, and parenteral administration such as buccal, tracheobronchial, intrarectal, subcutaneous, intramuscular, or intravenous administration. Examples of a dosage form include sprays, capsules, tablets, powders, granules, syrups, emulsions, suppositories, injections, ointments, and tapes.

Examples of the preparation suitable for oral administration include an emulsion, a syrup, a capsule, a tablet, a powder, and a granule.

A liquid preparation such as an emulsion or a syrup can be produced using, as an additive, water, sugars such as sucrose, sorbitol or fructose, glycols such as polyethylene glycol or propylene glycol, oils such as sesame oil, olive oil, or soybean oil, antiseptics such as a p-hydroxybenzoic acid ester, or flavors such as strawberry flavor or peppermint.

The capsule, the tablet, the powder, the granule, and the like can be produced using, as an additive, an excipient such as lactose, glucose, sucrose, or mannitol, a disintegrator such as starch or sodium alginate, a lubricant such as magnesium stearate or talc, a binder such as polyvinyl alcohol, hydroxypropyl cellulose, or gelatin, a surfactant such as a fatty acid ester, or a plasticizer such as glycerin.

Examples of the preparation suitable for parenteral administration include an injection, suppository, and a spray. The injection can be produced using a salt solution, a glucose solution, or a carrier formed of a mixture of both. The suppository can be produced using a carrier such as cacao butter, hydrogenated aliphatic, or carboxylic acid.

The spray can be produced using a carrier that does not stimulate the oral cavity and the respiratory tract mucosa of a recipient and that allows the monoclonal antibody and the antibody fragment thereof of the present invention to be dispersed as fine particles and facilitate absorption. Examples of the carrier include lactose and glycerin. The preparation can also be produced as an aerosol or a dry powder. Further, a component shown as an additive in an appropriate preparation for oral administration can also be added to the above parental agent.

5. Diagnosis Method for Disease Using Anti-human FGF23 Monoclonal Antibody or Antibody Fragment thereof of Present Invention The disease associated with human FGF23 can be diagnosed by using the monoclonal antibody or the antibody fragment thereof of the present invention to detect or measure human FGF23.

Diagnosis of a disease associated with human FGF23 can be performed, for example, by detecting or measuring human FGF23 present in the patient body by an immunological method.

The immunological technique is a method of detecting and measuring an antibody amount or an antigen amount by using an antigen or an antibody subjected to labeling. Examples thereof include a radiolabeled immunoantibody method, enzyme immunoassay, fluorescence immunoassay, luminescent immunoassay, Western blotting, or a physicochemical method.

In the radiolabeled immunoantibody method, for example, an antigen, a cell expressing an antigen, or the like is allowed to react with the antibody or the antibody fragment thereof of the present invention, followed by further allowing to react with a radiolabeled anti-immunoglobulin antibody or an antibody fragment thereof, and then measurement is performed using a scintillation counter or the like.

In the enzyme immunoassay, for example, an antigen, a cell expressing an antigen, or the like is allowed to react with the antibody or the antibody fragment thereof of the present invention, followed by further allowing to react with an anti-immunoglobulin antibody and a binding fragment labeled with an enzyme, or the like, and then a substrate is added and an absorbance of the reaction solution is measured using an absorptiometer. For example, sandwich ELISA is used. As a labeling material to be used in the enzyme immunoassay method, a known enzyme label [Enzyme Immunoassay, Igaku Shoin (1987)] can be used.

For example, an alkaline phosphatase label, a peroxidase label, a luciferase label, or a biotin label is used. The sandwich ELISA is a method in which an antibody is conjugated to a solid phase, then an antigen to be detected or measured is trapped, and a second antibody is allowed to react with the trapped antigen. In the ELISA, two types of antibodies or antibody fragments that recognize the antigen to be detected or measured and have different antigen recognition sites are prepared, and among them, a first antibody or an antibody fragment thereof is adsorbed onto a plate (for example, a 96-well plate) in advance, and then a second antibody or an antibody fragment thereof is labeled with a fluorescent substance such as FITC, an enzyme such as peroxidase, or biotin. Cells isolated from a living body or a lysate thereof, tissues or a lysate thereof, cell culture supernatant, serum, a pleural fluid, an ascites fluid, or an eye fluid is allowed to react with the plate to which the above antibody is adsorbed, followed by allowing to react with a labeled monoclonal antibody or an antibody fragment to perform a detection reaction depending on the labeling substance. An antigen concentration in a test sample is calculated from a calibration curve prepared by stepwise diluting a known antigen. As the antibody used in the sandwich ELISA method, either a polyclonal antibody or a monoclonal antibody may be used, and an antibody fragment such as Fab, Fab', or $F(ab')_2$ may be used. The combination of two types of antibodies used in the sandwich ELISA may be a combination of monoclonal antibodies that recognize different epitopes and antibody fragments thereof, or a combination of a polyclonal antibody and a monoclonal antibody or an antibody fragment thereof.

For the fluorescence immunoassay, for example, a method described in the literature [Monoclonal Antibodies-Principles and practice, Third edition, Academic Press (1996), Monoclonal Antibody Experiment Manual, Kodansha Scientific (1987)] is used. As the labeling material used in the fluorescence immunoassay, a known fluorescent label [Fluorescent Antibody Method, Soft Science Co., Ltd. (1983)] can be used. For example, FITC or RITC is used.

For the luminescent immunoassay, for example, the measurement is performed by a method described in, for example, the literature [Bioluminescence, Chemiluminescence Clinical Examination 42, Hirokawa Shoten (1998)]. Examples of the labeling material used in the luminescent immunoassay include a known luminescent label. Acridinium ester or lophine is used.

For the Western blotting, after fractionating antigens or cells expressing the antigens using SDS (sodium dodecyl sulfate)-PAGE (polyacrylamide gel) [Antibodies-A Laboratory Manual Cold Spring Harbor Laboratory (1988)], the gel is blotted onto a polyvinylidene difluoride (PVDF) membrane or a nitrocellulose membrane, the membrane is allowed to react with an antibody or an antibody fragment thereof that recognizes the antigen, followed by further allowing to react with an anti-mouse IgG antibody or a binding fragment labeled with a fluorescent substance such as FITC, an enzyme label such as peroxidase, or a biotin label, and then measurement is performed by visualizing the label.

The physicochemical method is performed, for example, by binding human FGF23 as an antigen to the monoclonal antibody of the present invention or the antibody fragment thereof to form an aggregate and detecting the aggregate. As the physicochemical method, a capillary method, a single radial immunodiffusion method, turbidimetric inhibition immunoassay, or latex turbidimetric inhibition immunoassay [Clinical Testing Projection, Kanehara (1998)] can also be used. In the latex turbidimetric inhibition immunoassay, when a carrier such as polystyrene latex with a particle size of about 0.1 μm to 1 μm that is sensitized with an antibody or antigen is used and an antigen-antibody reaction is caused by the corresponding antigen or antibody, scattered light in the reaction solution increases and transmitted light decreases. By detecting this change as absorbance or integrating sphere turbidity, the antigen concentration in the test sample is measured.

Hereinafter, the present invention will be specifically explained with reference to Examples, but the present invention is not limited to the following Examples.

EXAMPLE

[Example 1] Detection of Degradation Product of Antibody A

The amino acid sequence of the heavy chain variable region of the anti-human FGF23 antibody described in WO2008/099969 is represented by SEQ ID NO: 1, and the amino acid sequence of the light chain variable region of the antibody is represented by SEQ ID NO: 2. Hereinafter, a human IgG1 antibody comprising a VH comprising the amino acid sequence represented by SEQ ID NO: 1 and a VL comprising the amino acid sequence represented by SEQ ID NO: 2 will be referred to as an antibody A.

The antibody A was prepared in the same manner as in Example 2, and a solvent of the antibody solution was replaced with a solvent at pH 4 containing 10 mM sodium L-glutamate, 262 mM D-sorbitol, and 0.05 mg/mL Polysyrate 80. The obtained antibody solution was allowed to stand at 40 degrees for one month (hereinafter, referred to as a 40 degrees 1M specimen) or at −80 degrees for one month, and then thawed (hereinafter, referred to as an initial specimen).

Thereafter, SEC analysis and SDS-PAGE under reduction conditions were performed using the 40 degrees 1M specimen and the initial specimen. As a result of SEC analysis, in the initial specimen, a peak corresponding to a degradation product of the antibody showed about 3%, while in the 40 degrees 1M specimen, the peak showed 9.32%.

As a result of SDS-PAGE, as compared with the initial specimen, in the 40 degrees 1M specimen, a band (a band A) located at a size smaller by about 10 kDa than that of the H chain at about 50 kDa is significantly darker, and in correlation with this, the H chain band was fainter. Accordingly, it was suggested that the band A was the band of the degradation product of the H chain, and the 40 degrees 1M specimen was degraded in the H chain. As a result of analyzing the N-terminal amino acid sequence of the band A, it was confirmed that the heavy chain variable region of the antibody A was cleaved at D at position 99 and I at position 100.

[Example 2] Preparation of Modified Antibody I100

For the antibody A, an antibody in which I which is the amino acid residue at position 100 of the amino acid sequence represented by SEQ ID NO: 1 in the VH was substituted with the amino acid residue described in Table 1 was prepared by a method described below. Hereinafter, some or all of the antibodies listed in Table 1 will also be referred to as a modified antibody I100.

TABLE 1

| Antibody name | Amino acid substituted to I100 | Amino acid sequence of heavy chain variable region |
|---|---|---|
| I100A | A | SEQ ID NO: 3 |
| I100L | L | SEQ ID NO: 4 |
| I100V | V | SEQ ID NO: 5 |
| I100Y | Y | SEQ ID NO: 6 |
| I100W | W | SEQ ID NO: 7 |
| I100T | T | SEQ ID NO: 8 |
| I100S | S | SEQ ID NO: 9 |
| I100R | R | SEQ ID NO: 10 |
| I100Q | Q | SEQ ID NO: 11 |
| I100N | N | SEQ ID NO: 12 |
| I100M | M | SEQ ID NO: 13 |
| I100K | K | SEQ ID NO: 14 |
| I100H | H | SEQ ID NO: 15 |
| I100G | G | SEQ ID NO: 16 |
| I100F | F | SEQ ID NO: 17 |
| I100E | E | SEQ ID NO: 18 |
| I100D | D | SEQ ID NO: 19 |

A gene fragment corresponding to a nucleotide sequence encoding an amino acid sequence of a VH of each antibody shown in Table 1 was introduced into an expression vector by using a seamless cloning method (commissioned to FASMAC Co., Ltd.) to prepare a necessary plasmid. The H chain expression vector used was a pCI-OtCAG_hG1 vector comprising a signal sequence and a human γ-chain constant region sequence. In all clones, human IgG1 was used as the H chain constant region.

The amino acid sequence of the VL of the modified antibody I100 used was the amino acid sequence of the VL of the antibody A (SEQ ID NO: 2). The L chain expression vector used was a pCI-OtCMV_hK vector having a signal sequence and a human κ-chain constant region sequence. The completed plasmid was prepared in large amount using a QIAGEN Plasmid Maxi kit (QIAGEN).

Next, each antibody was transiently expressed using an Expi293 Expression System Kit (Life Technologies). The method for introducing the plasmid was in accordance with the attached document. The L chain expression vector and the H chain expression vector were mixed at a ratio of 1:2 and introduced. Cells into which the plasmid was introduced were cultured under conditions of 37 degrees, 5% $CO_2$, and 125 rpm for 3 days. Thereafter, a cell culture suspension was centrifuged, and a culture supernatant was collected through a 0.2 μm filter (Thermo Scientific). A purified antibody was obtained from the culture supernatant by affinity purification using Mab Select SuRe (GE Healthcare).

Specifically, the resin filled in the column was equilibrated with PBS, and then the culture supernatant was added to the column. The column was washed twice with PBS, once each with Wash buffer 1 (PBS with 1M NaCl) and Wash buffer 2 (20 mM citric acid, 50 mM NaCl, pH 5.0), and then the antibody was eluted using an elution buffer (20 mM citric acid, 50 mM NaCl, pH 3.4).

The obtained antibody solution was neutralized by adding 1/10 amount of neutralization buffer (1 M phosphoric acid-NaOH, pH 7.0), and a solvent of the antibody solution was replaced with PBS using NAP25 (GE Healthcare). The antibody solution after the buffer replacement was concentrated by ultrafiltration using Amicon Ultra-4 Centrifugal Filter Units (Millipore), and an absorbance A280 was measured using Nanodrop (Thermo Fisher Scientific), and concentration measurement and adjustment of the antibody solution were performed. An absorption coefficient was calculated based on the amino acid sequence of each humanized antibody according to a method by C. N. Pace et al (1995, Prot. Sci. 4: 2411-2423).

[Example 3] Evaluation of Antigen Binding Activity of Modified Antibody I100

With respect to the modified antibody I100 and the antibody A obtained in Example 2, a binding activity to Recombinant Human FGF-23 (R&D Systems, Cat No. 2604-FG-025/CF) was measured as follows.

Using a Human Antibody Capture Kit (Global Life Sciences Technologies Japan K.K., Cat. No. BR-1008-39), the anti-human IgG antibody was immobilized on a CM5 sensor chip (Global Life Sciences Technologies Japan K.K., Cat. No. BR100530) according to the attached protocol.

An antibody prepared at 1 μg/mL was added to a flow cell on which the Anti-human IgG antibody was immobilized at a flow rate of 10 μL/min for 30 seconds.

Next, recombinant human FGF-23 was prepared stepwise to five concentrations by two-fold dilution starting from 130.5 ng/mL, and a binding reaction was monitored for 2 minutes and a dissociation reaction was monitored for 10 minutes at a flow rate of 30 μL/min. The measurement was performed using a single cycle method. The obtained sensorgrams were analyzed using Bia Evaluation Software (Global Life Sciences Technologies Japan K.K.), and kinetic constants of the antibodies were calculated. The results of some of the calculated binding rate constant (ka), dissociation rate constant (kd), and dissociation constant [kd1/ka1=$K_D$] of each antibody are shown in Tables 2 and 3. In Table 3, A_1, A_2, and A_3 all refer to the antibody A.

TABLE 2

| Antibody name | ka | kd | KD (M) |
| --- | --- | --- | --- |
| A | 9.12+07 | 4.11E−04 | 4.51E−12 |
| I100A | 4.60E+07 | 6.46E−04 | 1.40E−11 |
| I100L | 1.95E+07 | 2.46E−04 | 1.26E−11 |
| I100V | 1.07E+08 | 5.04E−04 | 4.73E−12 |

TABLE 3

| Antibody name | ka | kd | KD (M) |
| --- | --- | --- | --- |
| A_1 | 5.29E+07 | 1.09E−04 | 2.06E−12 |
| A_2 | 4.21E+07 | 1.10E−04 | 2.60E−12 |
| A_3 | 4.20E+07 | 1.58E−04 | 3.76E−12 |
| I100Y | 2.24E+07 | 4.17E−04 | 1.86E−11 |
| I100A | 2.06E+07 | 5.16E−04 | 2.51E−11 |
| I100H | 6.21E+06 | 4.17E−04 | 6.72E−11 |
| I100N | 7.78E+06 | 7.27E−04 | 9.34E−11 |
| I100G | 8.70E+06 | 1.29E−03 | 1.49E−10 |
| I100D | 1.15E+07 | 2.51E−03 | 2.19E−10 |
| I100R | 9.89E+05 | 2.19E−04 | 2.22E−10 |

It was confirmed from Tables 2 and 3 that almost all of the modified antibodies I100, including the antibody I100A and the antibody I100Y, had reduced antigen binding activity as compared with the antibody A.

In addition, it was also confirmed that the antibodies I100W, I100S, I100K, and I100E had reduced antigen binding activity as compared with the antibody A, and the antibodies I100T, I100Q, I100M, and I100F had an antigen binding activity comparable to that of the antibody A.

[Example 4] Confirmation of Degradation Suppression Effect of Modified Antibody I100

For the modified antibody I100 and the antibody A obtained in Example 2, a solvent of an antibody solution was replaced with a solvent at pH 4 containing 10 mM sodium L-glutamate and 262 mM D-sorbitol using NAP25 (GE Healthcare). The obtained antibody solution was allowed to stand at 40 degrees for one month or two weeks, and then subjected to SDS-PAGE under reducing conditions. Table 4 shows results of comparing a density of a band at about 40 kDa, which corresponds to a degradation product of the antibody, between each antibody and the antibody A. When the density of the band was reduced in the modified antibody as compared with the antibody A, it was determined that the degradation was suppressed in the modified antibody as compared with the antibody A.

Numerical values shown in the column for degradation suppression effect in Table 4 were set as follows. An antibody whose degradation was suppressed as compared with the antibody A was given a numerical value of 1, an antibody whose degradation was comparable to that of the antibody A was given a numerical value of 2, and an antibody whose degradation was promoted as compared with the antibody A was given a numerical value of 3.

TABLE 4

| Antibody name | Degradation suppression effect |
| --- | --- |
| I100A | 1 |
| I100L | 2 |
| I100V | 2 |
| I100Y | 1 |
| I100W | 1 |
| I100T | 2 |
| I100S | 2 |
| I100R | 1 |
| I100Q | 3 |
| I100N | 1 |
| I100M | 1 |
| I100K | 2 |
| I100H | 1 |
| I100G | 1 |
| I100F | 2 |
| I100E | 2 |
| I100D | 1 |

As shown in Table 4, the degradation of I100A, I100Y, I100W, I100R, I100N, I100M, I100H, I100G, and I100D was suppressed as compared with the antibody A. I100L, I100V, I100T, I100S, I100K, I100F, and I100E were degraded to an extent comparable to that of the antibody A. The degradation of I100Q was promoted as compared with the antibody A.

[Example 5] Evaluation of Thermal Stability of Antibody A and Modified Antibody I100

Thermal stability of each antibody domain (Fab, CH2, CH3) of the antibody A and the modified antibody I100 was evaluated by differential scanning calorimetry (hereinafter, referred to as DSC).

A measurement sample was prepared to have a concentration of 0.5 mg/mL in a D-PBS buffer. For the measurement, a Micro Cal VP-Capillary DSC system (Spectris Co., Ltd.) was used. The measurement was performed by a program of increasing the temperature from 25 degrees to 100 degrees at one degree per minute. The obtained results are shown in Tables 5 and 6.

TABLE 5

| Antibody name | Fab (degree) | CH2 or Fab + CH2 (degree) | CH3 (degree) |
|---|---|---|---|
| A | 66.8 | 69.3 (CH2) | 82.9 |
| I100A | | 70.0 (Fab + CH2) | 82.9 |
| I100L | 64.3 | 70.1 (CH2) | 83.1 |
| I100V | 67.3 | 71.6 (CH2) | 83.3 |

TABLE 6

| Antibody name | Fab (degree) | CH2 or Fab + CH2 (degree) | CH3 (degree) |
|---|---|---|---|
| A | 66.9 | 69.9 (CH2) | 83.0 |
| I100A | | 70.3 (Fab + CH2) | 83.1 |
| I100D | 65.5 | 70.0 (CH2) | 83.4 |
| I100G | | 70.7 (Fab + CH2) | 83.4 |
| I100H | 69.3 | 72.3 (CH2) | 83.3 |
| I100N | | 71.3 (Fab + CH2) | 83.3 |
| I100R | | 74.3 (Fab + CH2) | 83.4 |
| I100Y | 66.8 | 69.0 (CH2) | 83.5 |

From Tables 5 and 6, in I100A, I100G, I100N, and I100R, a peak of Fab and a peak of CH2 were detected in an overlapping manner, and thermal stability of Fab was improved by 3 degrees to 8 degrees as compared with the antibody A. From the above, it was confirmed that I100A, I100G, I100N, and I100R had structural stability higher than that of the antibody A.

[Example 6] Preparation of Modified Antibody D105

In the same manner as in Example 2, antibodies in which D at position 105 of the amino acid sequence of a VH comprising the amino acid sequence represented by SEQ ID NO: 1 of the antibody A was substituted with the amino acid residues shown in Table 7 (hereinafter, part or all of the antibody is also referred to as modified antibody D105) were prepared.

TABLE 7

| Antibody name | Amino acid substituted to D105 | Amino acid sequence of heavy chain variable region |
|---|---|---|
| D105A | A | SEQ ID NO: 20 |
| D105E | E | SEQ ID NO: 21 |
| D105F | F | SEQ ID NO: 22 |
| D105G | G | SEQ ID NO: 23 |
| D105H | H | SEQ ID NO: 24 |
| D105I | I | SEQ ID NO: 25 |
| D105K | K | SEQ ID NO: 26 |
| D105L | L | SEQ ID NO: 27 |
| D105M | M | SEQ ID NO: 28 |
| D105P | P | SEQ ID NO: 29 |
| D105Q | Q | SEQ ID NO: 30 |
| D105R | R | SEQ ID NO: 31 |
| D105V | V | SEQ ID NO: 32 |
| D105W | W | SEQ ID NO: 33 |
| D105Y | Y | SEQ ID NO: 34 |
| D105T | T | SEQ ID NO: 35 |

TABLE 7-continued

| Antibody name | Amino acid substituted to D105 | Amino acid sequence of heavy chain variable region |
|---|---|---|
| D105N | N | SEQ ID NO: 36 |
| D105S | S | SEQ ID NO: 37 |

[Example 7] Evaluation of Antigen Binding Activity of Modified Antibody D105

With respect to the modified antibodies D105 obtained in Example 6, a binding activity to Recombinant Human FGF-23 (R&D Systems, Cat No. 2604-FG-025/CF) was measured in the same manner as in Example 3. The obtained results are shown in Tables 8 and 9. A_1 and A_2 in Table 8 are both measurement results for the antibody A.

TABLE 8

| Antibody name | ka | kd | KD (M) |
|---|---|---|---|
| A_1 | 3.72E+07 | 1.40E−04 | 3.76E−12 |
| A_2 | 2.96E+07 | 1.23E−04 | 4.15E−12 |
| I100A | 2.13E+07 | 6.17E−04 | 2.89E−11 |
| D105E | 1.29E+07 | 2.18E−04 | 1.70E−11 |
| D105F | 2.65E+06 | 4.72E−04 | 1.78E−10 |
| D105G | 4.84E+06 | 4.72E−04 | 9.75E−11 |
| D105H | 1.19E+06 | 1.70E−04 | 1.43E−10 |
| D105I | 2.50E+06 | 1.83E−04 | 7.34E−11 |
| D105K | 1.73E+06 | 4.53E−04 | 2.62E−10 |
| D105L | 3.39E+06 | 2.17E−04 | 6.39E−11 |
| D105M | 4.54E+05 | 3.05E−04 | 6.71E−10 |
| D105N | 2.92E+06 | 1.34E−04 | 4.60E−11 |
| D105P | 2.51E+06 | 5.04E−04 | 2.01E−10 |
| D105Q | 1.02E+06 | 2.57E−04 | 2.52E−10 |
| D105R | 3.81E+05 | 7.26E−04 | 1.91E−09 |
| D105S | 1.63E+06 | 1.72E−04 | 1.06E−10 |
| D105V | 1.63E+06 | 4.30E−04 | 2.63E−10 |
| D105W | 2.01E+06 | 3.00E−04 | 1.49E−10 |
| D105Y | 3.21E+06 | 3.27E−04 | 1.02E−10 |

TABLE 9

| Antibody name | ka | kd | KD (M) |
|---|---|---|---|
| A | 4.82E+07 | 4.78E−04 | 9.93E−12 |
| D105A | 5.21E+06 | 5.61E−04 | 1.08E−10 |
| D105T | 3.86E+06 | 4.28E−04 | 1.11E−10 |

It was confirmed from Tables 8 and 9 that the antigen binding activity of each of the modified antibodies D105 was reduced as compared with the antibody A.

[Example 8] Confirmation of Degradation Suppression Effect of Modified Antibody D105

For the modified antibodies D105 obtained in Example 6, an antibody degradation suppression effect was confirmed in the same manner as in Example 4. The antibody solution was allowed to stand at 40 degrees for 2 weeks. 10

The obtained results are shown in Table 10. For numerical values shown in the column of the degradation suppression effect in Table 10, an antibody whose degradation was suppressed as compared with the antibody A was given a numerical value of 1, an antibody whose degradation was comparable to that of the antibody A was given a numerical value of 2, and an antibody whose degradation was promoted as compared with the antibody A was given a numerical value of 3.

TABLE 10

| Antibody name | Degradation suppression effect |
|---|---|
| D105E | 2 |
| D105F | 1 |
| D105G | 1 |
| D105H | 1 |
| D105I | 1 |
| D105K | 1 |
| D105L | 1 |
| D105M | 1 |
| D105N | 1 |
| D105P | 1 |
| D105Q | 1 |
| D105R | 1 |
| D105S | 1 |
| D105V | 1 |
| D105W | 1 |
| D105Y | 1 |
| D105A | 1 |
| D105T | 1 |

It was confirmed from Table 10 that degradation of 17 types of modified antibodies D105 except for D105E was suppressed as compared with the antibody A. It was confirmed that, in each of the antibodies, a density of a band at about 40 kDa corresponding to a degradation product of the antibody in SDS-PAGE was significantly reduced as compared with the antibody A, and the degradation of the antibody was significantly suppressed.

[Example 9] Measurement of Neutralizing Activity of Modified Antibody I100 and Modified Antibody D105 to Human FGF23

A neutralizing activity of 24 types of modified antibodies I100 and modified antibodies D105 (100A, I100N, I100G, I100Y, I100R, I100D, I100H, D105A, D105F, D105G, D105H, D105I, D105K, D105L, D105M, D105P, D105Q, D105R, D105V, D105W, D105Y, D105T, D105N, and D105S) in which degradation of the antibody was suppressed as compared with the antibody A in Examples 4 and 8 to human FGF23 was measured by a method described below.

For measurement of the neutralizing activity, a promoter assay was performed using a Klotho stable expression HEK 293 cells (hereinafter, referred to as mEgr1/αKL/HEK293) transformed with a luciferase expression vector comprising a mouse Egr1 gene-derived promoter. The mEgr1/αKL/HEK293 was produced by a method same as that described in Nature 2006 Dec. 7; 444 (7120).

In the promoter assay, when FGF23 binds to αKlotho on the mEgr1/αKL/HEK293, a signal flows in the cell to express a luciferase gene, and fluorescence of the luciferase can be detected. When FGF23 is neutralized by the presence of the FGF23 neutralizing antibody, the fluorescence intensity decreases.

The antibody was diluted to 100 μg/ml with a buffer containing 10 mM sodium L-glutamate and 262 mM D-sorbitol to prepare a stock solution. As a standard culture medium of the mEgr1/αKL/HEK293, a DMEM medium (Thermo fisher) supplemented with 10 (vol %) Fetal Bovine Serum (Thermo fisher) and 1 (vol) % penicillin/streptomycin was used.

The antibody was diluted 1000-fold with the above-described standard culture medium to have a concentration (100 ng/ml) as the highest concentration, and eight dilution series were prepared by √10-fold dilution and used for evaluation. The evaluation was performed using a 384-well plate. The cells were at 2000 cells/well, and the concentration of FGF23 to be added was 4 ng/ml. FGF23 was the same as in Example 3 and diluted with the standard culture medium.

After each antibody was added to cells, the cells were cultured for 24 hours, then FGF23 was added, and the cells were cultured for 4 hours. The fluorescence intensity of luciferase was measured using a Bright-Glo™ Luciferase Assay System (Promega) with a multiplate reader Envision (Perkinelmer).

For the obtained results, the fluorescence intensity at the time of adding FGF23 is 100%, the fluorescence intensity at the time of not adding FGF23 is 0%, and a ratio of the fluorescence intensity at the time of adding each antibody is calculated, and IC50 values (ng/ml) thereof are shown in Table 11.

TABLE 11

| Antibody name | IC50 (ng/mL) |
|---|---|
| A | 1.4 |
| D105A | >100 |
| D105F | >100 |
| D105G | 33.1 |
| D105H | 46.7 |
| D105I | 23.7 |
| D105K | 45.7 |
| D105L | 25.6 |
| D105M | >100 |
| D105N | 14.0 |
| D105P | 99.2 |
| D105Q | >100 |
| D105R | >100 |
| D105S | 27.8 |
| D105T | >100 |
| D105V | >100 |
| D105W | 77.9 |
| D105Y | 21.6 |
| I100A | 5.1 |
| I100D | >100 |
| I100G | >100 |
| I100H | 8.9 |
| I100N | 26.2 |
| I100R | 82.5 |
| I100Y | 3.0 |

As shown in Table 11, all of the modified antibodies had a reduced FGF23 neutralizing activity as compared with the antibody A.

[Example 10] Preparation of Heavy Chain Constant Region Modified Antibody of Antibody A An antibody with modified amino acids in the heavy chain constant region (hereinafter, referred to as CH modified antibody) of the antibody A was prepared by a method described below.

As the CH modified antibody, an isotope antibody in which the CH (human IgG1) of the antibody A is substituted with a CH of human IgG2, IgG2AAAS (a human IgG2 modified antibody in which valine at position 234 is substituted with alanine, glycine at position 237 is substituted with alanine, and proline at position 331 is substituted with serine in the Fc of human IgG2 according to the EU index) (Michael, S., et al., J. Immunol., 1997, 159:3613; J. Immunol. 2000, 164:4178-4184), or IgG4PE_R409K (a human IgG4 modified antibody in which serine at position 228 is substituted with proline, leucine at position 235 is substituted with glutamic acid, and arginine at position 409 is substituted with lysine in the Fc of human IgG4 according to the EU index) (WO2006/033386), and a total of 23 types of antibodies obtained by adding the following Fc amino acid modifications (10-1) to (10-5), which are known to improve a binding activity to human and monkey FcRn, to the Fc region of the antibody A or each of the three types of isototypes of the antibody A were prepared.

<Fc Amino Acid Modification>

(10-1) Amino acid modification in which M at position 252 is substituted with Y, S at position 254 is substituted with T, and T at position 256 is substituted with E according to the EU index (J. Biol. Chem. 2006b; 281:23514-23524)

(10-2) Amino acid modification in which T at position 250 is substituted with Q, and N at position 428 is substituted with L according to the EU index (J. Biol. Chem. 2004; 279:6213-6216)

(10-3) Amino acid modification in which N at position 434 is substituted with A according to the EU index (J. Immunol. 1997; 158:2211-2217), (10-4) Amino acid modification in which V at position 308 is substituted with P according to the EU index (Drug. Metab. Dispos. 2012a; 40:1545-1555)

(10-5) Amino acid modification in which M at position 428 is substituted with L, and N at position 434 is substituted with S according to the EU index (Nat. Biotechnol. 2010; 28:157-159)

Hereinafter, the CH modified antibody in which the CH of the antibody A is substituted with a CH of human IgG2 is referred to as an antibody A_G2. The same applies to CH modified antibodies substituted with other subclasses.

Hereinafter, the CH modified antibodies obtained by adding the above-described amino acid modifications (10-1) to (10-5) to the Fc region of the antibody A are referred to as antibody A_YTE, antibody A_QL, antibody A_A, antibody A_P, and antibody A_LS, respectively. The same applies to CH modified antibodies obtained by adding the above-described amino acid modifications (10-1) to (10-5) to the antibody A_G2, antibody A_G2AAS, and antibody A_G4PE_R409K.

A plasmid comprising a nucleotide sequence encoding the amino acid sequences of the variable region and constant region of the H chain of the antibody A that is prepared in Example 2 was subjected to a restriction enzyme treatment with NheI and BamHI to prepare a vector fragment from which the stationary region was removed. Based on the plasmid fragment, a gene fragment comprising a nucleotide sequence encoding the amino acid sequences of the 23 types of CH modified antibodies described above was synthesized and introduced into an appropriate expression vector to prepare a necessary plasmid. Using the obtained plasmid, an antibody was prepared in the same manner as in Example 2.

[Example 11] Measurement of Binding Activity of Antibody A and CH Modified Antibody of Antibody A to FcRn A binding activity of the antibody A and the CH modified antibodies of the antibody A that are prepared in Examples 2 and 10 to human and monkey FcRn was measured by Biacore according to a method described below.

To HBS-EP+ (Global Life Sciences Technologies Japan K.K., Cat. No. BR-1006-69), 1M hydrochloric acid (FUJI- FILM Wako Pure Chemical Corporation, Cat. No. 083-01095) was added to adjust HBS-EP+ to pH 6. Each antibody was subjected to buffer exchange with the above-described HBS-EP+ at pH 6 using NAP25. The human FcRn and monkey FcRn were also diluted with HBS-EP+ at pH 6. The human FcRn and monkey FcRn used in the experiment were prepared as follows.

A DNA sequence encoding human FcRn (only the amino acids at positions 1 to 297 among the full-length amino acid sequences of human FcRn were used for expression as a soluble molecule), human FcRn-His tag (the amino acid sequence: SEQ ID NO: 54) having 6 histidine added to the C-terminal thereof, and human B2 microglobulin (the amino acid sequence: SEQ ID NO: 55) was inserted downstream of a CMV promoter of a mammal cell expression plasmid. The plasmid was used for transient expression using an Expi293 Expression System Kit (Life Technologies) in the same manner as in Example 2.

Monkey FcRn (only the amino acids at positions 1 to 297 among the full-length amino acid sequence of monkey FcRn were used for expression as a soluble molecule), monkey FcRn-His tag (the amino acid sequence: SEQ ID NO: 56) having six histidines added to the C-terminal thereof, and monkey β2 microglobulin (the amino acid sequence: SEQ ID NO: 57) were also transiently expressed in the same manner as the human FcRn-His tag.

After obtaining each culture supernatant, human and monkey FcRn were purified using Ni-NTA Agarose (QIAGEN, Cat. No. 30210). Purification was performed according to the standard procedures described in the Ni-NTA Agarose manual.

Biacore measurement was performed under the following conditions. Tetra His Antibody BSA Free (QIAGEN) was immobilized on a CM5 sensor chip (Global Life Sciences Technologies Japan K.K., Cat. No. BR100530). Human FcRn and monkey FcRn adjusted to 10 μg/mL were added to a flow cell on which Tetra His Antibody BSA Free was immobilized at a flow rate of 10 μL/min for 120 seconds. Next, each Fc modified antibody was prepared at five concentrations by 3-fold dilution starting from 450 μg/mL, and a binding reaction was monitored for 2 minutes and a dissociation reaction for 5 minutes at a flow rate of 30 μL/min.

The measurement was performed by a multi-cycle method. The obtained sensorgrams were analyzed using Bia Evaluation Software (Global Life Sciences Technologies Japan K.K.), and dissociation constants [kd1/ka1=KD] of the antibodies were calculated. The results are shown in Tables 12 and 13.

TABLE 12

| Antibody name | KD (M) | |
| | h FcRn | cyno FcRn |
| --- | --- | --- |
| A | 5.05E−07 | 2.12E−07 |
| A_A | 3.08E−07 | 1.55E−07 |
| A_P | 1.83E−07 | 6.02E−08 |
| A_QL | 1.87E−07 | Not detected |
| A_YTE | 1.59E−07 | 1.15E−07 |
| A_G2 | 6.24E−07 | 2.33E−07 |
| A_G2_A | 2.86E−07 | 1.33E−07 |
| A_G2_P | 2.34E−07 | 7.82E−08 |
| A_G2_QL | 2.02E−07 | 4.33E−08 |
| A_G2_YTE | 1.86E−07 | 3.91E−08 |
| A_G2AAS | 6.23E−07 | 2.42E−07 |
| A_G2AAAS_A | 2.47E−07 | 1.29E−07 |
| A_G2AAAS_P | 2.20E−07 | 7.53E−08 |

TABLE 12-continued

| Antibody name | KD (M) | |
|---|---|---|
| | h FcRn | cyno FcRn |
| A_G2AAAS_QL | 2.13E−07 | 6.90E−08 |
| A_G2AAAS_YTE | 1.97E−07 | 4.79E−08 |
| A_IgG4PE_R409K | 9.12E−07 | 3.24E−07 |
| A_IgG4PE_R409K_A | 4.29E−07 | 1.90E−07 |
| A_IgG4PE_R409K_P | 1.92E−07 | 7.69E−08 |
| A_IgG4PE_R409K_QL | 2.65E−07 | 8.70E−08 |
| A_IgG4PE_R409K_YTE | 2.27E−07 | 1.23E−07 |

TABLE 13

| Antibody name | KD (M) to hFcRn |
|---|---|
| A_LS | 1.42E−07 |
| A_G2_LS | 3.10E−07 |
| A_G2AAAS_LS | 1.59E−07 |
| A_IgG4PE_R409K_LS | 1.16E−07 |

As shown in Tables 12 and 13, it was confirmed that the CH modified antibodies in which the amino acid modifications described in Example 10 (1) to (5) were introduced into the Fc had an improved binding activity to the human FcRn and monkey FcRn as compared with the antibody A and the isotypes of the antibody A (antibodies A2_G2, A_G2AAAS, and A_IgG4PE_R409K).

[Example 12] Preparation of CH Modified Antibodies of Modified Antibodies I100 and D105

Among the modified antibodies I100 and D105 which were confirmed in Examples 4 and 8 that the antibody degradation was suppressed as compared with the antibody A, CH modified antibodies to which amino acid modifications of the following (12-1) to (12-5) were added were prepared for each of antibodies D105N, I100A, I100H, and I100Y by a method described below.

(12-1) Amino acid modification in which M at position 252 is substituted with Y, S at position 254 is substituted with T, and T at position 256 is substituted with E according to the EU index (12-2) Amino acid modification in which a CH is substituted from human IgG1 to human IgG2, M at position 252 is substituted with Y, S at position 254 is substituted with T, and T at position 256 is substituted with E according to the EU index (12-3) Amino acid modification in which a CH is substituted from human IgG1 to human IgG2, M at position 428 is substituted with L, and N at position 434 is substituted with S according to the EU index (12-4) Amino acid modification in which a CH is substituted from human IgG1 to human IgG4PE_R409K, and V at position 308 is substituted with P according to the EU index (12-5) Amino acid modification in which a CH is substituted from human IgG1 to human IgG4PE_R409K, M at position 428 is substituted with L, and N at position 434 is substituted with S according to the EU index Hereinafter, in the antibody D105N, the CH modified antibodies subjected to the amino acid modification of the above-described (12-1) to (12-5) are described as antibodies D105N_YTE, D105N_G2_YTE, D105N_G2_LS, D105N_G4PE_R409K_P, and D105N_G4PE_R409K_LS, respectively. The same applies to other antibodies.

The amino acid sequences of CHs of the CH modified antibodies with the above-described amino acid modifications (12-1) to (12-5) are set forth in SEQ ID NO: 48, SEQ ID NO: 49, SEQ ID NO: 50, SEQ ID NO: 51, and SEQ ID NO: 52, respectively.

The plasmid prepared in Example 10 was subjected to a restriction enzyme treatment with Bstz17I and NheI to prepare a vector fragment excluding a variable region portion. Based on the plasmid fragment, a gene fragment comprising a nucleotide sequence encoding an amino acid sequence of a VH of each of antibodies D105N, I100A, I100H, and I100Y was synthesized by FASMAC Corporation, and introduced into an appropriate expression vector to prepare a necessary plasmid. Using the obtained plasmid, each antibody was prepared in the same manner as in Example 2.

[Example 13] Measurement of FGF23 Neutralizing Activity of Heavy Chain Constant Region Modified Antibody An FGF23 neutralizing activity of the 20 types of CH modified antibodies prepared in Example 12 was measured in the same manner as in Example 9. The obtained results are shown in Table 14.

TABLE 14

| Antibody name | IC50 (ng/mL) |
|---|---|
| A | 1.2 |
| D105N_YTE | 12.4 |
| D105N_G2_YTE | 12.4 |
| D105N_G2_LS | 12.4 |
| D105N_IgG4PE_R409K_P | 13.3 |
| D105N_IgG4PE_R409K_LS | 11.7 |
| I100A_YTE | 4 |
| I100A_G2_YTE | 5 |
| I100A_G2_LS | 2.4 |
| I100A_IgG4PE_R409K_P | 5.2 |
| I100A_IgG4PE_R409K_LS | 6.6 |
| I100H_YTE | 11.3 |
| I100H_G2_YTE | 8.9 |
| I100H_G2_LS | 13 |
| I100H_IgG4PE_R409K_P | 14.4 |
| I100H_IgG4PE_R409K_LS | 13.1 |
| I100Y_YTE | 5.6 |
| I100Y_G2_YTE | 2.9 |
| I100Y_G2_LS | 4.4 |
| I100Y_IgG4PE_R409K_P | 4.1 |
| I100Y_IgG4PE_R409K_LS | 2.9 |

As shown in Table 14, the antibodies comprising the same amino acid sequence in the variable region exhibited the same extent of FGF23 neutralizing activity even when the amino acid sequence in the constant region was changed. From the above, it was confirmed that the amino acid modification of the heavy chain constant region in each antibody did not affect the FGF23 neutralizing activity of the antibody.

[Example 14] Preparation of Modified Antibody with Improved Antigen Binding Activity With respect to the antibodies I100A and I100Y, in order to improve the antigen binding activity described in Tables 2 and 3, affinity maturation was performed using a phage display method at Abwiz Bio, and amino acid sequence information on the following (14-1) to (14-9) was obtained.

(14-1) A VH comprising the amino acid sequence represented by SEQ ID NO: 1, in which the amino acid at position 51 is substituted with V, the amino acid at position 54 is substituted with F, the amino acid at position 55 is substituted with W, the amino acid at position 57 is substituted with R, the amino acid at position 58 is substituted with W, and the amino acid at position 100 is substituted with A in the amino acid sequence represented by SEQ ID NO: 1 (H2B11_A, amino acid sequence: SEQ ID NO: 38)

(14-2) A VH comprising the amino acid sequence represented by SEQ ID NO: 1, in which the amino acid at position 50 is substituted with L, the amino acid at position 54 is substituted with W, the amino acid at position 55 is substituted with H, the amino acid at position 57 is substituted with T, the amino acid at position 58 is substituted with F, and the amino acid at position 100 is substituted with A in the amino acid sequence represented by SEQ ID NO: 1 (J2H2B9_A, amino acid sequence: SEQ ID NO: 39)

(14-3) A VH comprising the amino acid sequence represented by SEQ ID NO: 1, in which the amino acid at position 50 is substituted with V, the amino acid at position 54 is substituted with F, the amino acid at position 55 is substituted with C, the amino acid at position 57 is substituted with F, the amino acid at position 58 is substituted with V, and the amino acid at position 100 is substituted with A in the amino acid sequence represented by SEQ ID NO: 1 (J2H2E9_A, amino acid sequence: SEQ ID NO: 40)

(14-4) A VH comprising the amino acid sequence represented by SEQ ID NO: 1, in which the amino acid at position 51 is substituted with L, the amino acid at position 54 is substituted with W, the amino acid at position 55 is substituted with T, the amino acid at position 57 is substituted with Y, the amino acid at position 58 is substituted with R, and the amino acid at position 100 is substituted with A in the amino acid sequence represented by SEQ ID NO: 1 (2H2E1_A, amino acid sequence: SEQ ID NO: 41)

(14-5) A VH comprising the amino acid sequence represented by SEQ ID NO: 1, in which the amino acid at position 54 is substituted with W, the amino acid at position 55 is substituted with V, the amino acid at position 57 is substituted with R, the amino acid at position 58 is substituted with A, and the amino acid at position 100 is substituted with A in the amino acid sequence represented by SEQ ID NO: 1 (2H2E5_A, amino acid sequence: SEQ ID NO: 42)

(14-6) A VH comprising the amino acid sequence represented by SEQ ID NO: 1, in which the amino acid at position 51 is substituted with V, the amino acid at position 54 is substituted with Y, the amino acid at position 55 is substituted with R, the amino acid at position 57 is substituted with K, the amino acid at position 58 is substituted with W, and the amino acid at position 100 is substituted with Y in the amino acid sequence represented by SEQ ID NO: 1 (2H2E8_A, amino acid sequence: SEQ ID NO: 43)

(14-7) A VL comprising the amino acid sequence represented by SEQ ID NO: 2, in which the amino acid at position 91 is substituted with M, the amino acid at position 92 is substituted with Y, the amino acid at position 94 is substituted with D, and the amino acid at position 96 is substituted with N in the amino acid sequence represented by SEQ ID NO: 2 (L3G12, amino acid sequence: SEQ ID NO: 44)

(14-8) A VL comprising the amino acid sequence represented by SEQ ID NO: 2, in which the amino acid at position 28 is substituted with D, the amino acid at position 29 is substituted with V, the amino acid at position 31 is substituted with T, and the amino acid at position 34 is substituted with L in the amino acid sequence represented by SEQ ID NO: 2 (L1H8, amino acid sequence: SEQ ID NO: 45)

(14-9) A VL comprising the amino acid sequence represented by SEQ ID NO: 2, in which the amino acid at position 91 is substituted with L, the amino acid at position 92 is substituted with Y, the amino acid at position 94 is substituted with D, and the amino acid at position 96 is substituted with D in the amino acid sequence represented by SEQ ID NO: 2 (2L3H7, amino acid sequence: SEQ ID NO: 46)

[Example 15] Preparation of Modified Antibody

Using the amino acid sequence information obtained in Example 14 and the amino acid sequence of the VH described in (15-1), the modified antibodies A-1 to A-8 described in Table 15 were prepared.

(15-1) A VH comprising the amino acid sequence represented by SEQ ID NO: 1, in which the amino acid at position 50 is substituted with L, the amino acid at position 54 is substituted with W, the amino acid at position 55 is substituted with H, the amino acid at position 57 is substituted with T, the amino acid at position 58 is substituted with F, and the amino acid at position 100 is substituted with Y in the amino acid sequence represented by SEQ ID NO: 1 (J2H2B9_Y, amino acid sequence: SEQ ID NO: 47)

TABLE 15

| Antibody name | SEQ ID NO of VH | SEQ ID NO of VL | SEQ ID NO of heavy chain constant region |
|---|---|---|---|
| A | SEQ ID NO: 1 | SEQ ID NO: 2 | SEQ ID NO: 53 |
| A-1 | SEQ ID NO: 39 | SEQ ID NO: 2 | SEQ ID NO: 48 |
| A-2 | SEQ ID NO: 47 | SEQ ID NO: 2 | SEQ ID NO: 48 |
| A-3 | SEQ ID NO: 3 | SEQ ID NO: 44 | SEQ ID NO: 48 |
| A-4 | SEQ ID NO: 6 | SEQ ID NO: 44 | SEQ ID NO: 48 |
| A-5 | SEQ ID NO: 3 | SEQ ID NO: 45 | SEQ ID NO: 48 |
| A-6 | SEQ ID NO: 6 | SEQ ID NO: 45 | SEQ ID NO: 48 |
| A-7 | SEQ ID NO: 3 | SEQ ID NO: 46 | SEQ ID NO: 48 |
| A-8 | SEQ ID NO: 6 | SEQ ID NO: 46 | SEQ ID NO: 48 |

A plasmid comprising a nucleotide sequence encoding the amino acid sequence of each antibody was prepared in the same manner as in Example 12, and an antibody was prepared from the plasmid in the same manner as in Example 2.

[Example 16] Evaluation of Modified Antibody

The eight types of modified antibodies prepared in Example 15 and the antibody A as a control were used to evaluate an antigen binding activity, an FGF23 neutralizing activity, and thermal stability. For all modified antibodies, various measurements were performed by diluting a sample using a D-PBS buffer (Nacalai Tesque, Inc., Code 14249-24) such that a concentration thereof was adjusted to 0.5 mg/mL in according to the purpose.

16-1) Measurement of Antigen Binding Activity of Modified Antibody

A binding activity to human FGF23 was measured in the same manner as in Example 3. A sensor chip used was a Protein A sensor chip (Global Life Sciences Technologies Japan K.K., Cat. No. 29127555) instead of a CM5 sensor chip having an immobilized anti-human IgG antibody. An association rate constant (ka), a dissociation rate constant (kd), and a dissociation constant [kd1/ka1=KD] calculated from the association rate constant (ka) and the dissociation rate constant (kd) of each antibody are shown in Table 16.

TABLE 16

| Antibody name | Antigen binding activity KD (M) | FGF23 neutralizing activity IC50 (ng/mL) ( ) is value of antibody A in same measurement lot | pI (4 degrees, PBS) |
|---|---|---|---|
| A-1 | 8.22E–12 | 3.5 (3.1) | 7.84 |
| A-2 | 8.08E–12 | 3.4 (3.1) | 7.87 |
| A-3 | 8.27E–12 | 2.7 (3.3) | 7.72 |
| A-4 | 8.74E–12 | 1.9 (3.3) | 7.73 |
| A-5 | 3.61E–12 | 1.9 (3.3) | 7.31 |
| A-6 | 1.13E–11 | 3.6 (3.3) | 7.35 |
| A-7 | 1.61E–11 | 3.2 (3.3) | 7.26 |
| A-8 | 6.70E–12 | 2.4 (3.3) | 7.32 |
| A | 8.77E–12 | 3.3 | 8.19 |

It was confirmed from Table 16 that all of the antibodies A-1 to A-8 had an antigen binding activity comparable to that of the antibody A.

In Example 3, the antigen binding activity of the antibody I100A and the antibody I100Y was reduced as compared with the antibody A. In any of the antibodies A-1 to A-8, the amino acid residue at position 100 in the VH is A or Y.

From the above, it was confirmed that, for the antibody A, substitution of the amino acid residue at position 100 in the VH with A or Y reduces the antigen binding activity of the antibody, whereas substitution of additional amino acid residues contained in the antibodies A-1 to A-8 improves the antigen binding activity of the antibody to the same extent as that of the antibody A.

16-2) Measurement of Human FGF23 Neutralizing Activity

The human FGF23 neutralizing activity of the modified antibody was measured in the same manner as in Example 9. The obtained results are shown in Table 16. From Table 16, it was confirmed that all of the modified antibodies had an FGF23 neutralizing activity comparable to that of the antibody A in the same measurement lot.

In Example 9, the FGF23 neutralizing activity of the antibody I100A and the antibody I100Y was lower than that of the antibody A. In any of the antibodies A-1 to A-8, the amino acid residue at position 100 in the VH is A or Y.

From the above, it was confirmed that, substitution of the amino acid residue at position 100 in the VH with A or Y in the antibody A reduces the FGF23 neutralizing activity of the antibody, whereas substitution of additional amino acid residues contained in antibodies A-1 to A-8 improves the neutralizing activity of the antibody to the same extent as that of the antibody A.

16-3) Confirmation of Isoelectric Point An isoelectric point of each antibody was determined using an iCE3 system (Protein Simple). Pharmalyte 3-10 for IEF (Global Life Sciences Technologies Japan K.K., Cat. No. 17-0456-01) was used as a measurement carrier, pI Marker 5.12 (Protein Simple, Cat. No. 102224) was used as an acidic marker, and pI Marker 9.77 (Protein Simple, Cat. No. 102219) was used as a basic marker. The measurement method was based on a standard protocol.

The obtained results are shown in Table 16. It was confirmed from Table 16 that all of the modified antibodies had a reduced pI as compared with the antibody A.

16-4) Confirmation of Degradation Suppression Ratio of Antibody

Degradation suppression ratios were confirmed for the antibody A-1 to the antibody A-8 in the same manner as in Example 4. In the present Example, each antibody was allowed to stand at 40 degrees for two weeks, and antibody degradation was confirmed using a Bioanalyzer Electrophoresis System (Agilent Technologies, Inc.) and an Agilent Protein 230 kit (Agilent Technologies, Inc., Cat. 5067-1517). With respect to sample preparation and migration conditions, experiments were performed according to the protocol attached to the kit. In the obtained electropherogram, a band of the H chain of the antibody was detected at 63 kDa, and a band corresponding to a degradation product of the antibody was detected at about 55 kDa. A peak area ratio (%) of the band corresponding to the degradation product of the antibody and a ratio (%) of a degradation band peak area ratio of each antibody to the antibody A are shown in Tables 17 and 18.

TABLE 17

| Antibody name | Degradation band peak area ratio (%) | Ratio of degradation band peak area ratio (%) |
|---|---|---|
| A | 39.2 | 100 |
| A-1 | 14.6 | 37.2 |
| A-2 | 14.8 | 37.8 |
| A-3 | 15 | 38.3 |
| A-4 | 7.6 | 19.4 |
| A-5 | 26.8 | 68.4 |
| A-6 | 7.7 | 19.6 |

TABLE 18

| Antibody name | Degradation band peak area ratio (%) | Ratio of degradation band peak area ratio (%) |
|---|---|---|
| A | 39.4 | 100 |
| A-7 | 9.8 | 24.9 |
| A-8 | 5.4 | 13.7 |

As shown in Tables 17 and 18, it was confirmed that degradation was suppressed in all of the antibodies A-1 to A-8 as compared with the antibody A.

16-5) Confirmation of Thermal Stability

Thermal stability of six types of antibodies, i.e., the antibody A, antibody A_YTE, antibody A-1, antibody A-3, antibody A-5, and antibody A-8, was evaluated in the same manner as described in Example 5. The obtained results are shown in Table 19.

TABLE 19

| Antibody name | Fab (degree) | CH2 or Fab + CH2 (degree) | CH3 (degree) |
|---|---|---|---|
| A | 66.9 | 69.7 (CH2) | 82.9 |
| A_YTE | 65.7 | 70.2 (CH2) | 83.0 |
| A-1 | | 70.1 (Fab + CH2) | 82.6 |
| A-3 | | 69.4 (Fab + CH2) | 82.9 |
| A-5 | 64.6 | 70.8 (CH2) | 82.6 |
| A-8 | 64.2 | 70.9 (CH2) | 82.8 |

As shown in Table 19, there was no difference in the thermal stability of each site of the antibody between the antibody A and the antibody A_YTE. On the other hand, it was confirmed that the antibodies A-1 and A-3, which comprise the same heavy chain constant region amino acid sequence as the antibody A_YTE, had Fab thermal stability improved by about 3 degrees as compared with the antibody A and antibody A_YTE.

[Example 17] Preparation of Antibody A-9 and Antibody A-10

The antibody A-9 and the antibody A-10 shown in Table 20 were prepared in the same manner as in Example 2 (hereinafter, the antibody A-9 and the antibody A-10 may be referred to as modified antibodies).

As an L chain expression vector for the antibody A-9, a pcDNA3.4 vector (Invitrogen) was used instead of the pCI vector used in Example 2. For both the antibody A-9 and the antibody A-10, an L chain expression vector and an H chain expression vector were mixed at a ratio of 1:1 and transfected into cells.

TABLE 20

| Antibody name | SEQ ID NO of VH | SEQ ID NO of VL | SEQ ID NO of heavy chain constant region |
|---|---|---|---|
| A-9 | SEQ ID NO: 3 | SEQ ID NO: 58 | SEQ ID NO: 48 |
| A-10 | SEQ ID NO: 6 | SEQ ID NO: 59 | SEQ ID NO: 48 |

For the VL of the antibody A-9, affinity maturation of the antibody I100A was performed using a phage display method at Abwiz Bio, and the following amino acid sequence information was obtained.

A VL comprising the amino acid sequence represented by SEQ ID NO: 2, in which the amino acid at position 92 is substituted with W, the amino acid at position 94 is substituted with D, and the amino acid at position 96 is substituted with D in the amino acid sequence represented by SEQ ID NO: 2 (amino acid sequence: SEQ ID NO: 58)

As the VL of the antibody A-10, the following VL was designed and used.

A VL comprising the amino acid sequence represented by SEQ ID NO: 2, in which the amino acid at position 92 is substituted with Y, the amino acid at position 94 is substituted with D, and the amino acid at position 96 is substituted with D in the amino acid sequence represented by SEQ ID NO: 2 (amino acid sequence: SEQ ID NO: 59)

[Example 18] Evaluation of Modified Antibody

The two types of modified antibodies prepared in Example 17 and the antibody A as a control were used to evaluate an antigen binding activity, an FGF23 neutralizing activity, and thermal stability. For all modified antibodies, various measurements were performed by diluting a sample using a D-PBS buffer (Nacalai Tesque, Inc., Code 14249-24) such that a concentration thereof was adjusted to 1 mg/mL in according to the purpose.

18-1) Measurement of Antigen Binding Activity of Modified Antibody

A binding activity to human FGF23 was measured in the same manner as in Example 16. An association rate constant (ka), a dissociation rate constant (kd), and a dissociation constant [kd1/ka1=KD] calculated from the association rate constant (ka) and the dissociation rate constant (kd) of each antibody are shown in Table 21.

TABLE 21

| Antibody name | Antigen binding activity KD (M) | FGF23 neutralizing activity IC50 (ng/ml) ( ) is value of antibody A in same measurement lot | pI (4 degrees, PBS) |
|---|---|---|---|
| A-9 | 6.87E–12 | 1.0 (3.2) | 7.69 |
| A-10 | 2.02E–11 | 1.5 (2.8) | 7.53 |
| A | 1.44E–11 | 3.2 | 8.19 |

It was confirmed from Table 21 that the antibody A-9 had an antigen binding activity two times stronger than that of the antibody A, and the antibody A-10 had an antigen binding activity comparable to that of the antibody A. In Example 3, the antibody I100A and the antibody I100Y had a reduced antigen binding activity as compared with the antibody A. In the antibodies A-9 and A-10, the amino acid residues at position 100 in the VH are A and Y, respectively.

From the above, it was confirmed that substitution of the amino acid residue at position 100 in the VH of the antibody A with A or Y reduces the antigen binding activity of the antibody, whereas substitution of additional amino acid residues contained in the antibody A-9 and the antibody I100Y improves the binding activity of the antibody to be equal to or greater than that of the antibody A.

18-2) Measurement of Human FGF23 Neutralizing Activity

The human FGF23 neutralizing activity of the modified antibody was measured in the same manner as in Example 9. The obtained results are shown in Table 21. It was confirmed from Table 21 that the antibody A-9 had an FGF23 neutralizing activity three times stronger than that of the antibody A, and the antibody A-10 had an FGF23 neutralizing activity two times stronger than that of the antibody A.

In Example 9, the neutralizing activity of I100A and I100Y was reduced as compared with the antibody A. In the antibodies A-9 and A-10, the amino acid residues at position 100 in the VH are A and Y, respectively.

From the above, it was confirmed that substitution of the amino acid residue at position 100 in the VH of the antibody A with A or Y reduces the FGF23 neutralizing activity of the antibody, whereas substitution of additional amino acid residues contained in the antibody A-9 and the antibody A-10 improves the FGF23 neutralizing activity of the antibody to be equal to or greater than that of the antibody A.

[Example 19] Confirmation of Degradation Suppression Ratio of Modified Antibody

A degradation suppression ratio was confirmed using four types of modified antibodies, i.e., the antibody A-1, the antibody A-3, the antibody A-5, and the antibody A-8, and the antibody A as a control.

The antibody used in the present Example was prepared by inserting a target gene sequence into a mammalian expression vector and introducing the vector into CHO cells, and then obtaining purified antibody from a mammalian cell culture supernatant by affinity purification using MabSelect SuRe (Global Life Sciences Technologies Japan K.K.) and cation exchange chromatography. Using NAP25 (Global Life Sciences Technologies Japan K.K.), a solvent of an antibody solution was replaced with solvents at pH 4 and pH 4.5 containing 10 mM sodium L-glutamate, 262 mM D-sorbitol, and 0.05 mg/mL Polysorbase 80, and a protein concentration was adjusted to 1 mg/mL.

The obtained antibody solution was allowed to stand at 40 degrees for one month and at 25 degrees for three months, and then frozen at −80 degrees. After the antibody solution was thawed, degradation of the antibody was confirmed using a biopharmaceutical analysis system PA800Plus (SCIEX). Basic conditions such as sample preparation and analysis were performed according to a method of Oscar Salas-Solano et al. (2006, Anal. Chem.: 6583-6594), with appropriate modifications.

With respect to a peak area ratio (%) of a band corresponding to a degradation product of the antibody, results at pH 4.5 were shown in Table 22, and results at pH 5.0 were shown in Table 23. A sample frozen at −80 degrees immediately after solvent replacement was designated as "Initial," a sample left standing at 40 degrees for one month and then frozen at −80 degrees was designated as "40° C. 1M" and a sample left standing at 25 degrees for three months and then frozen at −80 degrees was designated as "25° C. 3M". All samples were melted under the same conditions and then measured.

TABLE 22

| Antibody name | Degradation band peak area ratio Initial (%) | Degradation band peak area ratio 40° C. 1M (%) | Degradation band peak area ratio 25° C. 3M (%) |
|---|---|---|---|
| A | 2.5 | 47.2 | 36.8 |
| A-1 | 0.4 | 17.7 | 9.3 |
| A-3 | 0.3 | 14.2 | 6.7 |
| A-5 | 0.7 | 30.8 | 18.6 |
| A-8 | 0.1 | 5.8 | 1.3 |

TABLE 23

| Antibody name | Degradation band peak area ratio Initial (%) | Degradation band peak area ratio 40° C. 1M (%) | Degradation band peak area ratio 25° C. 3M (%) |
|---|---|---|---|
| A | 2.5 | 19.6 | 16.8 |
| A-1 | 0.4 | 9.0 | 5.4 |
| A-3 | 0.3 | 6.1 | 3.0 |
| A-5 | 0.7 | 15.1 | 9.4 |
| A-8 | 0.1 | 3.5 | 0.9 |

As shown in Tables 22 and 23, as in Example 16, it was confirmed that, even under buffer conditions of pH 4.5 and pH 5.0 and storage conditions of 40 degrees for one month and 25 degrees for three months, degradation of the antibody A-1, the antibody A-3, the antibody A-5, and the antibody A-8 was all suppressed as compared with the antibody A.

[Example 20] Confirmation of Degradation Suppression Ratio of Modified Antibody

A degradation suppression ratio was confirmed using two types of modified antibodies prepared in Example 17 and the antibody A as a control.

The antibody A and the antibody A-1 used in the present Example were prepared by inserting a target gene sequence into a mammalian expression vector and introducing the vector into CHO cells, and then obtaining purified antibody from a mammalian cell culture supernatant by affinity purification using MabSelect SuRe (Global Life Sciences Technologies Japan K.K.) and cation exchange chromatography. Using NAP25 (Global Life Sciences Technologies Japan K.K.), a solvent of the antibody solution was replaced with a solvent of pH 4 and pH 4.5 containing 10 mM sodium L-glutamate, 262 mM D-sorbitol, and 0.05 mg/mL Polysorbate, and a protein concentration was adjusted to 1 mg/mL.

The obtained antibody solution was allowed to stand at 40 degrees for one month, and then degradation of the antibody was confirmed using a microchip electrophoresis system LabChip (PerkinElmer) and a Protein Clear Reagent kit (PerkinElmer, Cat. CLS960014). With respect to sample preparation and migration conditions, experiments were performed according to the protocol attached to the kit.

With respect to a peak area ratio (%) of a band corresponding to a degradation product of the antibody in the measurement results under reducing conditions, results at pH 4.0 are shown in Table 24, results at pH 4.5 are shown in Table 25, and results at pH 5.0 are shown in Table 26.

TABLE 24

| Antibody name | Degradation band peak area ratio (%) | Ratio of degradation band peak area ratio (%) |
|---|---|---|
| A | 32.7 | 100 |
| A-1 | 11.2 | 34.2 |
| A-9 | 9.2 | 28.0 |
| A-10 | 5.1 | 15.6 |

TABLE 25

| Antibody name | Degradation band peak area ratio (%) | Ratio of degradation band peak area ratio (%) |
|---|---|---|
| A | 20.7 | 100 |
| A-1 | 7.1 | 34.4 |
| A-9 | 5.4 | 26.0 |
| A-10 | 3.2 | 15.3 |

TABLE 26

| Antibody name | Degradation band peak area ratio (%) | Ratio of degradation band peak area ratio (%) |
|---|---|---|
| A | 8.2 | 100 |
| A-1 | 3.5 | 42.7 |
| A-9 | 2.6 | 32.1 |
| A-10 | 1.7 | 21.0 |

As shown in Tables 24, 25, and 26, it was confirmed that the degradation of the antibody A-9 and the antibody A-10 was suppressed as compared with the antibody A under buffer conditions of pH 4.0, pH 4.5, or pH 5.0 and storage conditions of 40 degrees for one month.

Example 21

A concentration (mg/dL) of inorganic phosphorus in serum was measured in order to confirm sustainability of a pharmacological action when a test antibody was administered subcutaneously at a single dose to male cynomolgus monkeys.

The antibody A8 (1.8 mg/kg) was administered subcutaneously as the test antibody. The blood was collected over time for 56 days after administration, and the concentration of inorganic phosphorus in serum was measured at each time point. The concentration of phosphorus was measured by a PNP-XDH method using a clizer (JCA-BM6070).

The obtained results are shown in Table 27. After the administration of the antibody A-8, the concentration of inorganic phosphorus in serum increased from Day 3 after the administration, and remained higher than a concentration of inorganic phosphorus in the baseline (a concentration of phosphorus at Day 0 in Table 27) even on Day 56 after the administration.

TABLE 27

| | | A-8 (1.8 mg/kg) |
|---|---|---|
| Days | −7 | 5.54 ± 0.90 |
| | −3 | 5.53 ± 0.65 |
| | 0 | 5.05 ± 0.86 |
| | 3 | 10.4 ± 0.77 |
| | 7 | 10.9 ± 0.64 |
| | 10 | 10.7 ± 0.84 |
| | 14 | 10.1 ± 0.82 |
| | 17 | 9.02 ± 0.79 |
| | 21 | 9.18 ± 0.87 |
| | 24 | 9.14 ± 0.74 |
| | 28 | 8.28 ± 0.64 |
| | 35 | 8.61 ± 0.82 |
| | 42 | 7.9 ± 1.11 |
| | 49 | 7.46 ± 1.17 |
| | 56 | 7.37 ± 0.74 |

On the other hand, after burosumab (KRN23, Crysvita) was administered subcutaneously at a single dose of 3 mg/kg to cynomolgus monkeys, the concentration of inorganic phosphorus in serum increased from Day 3 after the administration, and on Day 42 after the administration, the concentration of inorganic phosphorus decreased to the same level as that of a medium administration group and the baseline (administration on Day 0) (Crysvita Subcutaneous Injection Interview Form revised in December 2021 (fifth edition) P44).

Accordingly, it was shown that the antibody A-8 had a duration of the concentration of inorganic phosphorus in serum in cynomolgus monkeys longer than that of burosumab.

The antibody A-1 and the antibody A-5 were subcutaneously administered at 3 mg/kg to cynomolgus monkeys, and the concentration of inorganic phosphorus in serum was measured in the same manner as above. As a result, in these antibodies, the concentration of inorganic phosphorus in serum increased from Day 3 after the administration, and the concentration of inorganic phosphorus decreased to the baseline on the Day 42 after the administration, as in the case of burosumab.

The amino acid sequence in the heavy chain constant region of burosumab is represented by SEQ ID NO: 53, and the amino acid sequence in the heavy chain constant region of each of the antibody A-1, the antibody A-5, and the antibody A-8 is represented by SEQ ID NO: 48. Among the antibody A-1, the antibody A-5, and the antibody A-8, which have the same heavy chain constant region amino acid sequence, only in the antibody A-8, the concentration of inorganic phosphorus in serum was maintained longer than that of burosumab in cynomolgus monkeys.

Accordingly, it was suggested that the duration of the concentration of inorganic phosphorus in serum in the antibody A-8 is longer than that in burosumab, the antibody A-1, or the antibody A-5, not due to the difference in amino acid sequence in the heavy chain constant region but due to the difference in amino acid sequence in the variable region.

Example 22

A concentration (mg/dL) of inorganic phosphorus in serum was measured in the same manner as in Example 21.

The antibody A-9 and the antibody A-10 (3.0 mg/kg) as test antibodies were administered subcutaneously. The blood was collected over time for 57 days after administration, and the concentration of inorganic phosphorus in serum was measured at each time point.

The obtained results are shown in Table 28.

TABLE 28

| | | A-9 | A-10 |
|---|---|---|---|
| Days | 0 | 6.37 ± 0.21 | 5.83 ± 0.67 |
| | 1 | 6.27 ± 0.31 | 5.60 ± 0.35 |
| | 4 | 11.4 ± 0.95 | 10.5 ± 0.15 |
| | 8 | 11.1 ± 1.80 | 10.5 ± 0.97 |
| | 11 | 10.9 ± 0.75 | 10.4 ± 1.04 |
| | 15 | 9.80 ± 1.05 | 9.20 ± 1.73 |
| | 18 | 8.77 ± 1.42 | 7.07 ± 1.25 |
| | 22 | 9.90 ± 0.98 | 8.40 ± 1.71 |
| | 25 | 9.40 ± 0.66 | 7.67 ± 1.00 |
| | 29 | 9.53 ± 0.81 | 7.60 ± 0.92 |
| | 32 | 8.90 ± 0.92 | 7.93 ± 0.49 |
| | 36 | 8.03 ± 0.49 | 6.47 ± 1.07 |
| | 39 | 8.67 ± 0.68 | 7.20 ± 0.60 |
| | 43 | 8.37 ± 1.45 | 7.17 ± 0.87 |
| | 46 | 7.47 ± 1.17 | 7.67 ± 0.95 |
| | 50 | 8.97 ± 0.55 | 7.23 ± 1.12 |
| | 53 | 7.00 ± 1.55 | 6.33 ± 0.68 |
| | 57 | 7.67 ± 0.74 | 6.10 ± 1.04 |

As shown in Table 28, as in the case of the antibody A-8 in Example 22, after administration of the antibody A-9 and the antibody A-10, the concentration of inorganic phosphorus in serum increased from Day 3 after the administration, and remained higher than a concentration of inorganic phosphorus in the baseline (a concentration of phosphorus at Day 0 in Table 28) even on Day 57 after the administration.

The amino acid sequences of the heavy chain constant regions of the antibody A-9 and the antibody A-10 are the same as the amino acid sequences of the heavy chain constant regions of the antibody A-1, the antibody A-5, and the antibody A-8, and are the amino acid sequence represented by SEQ ID NO: 48.

Accordingly, it was suggested that the duration of the concentration of inorganic phosphorus in serum in the antibody A-9 and the antibody A-10 is longer than that in burosumab, the antibody A-1, or the antibody A-5, not due to the difference in amino acid sequence in the heavy chain constant region, but due to the difference in amino acid sequence in the variable region as in the antibody A-8.

Although the present invention has been described in detail with reference to specific embodiments, it is apparent to those skilled in the art that various changes and modifications can be made without departing from the spirit and scope of the present invention. The present application is based on a Japanese patent application (JP2022-128011A) filed on Aug. 10, 2022 and a Japanese patent application (JP2022-164256A) filed on Oct. 12, 2022, the disclosure of which is hereby incorporated by reference herein in its entirety. All references cited herein are incorporated in their entirety.

SEQUENCE LISTING FREE TEXT

SEQ ID NO: 1: amino acid sequence of VH of antibody A
SEQ ID NO: 2: amino acid sequence of VL of antibody A
SEQ ID NO: 3: amino acid sequence of VH of antibody I100A SEQ ID NO: 4: amino acid sequence of VH of antibody I100L SEQ ID NO: 5: amino acid sequence of VH of antibody I100V SEQ ID NO: 6: amino acid sequence of VH of antibody I100Y SEQ ID NO: 7: amino acid sequence of VH of antibody I100W SEQ ID NO: 8: amino acid sequence of VH of antibody I100T SEQ ID NO: 9: amino acid sequence of VH of antibody I100S SEQ ID NO: 10: amino acid sequence of VH of antibody I100R SEQ ID NO: 11: amino acid sequence of VH of antibody I100Q SEQ ID NO: 12: amino acid sequence of VH of antibody I100N SEQ ID NO: 13: amino acid sequence of VH of antibody I100M SEQ ID NO: 14: amino acid sequence of VH of antibody I100K SEQ ID NO: 15: amino acid sequence of VH of antibody I100H SEQ ID NO: 16: amino acid sequence of VH of antibody I100G SEQ ID NO: 17: amino acid sequence of VH of antibody I100F SEQ ID NO: 18: amino acid sequence of VH of antibody I100E SEQ ID NO: 19: amino acid sequence of VH of antibody I100D SEQ ID NO: 20: amino acid sequence of VH of antibody D105A SEQ ID NO: 21: amino acid sequence of VH of antibody D105E SEQ ID NO: 22: amino acid sequence of VH of antibody D105F SEQ ID NO: 23: amino acid sequence of VH of antibody D105G SEQ ID NO: 24: amino acid sequence of VH of antibody D105H SEQ ID NO: 25: amino acid sequence of VH of antibody D105I SEQ ID NO: 26: amino acid sequence of VH of antibody D105K SEQ ID NO: 27: amino acid sequence of VH of antibody D105L SEQ ID NO: 28: amino acid sequence of VH of antibody D105M SEQ ID NO: 29: amino acid sequence of VH of antibody D105P SEQ ID NO: 30: amino acid sequence of VH of antibody D105Q SEQ ID NO: 31: amino acid sequence of VH of antibody D105R SEQ ID NO: 32: amino acid sequence of VH of antibody D105V SEQ ID NO: 33: amino acid sequence of VH of antibody D105W SEQ ID NO: 34: amino acid sequence of VH of antibody D105Y SEQ ID NO: 35: amino acid sequence of VH of antibody D105T SEQ ID NO: 36: amino acid sequence of VH of antibody D105N SEQ ID NO: 37: amino acid sequence of VH of antibody D105S SEQ ID NO: 38: amino acid sequence of H2B11_A SEQ ID NO: 39: amino acid sequence of J2H2B9_A SEQ ID NO: 40: amino acid sequence of J2H2E9_A SEQ ID NO: 41: amino acid sequence of 2H2E1_A SEQ ID NO: 42: amino acid sequence of 2H2E5_A SEQ ID NO: 43: amino acid sequence of 2H2E8_Y SEQ ID NO: 44: amino acid sequence of L3G12

SEQ ID NO: 45: amino acid sequence of L1H8

SEQ ID NO: 46: amino acid sequence of 2L3H7

SEQ ID NO: 47: amino acid sequence of J2H2B9_Y

SEQ ID NO: 48: amino acid sequence of CH of YTE

SEQ ID NO: 49: amino acid sequence of CH of G2_YTE

SEQ ID NO: 50: amino acid sequence of CH of G2_LS

SEQ ID NO: 51: amino acid sequence of CH of G4PE_R409K_P

SEQ ID NO: 52: amino acid sequence of CH of G4PE_R409K_LS

SEQ ID NO: 53: amino acid sequence of G1 constant region

SEQ ID NO: 54: amino acid sequence of human FcRn extracellular domain His-tag body SEQ ID NO:55: amino acid sequence of human β2 microglobulin SEQ ID NO: 56: amino acid sequence of cynomolgus monkey FcRn extracellular domain His-tag body SEQ ID NO: 57: amino acid sequence of cynomolgus monkey β2 microglobulin SEQ ID NO: 58: amino acid sequence of VL of antibody A-9

SEQ ID NO: 59: amino acid sequence of VL of antibody A-10

---

The invention claimed is:

1. An antibody or an antibody fragment thereof which binds to FGF23, wherein the antibody comprises a heavy chain variable region (VH) comprising the amino acid sequence represented by SEQ ID NO: 39 and a light chain variable region (VL) comprising the amino acid sequence represented by SEQ ID NO: 2.

2. The antibody or the antibody fragment thereof according to claim 1, wherein the subclass of the antibody is IgG1, IgG2, IgG3 or IgG4.

3. The antibody or the antibody fragment thereof according to claim 1, wherein the Fc region of the antibody is one selected from the following (a) to (e):

(a) an Fc region comprising substitution of the amino acid residue at position 252 with tyrosine residue, substitution of the amino acid residue at position 254 with threonine residue, and substitution of the amino acid residue at position 256 with glutamic acid residue according to the EU index, (b) an Fc region comprising substitution of the amino acid residue at position 428 with leucine residue, and substitution of the amino acid residue at position 434 with serine residue according to the EU index, (c) an Fc region comprising substitution of the amino acid residue at position 308 with proline residue according to the EU index, (d) an Fc region comprising substitution of the amino acid residue at position 250 with glutamine residue, and substitution of the amino acid residue at position 428 with leucine residue according to the EU index, and (e) an Fc region comprising substitution of the amino acid residue at position 434 with alanine residue according to the EU index.

4. The antibody or the antibody fragment thereof according to claim 1, wherein the heavy chain constant region of the antibody comprises the amino acid sequence represented by SEQ ID NO: 48, 49, 50, 51 or 52.

5. The antibody or the antibody fragment thereof according to claim 1, wherein the antibody fragment is one selected from Fab, Fab', (Fab')₂, scFv, diabody, and dsFv.

6. A composition comprising:

the antibody or the antibody fragment thereof according to claim 1 and a pharmacologically acceptable carrier.

* * * * *